(12) United States Patent
Buerckstuemmer

(10) Patent No.: US 10,450,586 B2
(45) Date of Patent: Oct. 22, 2019

(54) SOMATIC HAPLOID HUMAN CELL LINE

(71) Applicant: HORIZON GENOMICS GMBH, Vienna (AT)

(72) Inventor: Tilmann Buerckstuemmer, Vienna (AT)

(73) Assignee: Horizon Discovery Limited, Cambridge (GB)

( * ) Notice: Subject to any disclaimer, the term of this patent is extended or adjusted under 35 U.S.C. 154(b) by 169 days.

(21) Appl. No.: 15/100,146

(22) PCT Filed: Nov. 28, 2014

(86) PCT No.: PCT/EP2014/076029
§ 371 (c)(1),
(2) Date: May 27, 2016

(87) PCT Pub. No.: WO2015/079057
PCT Pub. Date: Jun. 4, 2015

(65) Prior Publication Data
US 2017/0002380 A1    Jan. 5, 2017

(30) Foreign Application Priority Data

| Nov. 28, 2013 | (EP) | 13194939 |
| Nov. 28, 2013 | (EP) | 13194940 |
| Aug. 19, 2014 | (EP) | 14181367 |
| Nov. 5, 2014 | (EP) | 14191914 |

(51) Int. Cl.
*C12N 15/90* (2006.01)
*C12N 5/071* (2010.01)
*C12Q 1/6813* (2018.01)

(52) U.S. Cl.
CPC ......... *C12N 15/907* (2013.01); *C12N 5/0602* (2013.01); *C12N 15/902* (2013.01); *C12Q 1/6813* (2013.01); *C12N 2800/30* (2013.01)

(58) Field of Classification Search
CPC ... C12N 15/902; C12N 15/907; C12N 5/0602
See application file for complete search history.

(56) References Cited

U.S. PATENT DOCUMENTS

2012/0190011 A1    7/2012    Brummelkamp et al.

FOREIGN PATENT DOCUMENTS

| WO | WO 2011/006145 A2 | 1/2011 |
| WO | WO 2015/079056 A1 | 6/2015 |

OTHER PUBLICATIONS

Tilmann Bürckstümmer et al.: "A reversible gene trap collection empowers haploid genetics in human cells", Nature Methods, vol. 10, No. 10, Aug. 25, 2013 (Aug. 25, 2013), pp. 965-971.
Ran F Ann et al.: "Genome engineering using the CRISPR-Cas9 system", Nature Protocols, Nature Publishing Group, GB, vol. 8, No. 11, Nov. 1, 2013 (Nov. 1, 2013), pp. 2281-2308.
Amy Donner: "Trapping human genes", Science-Business Exchange, vol. 6, No. 37, Sep. 26, 2013 (Sep. 26, 2013).
Wei C et al.: "TALEN or Cas9—rapid, efficient and specific choices for genome modifications", Journal of Genetics and Genomics, Elsevier BV, NL, vol. 40, No. 6, Jun. 20, 2013 (Jun. 20, 2013), pp. 281-289.
Jan E. Carette et al.: "Ebola virus entry requires the cholesterol transporter Niemann-Pick C1", Nature, vol. 477, No. 7364, Aug. 24, 2011 (Aug. 24, 2011), pp. 340-343.
Seung Woo Cho et al.: "Targeted genome engineering in human cells with the Cas9 RNA-guided endonuclease", Nature Biotechnology, Nature Publishing Group, New York, NY, US, vol. 31, No. 3, Mar. 1, 2013 (Mar. 1, 2013), pp. 230-232.
L. Cong et al.: "Multiplex Genome Engineering Using CRISPR-Cas Systems", Science, vol. 339, No. 6121, Feb. 15, 2013 (Feb. 15, 2013), pp. 819-823.
Prashant Mali et al.: "Cas9 as a versatile tool for engineering biology", Nature Methods, Nature Publishing Group, GB, vol. 10, No. 10, Oct. 1, 2013 (Oct. 1, 2013), pp. 957-963.
"PrecisionX Cas9 SmartNuclease™ Vector System", Aug. 29, 2013 (Aug. 29, 2013), pp. 1-17.
Anonymous: "HAP1 knockout cell lines", Jan. 1, 2014 (Jan. 1, 2014).
P. Essletzbichler et al.: "Megabase-scale deletion using CRISPR/Cas9 to generate a fully haploid human cell line", Genome Research, vol. 24, No. 12, Nov. 4, 2014 (Nov. 4, 2014), pp. 2059-2065.
Takuro Horii et al.: "Genome engineering of mammalian haploid embryonic stem cells using the Cas9/RNA system", PeerJ, Dec. 23, 2013 (Dec. 23, 2013), p. e230.
A. Xiao et al.: "Chromosomal deletions and inversions mediated by TALENs and CRISPR/Cas in zebrafish", Nucleic Acids Research, vol. 41, No. 14, Jun. 6, 2013 (Jun. 6, 2013), pp. e141-e141.
Jan E Carette et al.: "Global gene disruption in human cells to assign genes to phenotypes by deep sequencing", Nature Biotechnology, vol. 29, No. 6, May 29, 2011 (May 29, 2011), pp. 542-546.
International Search Report for International Application No. PCT/EP2014/076029 dated Jul. 13, 2015, (5 pages).

(Continued)

*Primary Examiner* — Antonio Galisteo Gonzalez
(74) *Attorney, Agent, or Firm* — Bookoff McAndrews, PLLC

(57) ABSTRACT

The invention provides for a somatic fully haploid, karyotypically stable human cell line, e.g. obtainable by targeted deletion of one or more disomic chromosomal regions of a somatic near-haploid human parental cell, a method of producing the same, as well as the use of the cell line for producing isogenic cell variants, comprising genomic mutations at different genomic target sites, and a library of such cell variants.

Figure 6:
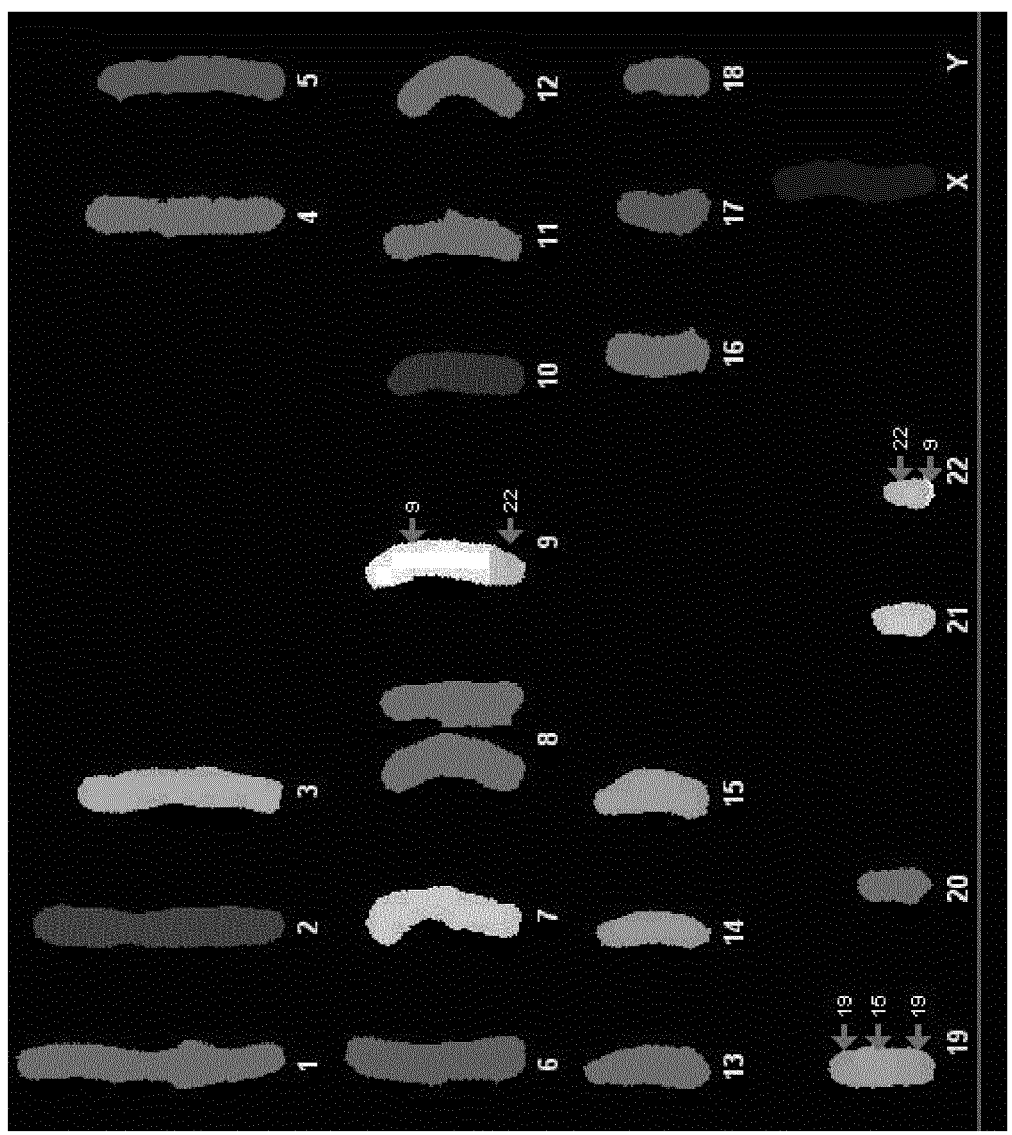

2 Claims, 33 Drawing Sheets
Specification includes a Sequence Listing.

(56) References Cited

OTHER PUBLICATIONS

International Search Report for International Application No. PCT/EP2014/076028 dated Mar. 13, 2015 (5 pages).
Carette, J. et al., "Haploid Genetic Screens in Human Cells Identify Host Factors Used by Pathogens," *Science*, vol. 326, pp. 1231-1235 (2009).

Fig. 1:

1.A)

Streptococcus Pyogenes CAS9, NC_002737, SEQ ID 1:

MDKKYSIGLDIGTNSVGWAVITDEYKVPSKKFKVLGNTDRHSIKKNLIGALLFDSGETAEATRLKRTARRRYTRRKNRIC
YLQEIFSNEMAKVDDSFFHRLEESFLVEEDKKHERHPIFGNIVDEVAYHEKYPTIYHLRKKLVDSTDKADLRLIYLALAHM
IKFRGHFLIEGDLNPDNSDVDKLFIQLVQTYNQLFEENPINASGVDAKAILSARLSKSRRLENLIAQLPGEKKNGLFGNLI
ALSLGLTPNFKSNFDLAEDAKLQLSKDTYDDDLDNLLAQIGDQYADLFLAAKNLSDAILLSDILRVNTEITKAPLSASMIK
RYDEHHQDLTLLKALVRQQLPEKYKEIFFDQSKNGYAGYIDGGASQEEFYKFIKPILEKMDGTEELLVKLNREDLLRKQR
TFDNGSIPHQIHLGELHAILRRQEDFYPFLKDNREKIEKILTFRIPYYVGPLARGNSRFAWMTRKSEETITPWNFEEVVD
KGASAQSFIERMTNFDKNLPNEKVLPKHSLLYEYFTVYNELTKVKYVTEGMRKPAFLSGEQKKAIVDLLFKTNRKVTVK
QLKEDYFKKIECFDSVEISGVEDRFNASLGTYHDLLKIIKDKDFLDNEENEDILEDIVLTLTLFEDREMIEERLKTYAHLFDD
KVMKQLKRRRYTGWGRLSRKLINGIRDKQSGKTILDFLKSDGFANRNFMQLIHDDSLTFKEDIQKAQVSGQGDSLHE
HIANLAGSPAIKKGILQTVKVVDELVKVMGRHKPENIVIEMARENQTTQKGQKNSRERMKRIEEGIKELGSQILKEHPV
ENTQLQNEKLYLYYLQNGRDMYVDQELDINRLSDYDVDHIVPQSFLKDDSIDNKVLTRSDKNRGKSDNVPSEEVVKK
MKNYWRQLLNAKLITQRKFDNLTKAERGGLSELDKAGFIKRQLVETRQITKHVAQILDSRMNTKYDENDKLIREVKVIT
LKSKLVSDFRKDFQFYKVREINNYHHAHDAYLNAVVGTALIKKYPKLESEFVYGDYKVYDVRKMIAKSEQEIGKATAKYF
FYSNIMNFFKTEITLANGEIRKRPLIETNGETGEIVWDKGRDFATVRKVLSMPQVNIVKKTEVQTGGFSKESILPKRNSD
KLIARKKDWDPKKYGGFDSPTVAYSVLVVAKVEKGKSKKLKSVKELLGITIMERSSFEKNPIDFLEAKGYKEVKKDLIIKLP
KYSLFELENGRKRMLASAGELQKGNELALPSKYVNFLYLASHYEKLKGSPEDNEQKQLFVEQHKHYLDEIIEQISEFSKR
VILADANLDKVLSAYNKHRDKPIREQAENIIHLFTLTNLGAPAAFKYFDTTIDRKRYTSTKEVLDATLIHQSITGLYETRIDL
SQLGGD

Protospacer Adjacent Motif (PAM), SEQ ID 2: NGG, wherein N= any of T, C, A or G

Chimeric guide RNA, SEQ ID 3: 20 variable bases (N= any of U, C, A or G) followed by the constant part of guide RNA (SEQ ID 4), including the constant part of crRNA, a linker and the tracrRNA; the 3' terminal part of SEQ ID 4 is variable.

NNNNNNNNNNNNNNNNNNNNGUUUUAGAGCUAGAAAUAGCAAGUUAAAAUAAGGCUAGUCCGUUAUCA
ACUUGAAAAAGUGGCACCGAGUCGGUGC

1.B)

***Streptococcus Pyogenes* CAS9, NC_002737 with N-terminal Nuclear Localization Signal, SEQ ID 5:**
N-terminal extension: *italic*
Nuclear Localization Signal: bold; *PKKKRKV* (SEQ ID 6)

*M**PKKKRKV**GS*MDKKYSIGLDIGTNSVGWAVITDEYKVPSKKFKVLGNTDRHSIKKNLIGALLFDSGETAEATRLKRTAR
RRYTRRKNRICYLQEIFSNEMAKVDDSFFHRLEESFLVEEDKKHERHPIFGNIVDEVAYHEKYPTIYHLRKKLVDSTDKAD
LRLIYLALAHMIKFRGHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKNLSDAILLSDILRVNTEI
TKAPLSASMIKRYDEHHQDLTLLKALVRQQLPEKYKEIFFDQSKNGYAGYIDGGASQEEFYKFIKPILEKMDGTEELLVKL
NREDLLRKQRTFDNGSIPHQIHLGELHAILRRQEDFYPFLKDNREKIEKILTFRIPYYVGPLARGNSRFAWMTRKSEETIT
PWNFEEVVDKGASAQSFIERMTNFDKNLPNEKVLPKHSLLYEYFTVYNELTKVKYVTEGMRKPAFLSGEQKKAIVDLLF
KTNRKVTVKQLKEDYFKKIECFDSVEISGVEDRFNASLGTYHDLLKIIKDKDFLDNEENEDILEDIVLTLTLFEDREMIEERL
KTYAHLFDDKVMKQLKRRRYTGWGRLSRKLINGIRDKQSGKTILDFLKSDGFANRNFMQLIHDDSLTFKEDIQKAQVS
GQGDSLHEHIANLAGSPAIKKGILQTVKVVDELVKVMGRHKPENIVIEMARENQTTQKGQKNSRERMKRIEEGIKELG
SQILKEHPVENTQLQNEKLYLYYLQNGRDMYVDQELDINRLSDYDVDHIVPQSFLKDDSIDNKVLTRSDKNRGKSDNV
PSEEVVKKMKNYWRQLLNAKLITQRKFDNLTKAERGGLSELDKAGFIKRQLVETRQITKHVAQILDSRMNTKYDENDK
LIREVKVITLKSKLVSDFRKDFQFYKVREINNYHHAHDAYLNAVVGTALIKKYPKLESEFVYGDYKVYDVRKMIAKSEQEI
GKATAKYFFYSNIMNFFKTEITLANGEIRKRPLIETNGETGEIVWDKGRDFATVRKVLSMPQVNIVKKTEVQTGGFSKE
SILPKRNSDKLIARKKDWDPKKYGGFDSPTVAYSVLVVAKVEKGKSKKLKSVKELLGITIMERSSFEKNPIDFLEAKGYKE
VKKDLIIKLPKYSLFELENGRKRMLASAGELQKGNELALPSKYVNFLYLASHYEKLKGSPEDNEQKQLFVEQHKHYLDEII
EQISEFSKRVILADANLDKVLSAYNKHRDKPIREQAENIIHLFTLTNLGAPAAFKYFDTTIDRKRYTSTKEVLDATLIHQSIT
GLYETRIDLSQLGGD

1.C)

*Streptococcus Pyogenes* CAS9, NC_002737 with C-terminal Nuclear Localization Signal, SEQ ID 7:

C-terminal extension: *italic*

Nuclear Localization Signal: bold

MDKKYSIGLDIGTNSVGWAVITDEYKVPSKKFKVLGNTDRHSIKKNLIGALLFDSGETAEATRLKRTARRRYTRRKNRIC
YLQEIFSNEMAKVDDSFFHRLEESFLVEEDKKHERHPIFGNIVDEVAYHEKYPTIYHLRKKLVDSTDKADLRLIYLALAHM
IKFRGHFLIEGDLNPDNSDVDKLFIQLVQTYNQLFEENPINASGVDAKAILSARLSKSRRLENLIAQLPGEKKNGLFGNLI
ALSLGLTPNFKSNFDLAEDAKLQLSKDTYDDDLDNLLAQIGDQYADLFLAAKNLSDAILLSDILRVNTEITKAPLSASMIK
RYDEHHQDLTLLKALVRQQLPEKYKEIFFDQSKNGYAGYIDGGASQEEFYKFIKPILEKMDGTEELLVKLNREDLLRKQR
TFDNGSIPHQIHLGELHAILRRQEDFYPFLKDNREKIEKILTFRIPYYVGPLARGNSRFAWMTRKSEETITPWNFEEVVD
KGASAQSFIERMTNFDKNLPNEKVLPKHSLLYEYFTVYNELTKVKYVTEGMRKPAFLSGEQKKAIVDLLFKTNRKVTVK
QLKEDYFKKIECFDSVEISGVEDRFNASLGTYHDLLKIIKDKDFLDNEENEDILEDIVLTLTLFEDREMIEERLKTYAHLFDD
KVMKQLKRRRYTGWGRLSRKLINGIRDKQSGKTILDFLKSDGFANRNFMQLIHDDSLTFKEDIQKAQVSGQGDSLHE
HIANLAGSPAIKKGILQTVKVVDELVKVMGRHKPENIVIEMARENQTTQKGQKNSRERMKRIEEGIKELGSQILKEHPV
ENTQLQNEKLYLYYLQNGRDMYVDQELDINRLSDYDVDHIVPQSFLKDDSIDNKVLTRSDKNRGKSDNVPSEEVVKK
MKNYWRQLLNAKLITQRKFDNLTKAERGGLSELDKAGFIKRQLVETRQITKHVAQILDSRMNTKYDENDKLIREVKVIT
LKSKLVSDFRKDFQFYKVREINNYHHAHDAYLNAVVGTALIKKYPKLESEFVYGDYKVYDVRKMIAKSEQEIGKATAKYF
FYSNIMNFFKTEITLANGEIRKRPLIETNGETGEIVWDKGRDFATVRKVLSMPQVNIVKKTEVQTGGFSKESILPKRNSD
KLIARKKDWDPKKYGGFDSPTVAYSVLVVAKVEKGKSKKLKSVKELLGITIMERSSFEKNPIDFLEAKGYKEVKKDLIIKLP
KYSLFELENGRKRMLASAGELQKGNELALPSKYVNFLYLASHYEKLKGSPEDNEQKQLFVEQHKHYLDEIIEQISEFSKR
VILADANLDKVLSAYNKHRDKPIREQAENIIHLFTLTNLGAPAAFKYFDTTIDRKRYTSTKEVLDATLIHQSITGLYETRIDL
SQLGGD*GS*PKKKRKV*

*Streptococcus Pyogenes* CAS9, NC_002737 with N- and C-terminal Nuclear Localization Signal, SEQ ID 8:

terminal extension: *italic*

Nuclear Localization Signal: bold

*MPKKKRKVGS*MDKKYSIGLDIGTNSVGWAVITDEYKVPSKKFKVLGNTDRHSIKKNLIGALLFDSGETAEATRLKRTAR RRYTRRKNRICYLQEIFSNEMAKVDDSFFHRLEESFLVEEDKKHERHPIFGNIVDEVAYHEKYPTIYHLRKKLVDSTDKAD LRLIYLALAHMIKFRGHFLIEGDLNPDNSDVDKLFIQLVQTYNQLFEENPINASGVDAKAILSARLSKSRRLENLIAQLPG EKKNGLFGNLIALSLGLTPNFKSNFDLAEDAKLQLSKDTYDDDLDNLLAQIGDQYADLFLAAKNLSDAILLSDILRVNTEI TKAPLSASMIKRYDEHHQDLTLLKALVRQQLPEKYKEIFFDQSKNGYAGYIDGGASQEEFYKFIKPILEKMDGTEELLVKL NREDLLRKQRTFDNGSIPHQIHLGELHAILRRQEDFYPFLKDNREKIEKILTFRIPYYVGPLARGNSRFAWMTRKSEETIT PWNFEEVVDKGASAQSFIERMTNFDKNLPNEKVLPKHSLLYEYFTVYNELTKVKYVTEGMRKPAFLSGEQKKAIVDLLF KTNRKVTVKQLKEDYFKKIECFDSVEISGVEDRFNASLGTYHDLLKIIKDKDFLDNEENEDILEDIVLTLTLFEDREMIEERL KTYAHLFDDKVMKQLKRRRYTGWGRLSRKLINGIRDKQSGKTILDFLKSDGFANRNFMQLIHDDSLTFKEDIQKAQVS GQGDSLHEHIANLAGSPAIKKGILQTVKVVDELVKVMGRHKPENIVIEMARENQTTQKGQKNSRERMKRIEEGIKELG SQILKEHPVENTQLQNEKLYLYYLQNGRDMYVDQELDINRLSDYDVDHIVPQSFLKDDSIDNKVLTRSDKNRGKSDNV PSEEVVKKMKNYWRQLLNAKLITQRKFDNLTKAERGGLSELDKAGFIKRQLVETRQITKHVAQILDSRMNTKYDENDK LIREVKVITLKSKLVSDFRKDFQFYKVREINNYHHAHDAYLNAVVGTALIKKYPKLESEFVYGDYKVYDVRKMIAKSEQEI GKATAKYFFYSNIMNFFKTEITLANGEIRKRPLIETNGETGEIVWDKGRDFATVRKVLSMPQVNIVKKTEVQTGGFSKE SILPKRNSDKLIARKKDWDPKKYGGFDSPTVAYSVLVVAKVEKGKSKKLKSVKELLGITIMERSSFEKNPIDFLEAKGYKE VKKDLIIKLPKYSLFELENGRKRMLASAGELQKGNELALPSKYVNFLYLASHYEKLKGSPEDNEQKQLFVEQHKHYLDEII EQISEFSKRVILADANLDKVLSAYNKHRDKPIREQAENIIHLFTLTNLGAPAAFKYFDTTIDRKRYTSTKEVLDATLIHQSIT GLYETRIDLSQLGGD*GSPKKKRKV*

1.E)

*Streptococcus Pyogenes* CAS9, NC_002737 with N-terminal Nuclear Localization Signal from SV40 Large T Antigen and C-terminal Nuclear Localization Signal from Nucleoplasmin
SEQ ID 9:

terminal extensions: *italic*
Nuclear Localization Signal: bold

*MDYKDHDGDYKDHDIDYKDDDDKMA*PKKKRKV*GIHGVPAA*DKKYSIGLDIGTNSVGWAVITDEYKVPSKKFKVLGN
TDRHSIKKNLIGALLFDSGETAEATRLKRTARRRYTRRKNRICYLQEIFSNEMAKVDDSFFHRLEESFLVEEDKKHERHPI
FGNIVDEVAYHEKYPTIYHLRKKLVDSTDKADLRLIYLALAHMIKFRGHFLIEGDLNPDNSDVDKLFIQLVQTYNQLFEE
NPINASGVDAKAILSARLSKSRRLENLIAQLPGEKKNGLFGNLIALSLGLTPNFKSNFDLAEDAKLQLSKDTYDDDLDNLL
AQIGDQYADLFLAAKNLSDAILLSDILRVNTEITKAPLSASMIKRYDEHHQDLTLLKALVRQQLPEKYKEIFFDQSKNGYA
GYIDGGASQEEFYKFIKPILEKMDGTEELLVKLNREDLLRKQRTFDNGSIPHQIHLGELHAILRRQEDFYPFLKDNREKIE
KILTFRIPYYVGPLARGNSRFAWMTRKSEETITPWNFEEVVDKGASAQSFIERMTNFDKNLPNEKVLPKHSLLYEYFTV
YNELTKVKYVTEGMRKPAFLSGEQKKAIVDLLFKTNRKVTVKQLKEDYFKKIECFDSVEISGVEDRFNASLGTYHDLLKII
KDKDFLDNEENEDILEDIVLTLTLFEDREMIEERLKTYAHLFDDKVMKQLKRRRYTGWGRLSRKLINGIRDKQSGKTILD
FLKSDGFANRNFMQLIHDDSLTFKEDIQKAQVSGQGDSLHEHIANLAGSPAIKKGILQTVKVVDELVKVMGRHKPENI
VIEMARENQTTQKGQKNSRERMKRIEEGIKELGSQILKEHPVENTQLQNEKLYLYYLQNGRDMYVDQELDINRLSDYD
VDHIVPQSFLKDDSIDNKVLTRSDKNRGKSDNVPSEEVVKKMKNYWRQLLNAKLITQRKFDNLTKAERGGLSELDKA
GFIKRQLVETRQITKHVAQILDSRMNTKYDENDKLIREVKVITLKSKLVSDFRKDFQFYKVREINNYHHAHDAYLNAVV
GTALIKKYPKLESEFVYGDYKVYDVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKG
KSKKLKSVKELLGITIMERSSFEKNPIDFLEAKGYKEVKKDLIIKLPKYSLFELENGRKRMLASAGELQKGNELALPSKYVN
FLYLASHYEKLKGSPEDNEQKQLFVEQHKHYLDEIIEQISEFSKRVILADANLDKVLSAYNKHRDKPIREQAENIIHLFTLT
NLGAPAAFKYFDTTIDRKRYTSTKEVLDATLIHQSITGLYETRIDLSQLGGD*KRPAATKKAGQAKKKK*

Fig. 2:

2.A)

*Streptococcus Thermophilus* CAS9, YP_820161, SEQ ID 10:

MSDLVLGLDIGIGSVGVGILNKVTGEIIHKNSRIFPAAQAENNLVRRTNRQGRRLARRKKHRRVRLNRLFEESGLITDFT
KISINLNPYQLRVKGLTDELSNEELFIALKNMVKHRGISYLDDASDDGNSSVGDYAQIVKENSKQLETKTPGQIQLERYQ
TYGQLRGDFTVEKDGKKHRLINVFPTSAYRSEALRILQTQQEFNPQITDEFINRYLEILTGKRKYYHGPGNEKSRTDYGR
YRTSGETLDNIFGILIGKCTFYPDEFRAAKASYTAQEFNLLNDLNNLTVPTETKKLSKEQKNQIINYVKNEKAMGPAKLFK
YIAKLLSCDVADIKGYRIDKSGKAEIHTFEAYRKMKTLETLDIEQMDRETLDKLAYVLTLNTEREGIQEALEHEFADGSFS
QKQVDELVQFRKANSSIFGKGWHNFSVKLMMELIPELYETSEEQMTILTRLGKQKTTSSSNKTKYIDEKLLTEEIYNPVV
AKSVRQAIKIVNAAIKEYGDFDNIVIEMARETNEDDEKKAIQKIQKANKDEKDAAMLKAANQYNGKAELPHSVFHGH
KQLATKIRLWHQQGERCLYTGKTISIHDLINNSNQFEVDHILPLSITFDDSLANKVLVYATANQEKGQRTPYQALDSMD
DAWSFRELKAFVRESKTLSNKKKEYLLTEEDISKFDVRKKFIERNLVDTRYASRVVLNALQEHFRAHKIDTKVSVVRGQF
TSQLRRHWGIEKTRDTYHHHAVDALIIAASSQLNLWKKQKNTLVSYSEDQLLDIETGELISDDEYKESVFKAPYQHFVD
TLKSKEFEDSILFSYQVDSKFNRKISDATIYATRQAKVGKDKADETYVLGKIKDIYTQDGYDAFMKIYKKDKSKFLMYRH
DPQTFEKVIEPILENYPNKQINDKGKEVPCNPFLKYKEEHGYIRKYSKKGNGPEIKSLKYYDSKLGNHIDITPKDSNNKVV
LQSVSPWRADVYFNKTTGKYEILGLKYADLQFDKGTGTYKISQEKYNDIKKKEGVDSDSEFKFTLYKNDLLLVKDTETKE
QQLFRFLSRTMPKQKHYVELKPYDKQKFEGGEALIKVLGNVANSGQCKKGLGKSNISIYKVRTDVLGNQHIIKNEGDK
PKLDF

Protospacer Adjacent Motif (PAM), SEQ ID 11: NN(A/G)G(A/G)A, wherein N= any of T, C, A or G (e.g. NNAGAA(A/T), SEQ ID 12)

Chimeric guide RNA, SEQ ID 13: 20 variable bases (N= any of U, C, A or G) followed by the constant part of guide RNA (SEQ ID 14), including the constant part of crRNA, a linker and the tracrRNA; the 3' terminal part of SEQ ID 14 is variable:

NNNNNNNNNNNNNNNNNNNNGUUUUUGUACUCUCAAGAUUUAAGUAACUGUACAACGAAACUUACACA
GUUACUUAAAUCUUGCAGAAGCUACAAAGAUAAGGCUUCAUGCCGAAAUCAACACCCUGUCAUUUUAUGG
CAGGGUGUUUUUUU

2.B)

*Streptococcus Thermophilus* CAS9, YP_820161, fused to 3x C-terminal NLS, SEQ ID 15:

terminal extension: *italic*

Nuclear Localization Signal (NLS): bold

MSDLVLGLDIGIGSVGVGILNKVTGEIIHKNSRIFPAAQAENNLVRRTNRQGRRLARRKKHRRVRLNRLFEESGLITDFT
KISINLNPYQLRVKGLTDELSNEELFIALKNMVKHRGISYLDDASDDGNSSVGDYAQIVKENSKQLETKTPGQIQLERYQ
TYGQLRGDFTVEKDGKKHRLINVFPTSAYRSEALRILQTQQEFNPQITDEFINRYLEILTGKRKYYHGPGNEKSRTDYGR
YRTSGETLDNIFGILIGKCTFYPDEFRAAKASYTAQEFNLLNDLNNLTVPTETKKLSKEQKNQIINYVKNEKAMGPAKLFK
YIAKLLSCDVADIKGYRIDKSGKAEIHTFEAYRKMKTLETLDIEQMDRETLDKLAYVLTLNTEREGIQEALEHEFADGSFS
QKQVDELVQFRKANSSIFGKGWHNFSVKLMMELIPELYETSEEQMTILTRLGKQKTTSSSNKTKYIDEKLLTEEIYNPVV
AKSVRQAIKIVNAAIKEYGDFDNIVIEMARETNEDDEKKAIQKIQKANKDEKDAAMLKAANQYNGKAELPHSVFHGH
KQLATKIRLWHQQGERCLYTGKTISIHDLINNSNQFEVDHILPLSITFDDSLANKVLVYATANQEKGQRTPYQALDSMD
DAWSFRELKAFVRESKTLSNKKKEYLLTEEDISKFDVRKKFIERNLVDTRYASRVVLNALQEHFRAHKIDTKVSVVRGQF
TSQLRRHWGIEKTRDTYHHHAVDALIIAASSQLNLWKKQKNTLVSYSEDQLLDIETGELISDDEYKESVFKAPYQHFVD
TLKSKEFEDSILFSYQVDSKFNRKISDATIYATRQAKVGKDKADETYVLGKIKDIYTQDGYDAFMKIYKKDKSKFLMYRH
DPQTFEKVIEPILENYPNKQINDKGKEVPCNPFLKYKEEHGYIRKYSKKGNGPEIKSLKYYDSKLGNHIDITPKDSNNKVV
LQSVSPWRADVYFNKTTGKYEILGLKYADLQFDKGTGTYKISQEKYNDIKKKEGVDSDSEFKFTLYKNDLLLVKDTETKE
QQLFRFLSRTMPKQKHYVELKPYDKQKFEGGEALIKVLGNVANSGQCKKGLGKSNISIYKVRTDVLGNQHIIKNEGDK
PKLDF*AAAD*PKKKRKVDPKKKRKVDPKKKRKV*DTAA*

Fig. 3:

3.A)

*Neisseria Meningitis* CAS9, YP_002342100, SEQ ID 16:

MAAFKPNPINYILGLDIGIASVGWAMVEIDEDENPICLIDLGVRVFERAEVPKTGDSLAMARRLARSVRRLTRRRAHRL
LRARRLLKREGVLQAADFDENGLIKSLPNTPWQLRAAALDRKLTPLEWSAVLLHLIKHRGYLSQRKNEGETADKELGAL
LKGVADNAHALQTGDFRTPAELALNKFEKESGHIRNQRGDYSHTFSRKDLQAELILLFEKQKEFGNPHVSGGLKEGIET
LLMTQRPALSGDAVQKMLGHCTFEPAEPKAAKNTYTAERFIWLTKLNNLRILEQGSERPLTDTERATLMDEPYRKSKL
TYAQARKLLGLEDTAFFKGLRYGKDNAEASTLMEMKAYHAISRALEKEGLKDKKSPLNLSPELQDEIGTAFSLFKTDEDI
TGRLKDRIQPEILEALLKHISFDKFVQISLKALRRIVPLMEQGKRYDEACAEIYGDHYGKKNTEEKIYLPPIPADEIRNPVVL
RALSQARKVINGVVRRYGSPARIHIETAREVGKSFKDRKEIEKRQEENRKDREKAAAKFREYFPNFVGEPKSKDILKLRLY
EQQHGKCLYSGKEINLGRLNEKGYVEIDHALPFSRTWDDSFNNKVLVLGSENQNKGNQTPYEYFNGKDNSREWQEF
KARVETSRFPRSKKQRILLQKFDEDGFKERNLNDTRYVNRFLCFVADRMRLTGKGKKRVFASNGQITNLLRGFWGLRK
VRAENDRHHALDAVVVACSTVAMQQKITRFVRYKEMNAFDGKTIDKETGEVLHQKTHFPQPWEFFAQEVMIRVFG
KPDGKPEFEEADTPEKLRTLLAEKLSSRPEAVHEYVTPLFVSRAPNRKMSGQGHMETVKSAKRLDEGVSVLRVPLTQLK
LKDLEKMVNREREPKLYEALKARLEAHKDDPAKAFAEPFYKYDKAGNRTQQVKAVRVEQVQKTGVWVRNHNGIAD
NATMVRVDVFEKGDKYYLVPIYSWQVAKGILPDRAVVQGKDEEDWQLIDDSFNFKFSLHPNDLVEVITKKARMFGYF
ASCHRGTGNINIRIHDLDHKIGKNGILEGIGVKTALSFQKYQIDELGKEIRPCRLKKRPPVR

Protospacer Adjacent Motif (PAM), NNNNGANN (SEQ ID 17), or NNNNGTTN (SEQ ID 75) or NNNNGNNT (SEQ ID 76), wherein N= any of T, C, A or G (e.g. NNNNGATT, wherein N= any of T, C, A or G (SEQ ID 18))

Chimeric guide RNA, SEQ ID 19: 24 variable bases (N= any of U, C, A or G) followed by the constant part of guide RNA (SEQ ID 20), including the constant part of crRNA, a linker and the tracrRNA; the 3' terminal part of SEQ ID 20 is variable:

NNNNNNNNNNNNNNNNNNNNNNNNGUUGUAGCUCCCUUUCUCAUUUGGGAAACGAAAUGAGAACCGUU
GCUACAAUAAGGCCGUCUGAAAAGAUGUGCCGCAACGCUCUGCCCCUUAAAGCUUCUGCUUUAAGGGGCA
UCGUUUA

3.B)

*Neisseria Meningitis* CAS9, YP_002342100, fused to 3x C-terminal NLS, SEQ ID 21:

terminal extension: *italic*

Nuclear Localization Signal (NLS): bold

MAAFKPNPINYILGLDIGIASVGWAMVEIDEDENPICLIDLGVRVFERAEVPKTGDSLAMARRLARSVRRLTRRRAHRL
LRARRLLKREGVLQAADFDENGLIKSLPNTPWQLRAAALDRKLTPLEWSAVLLHLIKHRGYLSQRKNEGETADKELGAL
LKGVADNAHALQTGDFRTPAELALNKFEKESGHIRNQRGDYSHTFSRKDLQAELILLFEKQKEFGNPHVSGGLKEGIET
LLMTQRPALSGDAVQKMLGHCTFEPAEPKAAKNTYTAERFIWLTKLNNLRILEQGSERPLTDTERATLMDEPYRKSKL
TYAQARKLLGLEDTAFFKGLRYGKDNAEASTLMEMKAYHAISRALEKEGLKDKKSPLNLSPELQDEIGTAFSLFKTDEDI
TGRLKDRIQPEILEALLKHISFDKFVQISLKALRRIVPLMEQGKRYDEACAEIYGDHYGKKNTEEKIYLPPIPADEIRNPVVL
RALSQARKVINGVVRRYGSPARIHIETAREVGKSFKDRKEIEKRQEENRKDREKAAAKFREYFPNFVGEPKSKDILKLRLY
EQQHGKCLYSGKEINLGRLNEKGYVEIDHALPFSRTWDDSFNNKVLVLGSENQNKGNQTPYEYFNGKDNSREWQEF
KARVETSRFPRSKKQRILLQKFDEDGFKERNLNDTRYVNRFLCQFVADRMRLTGKGKKRVFASNGQITNLLRGFWGLR
KVRAENDRHHALDAVVVACSTVAMQQKITRFVRYKEMNAFDGKTIDKETGEVLHQKTHFPQPWEFFAQEVMIRVF
GKPDGKPEFEEADTPEKLRTLLAEKLSSRPEAVHEYVTPLFVSRAPNRKMSGQGHMETVKSAKRLDEGVSVLRVPLTQ
LKLKDLEKMVNREREPKLYEALKARLEAHKDDPAKAFAEPFYKYDKAGNRTQQVKAVRVEQVQKTGVWVRNHNGIA
DNATMVRVDVFEKGDKYYLVPIYSWQVAKGILPDRAVVQGKDEEDWQLIDDSFNFKFSLHPNDLVEVITKKARMFG
YFASCHRGTGNINIRIHDLDHKIGKNGILEGIGVKTALSFQKYQIDELGKEIRPCRLKKRPPVR*AAAD*PKKKRKVDPKKK
*RKVDPKKKRKVDTAA*

Fig. 4:

4.A)

*Treponema Denticola* Cas9, NP_970941, SEQ ID 22:

MKKEIKDYFLGLDVGTGSVGWAVTDTDYKLLKANRKDLWGMRCFETAETAEVRRLHRGARRRIERRKKRIKLLQELFS
QEIAKTDEGFFQRMKESPFYAEDKTILQENTLFNDKDFADKTYHKAYPTINHLIKAWIENKVKPDPRLLYLACHNIIKKR
GHFLFEGDFDSENQFDTSIQALFEYLREDMEVDIDADSQKVKEILKDSSLKNSEKQSRLNKILGLKPSDKQKKAITNLISG
NKINFADLYDNPDLKDAEKNSISFSKDDFDALSDDLASILGDSFELLLKAKAVYNCSVLSKVIGDEQYLSFAKVKIYEKHKT
DLTKLKNVIKKHFPKDYKKVFGYNKNEKNNNNYSGYVGVCKTKSKKLIINNSVNQEDFYKFLKTILSAKSEIKEVNDILTEI
ETGTFLPKQISKSNAEIPYQLRKMELEKILSNAEKHFSFLKQKDEKGLSHSEKIIMLLTFKIPYYIGPINDNHKKFFPDRCW
VVKKEKSPSGKTTPWNFFDHIDKEKTAEAFITSRTNFCTYLVGESVLPKSSLLYSEYTVLNEINNLQIIIDGKNICDIKLKQK
IYEDLFKKYKKITQKQISTFIKHEGICNKTDEVIILGIDKECTSSLKSYIELKNIFGKQVDEISTKNMLEEIIRWATIYDEGEGK
TILKTKIKAEYGKYCSDEQIKKILNLKFSGWGRLSRKFLETVTSEMPGFSEPVNIITAMRETQNNLMELLSSEFTFTENIKK
INSGFEDAEKQFSYDGLVKPLFLSPSVKKMLWQTLKLVKEISHITQAPPKKIFIEMAKGAELEPARTKTRLKILQDLYNNC
KNDADAFSSEIKDLSGKIENEDNLRLRSDKLYLYYTQLGKCMYCGKPIEIGHVFDTSNYDIDHIYPQSKIKDDSISNRVLV
CSSCNKNKEDKYPLKSEIQSKQRGFWNFLQRNNFISLEKLNRLTRATPISDDETAKFIARQLVETRQATKVAAKVLEKM
FPETKIVYSKAETVSMFRNKFDIVKCREINDFHHAHDAYLNIVVGNVYNTKFTNNPWNFIKEKRDNPKIADTYNYYKVF
DYDVKRNNITAWEKGKTIITVKDMLKRNTPIYTRQAACKKGELFNQTIMKKGLGQHPLKKEGPFSNISKYGGYNKVSA
AYYTLIEYEEKGNKIRSLETIPLYLVKDIQKDQDVLKSYLTDLLGKKEFKILVPKIKINSLLKINGFPCHITGKTNDSFLLRPAV
QFCCSNNEVLYFKKIIRFSEIRSQREKIGKTISPYEDLSFRSYIKENLWKKTKNDEIGEKEFYDLLQKKNLEIYDMLLTKHKD
TIYKKRPNSATIDILVKGKEKFKSLIIENQFEVILEILKLFSATRNVSDLQHIGGSKYSGVAKIGNKISSLDNCILIYQSITGIFE
KRIDLLKV

Protospacer Adjacent Motif (PAM), SEQ ID 23: NAAAAN, wherein N= any of T, C, A or G

4.B)

*Treponema Denticola* Cas9, NP_970941, with 3x C-terminal NLS, SEQ ID 24:

terminal extension: *italic*

Nuclear Localization Signal (NLS): bold

MKKEIKDYFLGLDVGTGSVGWAVTDTDYKLLKANRKDLWGMRCFETAETAEVRRLHRGARRRIERRKKRIKLLQELFS
QEIAKTDEGFFQRMKESPFYAEDKTILQENTLFNDKDFADKTYHKAYPTINHLIKAWIENKVKPDPRLLYLACHNIIKKR
GHFLFEGDFDSENQFDTSIQALFEYLREDMEVDIDADSQKVKEILKDSSLKNSEKQSRLNKILGLKPSDKQKKAITNLISG
NKINFADLYDNPDLKDAEKNSISFSKDDFDALSDDLASILGDSFELLLKAKAVYNCSVLSKVIGDEQYLSFAKVKIYEKHKT
DLTKLKNVIKKHFPKDYKKVFGYNKNEKNNNNYSGYVGVCKTKSKKLIINNSVNQEDFYKFLKTILSAKSEIKEVNDILTEI
ETGTFLPKQISKSNAEIPYQLRKMELEKILSNAEKHFSFLKQKDEKGLSHSEKIIMLLTFKIPYYIGPINDNHKKFFPDRCW
VVKKEKSPSGKTTPWNFFDHIDKEKTAEAFITSRTNFCTYLVGESVLPKSSLLYSEYTVLNEINNLQIIIDGKNICDIKLKQK
IYEDLFKKYKKITQKQISTFIKHEGICNKTDEVIILGIDKECTSSLKSYIELKNIFGKQVDEISTKNMLEEIIRWATIYDEGEGK
TILKTKIKAEYGKYCSDEQIKKILNLKFSGWGRLSRKFLETVTSEMPGFSEPVNIITAMRETQNNLMELLSSEFTFTENIKK
INSGFEDAEKQFSYDGLVKPLFLSPSVKKMLWQTLKLVKEISHITQAPPKKIFIEMAKGAELEPARTKTRLKILQDLYNNC
KNDADAFSSEIKDLSGKIENEDNLRLRSDKLYLYYTQLGKCMYCGKPIEIGHVFDTSNYDIDHIYPQSKIKDDSISNRVLV
CSSCNKNKEDKYPLKSEIQSKQRGFWNFLQRNNFISLEKLNRLTRATPISDDETAKFIARQLVETRQATKVAAKVLEKM
FPETKIVYSKAETVSMFRNKFDIVKCREINDFHHAHDAYLNIVVGNVYNTKFTNNPWNFIKEKRDNPKIADTYNYYKVF
DYDVKRNNITAWEKGKTIITVKDMLKRNTPIYTRQAACKKGELFNQTIMKKGLGQHPLKKEGPFSNISKYGGYNKVSA
AYYTLIEYEEKGNKIRSLETIPLYLVKDIQKDQDVLKSYLTDLLGKKEFKILVPKIKINSLLKINGFPCHITGKTNDSFLLRPAV
QFCCSNNEVLYFKKIIRFSEIRSQREKIGKTISPYEDLSFRSYIKENLWKKTKNDEIGEKEFYDLLQKKNLEIYDMLLTKHKD
TIYKKRPNSATIDILVKGKEKFKSLIIENQFEVILEILKLFSATRNVSDLQHIGGSKYSGVAKIGNKISSLDNCILIYQSITGIFE
KRIDLLKV*AAAD*PKKKRKV*D*PKKKRKV*D*PKKKRKV*DTAA*

Protospacer Adjacent Motif (PAM), SEQ ID 23: NAAAAN, wherein N= any of T, C, A or G

Fig. 5

Guide RNAs parent sequences and variants crRNA sequences <u>underlined</u>, crRNA variable part in bold

N=any of U, C, A or G tracrRNA sequences in *italic* other: linker (GAAA, SEQ ID 48)

**gRNA functional with *Streptococcus Pyogenes CAS9***

SP_chimera_truncated (SEQ ID 25)

<u>NNNNNNNNNNNNNNNNNNNNGUUUUAGAGCUA</u>*GAAAUAGCAAGUUAAAAUAAGGCUAGUCCGUUAUC AACUUGAAAAAGUGGCACCGAGUCGGUGCUUUUUU*

SP_chimera_full (SEQ ID 26)

<u>NNNNNNNNNNNNNNNNNNNNGUUUUAGAGCUA</u>*UGCUGUUUUGAAUGGUCCCAAAACGAAAUUGUUGG AACCAUUCAAAACAGCAUAGCAAGUUAAAAUAAGGCUAGUCCGUUAUCAACUUGAAAAAGUGGCACCGAGU CGGUGCUUUUUU*

Fig. 5 (continued)

**gRNA functional with *Streptococcus Thermophilus* CAS9**

ST_chimera_truncated (SEQ ID 27)

NNNNNNNNNNNNNNNNNNNNGUUUUUGUACUCUCAGAAAUGCAGAAGCUACAAAGAUAAGGCUUCAUG
CCGAAAUCAACACCCUGUCAUUUUAUGGCAGGGUGUU

ST_chimera_full (SEQ ID 28)

NNNNNNNNNNNNNNNNNNNNGUUUUUGUACUCUCAAGAUUUAAGUAACUGUACAACGAAACUUACACA
GUUACUUAAAUCUUGCAGAAGCUACAAAGAUAAGGCUUCAUGCCGAAAUCAACACCCUGUCAUUUUAUGG
CAGGGUGUU

ST_gRNA_mutant 1 (SEQ ID 29)

NNNNNNNNNNNNNNNNNNNNGUUUUUGUACUCUCAGAAAUGCAGAAGCUACAAAGAUAAGGCUUCAUG
CCGAAAUCAACACCCUGUCAUUUUAUGGCAGGGUGUUUUUUUU

ST_gRNA_mutant 2 (SEQ ID 30)

NNNNNNNNNNNNNNNNNNNNGUUUUAGUACUCUCAGAAAUGCAGAAGCUUCAAAGAUAAGGCUUCAUG
CCGAAAUCAACACCCUGUCAUUUUAUGGCAGGGUGUUUUUUUU

ST_gRNA_mutant 3 (SEQ ID 31)

NNNNNNNNNNNNNNNNNNNNGUUUGUGUACUCUCAGAAAUGCAGAAGCUACAAAGAUAAGGCUUCAUG
CCGAAAUCAACACCCUGUCAUUUUAUGGCAGGGUGUUUUUUUU

ST_gRNA_mutant 4 (SEQ ID 32)

NNNNNNNNNNNNNNNNNNNNGUUUAUGUACUCUCAGAAAUGCAGAAGCUACAAAGAUAAGGCUUCAUG
CCGAAAUCAACACCCUGUCAUUUUAUGGCAGGGUGUUUUUUUU

ST_gRNA_mutant 5 (SEQ ID 33)

NNNNNNNNNNNNNNNNNNNNGUUUUUGUACUCUGAAAAGAAGCUACAAAGAUAAGGCUUCAUGCCGAA
AUCAACACCCUGUCAUUUUAUGGCAGGGUGUUUUUUUU

Fig. 5 (continued)

ST_gRNA_mutant 6 (SEQ ID 34)
NNNNNNNNNNNNNNNNNNNNGUUUAGUACUCUGAAAAGAAGCUUCAAAGAUAAGGCUUCAUGCCGAA
AUCAACACCCUGUCAUUUUAUGGCAGGGUGUUUUUUU ST_gRNA_mutant 7 (SEQ ID 35)
NNNNNNNNNNNNNNNNNNNNGUUUGUGUACUCUGAAAAGAAGCUACAAAGAUAAGGCUUCAUGCCGAA
AUCAACACCCUGUCAUUUUAUGGCAGGGUGUUUUUUU ST_gRNA_mutant 8 (SEQ ID 36)
NNNNNNNNNNNNNNNNNNNNGUUUAUGUACUCUGAAAAGAAGCUACAAAGAUAAGGCUUCAUGCCGAA
AUCAACACCCUGUCAUUUUAUGGCAGGGUGUUUUUUU ST_gRNA_mutant 9 (SEQ ID 37)
NNNNNNNNNNNNNNNNNNNNGUUUUGUACUCUCAAGAUUUAAGUAACUGUACAACGAAACUUACACA
GUUACUUAAAUCUUGCAGAAGCUACAAAGAUAAGGCUUCAUGCCGAAAUCAACACCCUGUCAUUUUAUGG
CAGGGUGUUUUUUU ST_gRNA_mutant 10 (SEQ ID 38)
NNNNNNNNNNNNNNNNNNNNGUUUAGUACUCUCAAGAUUUAAGUAACUGUACAACGAAACUUACACA
GUUACUUAAAUCUUGCAGAAGCUUCAAAGAUAAGGCUUCAUGCCGAAAUCAACACCCUGUCAUUUUAUGG
CAGGGUGUUUUUUU ST_gRNA_mutant 11 (SEQ ID 39)
NNNNNNNNNNNNNNNNNNNNGUUUGUGUACUCUCAAGAUUUAAGUAACUGUACAACGAAACUUACACA
GUUACUUAAAUCUUGCAGAAGCUACAAAGAUAAGGCUUCAUGCCGAAAUCAACACCCUGUCAUUUUAUGG
CAGGGUGUUUUUUU ST_gRNA_mutant 12 (SEQ ID 40)
NNNNNNNNNNNNNNNNNNNNGUUUAUGUACUCUCAAGAUUUAAGUAACUGUACAACGAAACUUACACA
GUUACUUAAAUCUUGCAGAAGCUACAAAGAUAAGGCUUCAUGCCGAAAUCAACACCCUGUCAUUUUAUGG
CAGGGUGUUUUUUU

Fig. 5 (continued)

**gRNA functional with *Neisseria Meningitis* CAS9**

NM_chimera_truncated (SEQ ID 41)
NNNNNNNNNNNNNNNNNNNNGUUGUAGCUCCCUUUCUCGAAAGAGAACCGUUGCUACAAUAAGGCCGU
*CUGAAAAGAUGUGCCGCAACGCUCUGCCCCUUAAAGCUUCUGCUUUAAGGGGC*

NM_chimera_full (SEQ ID 42)
NNNNNNNNNNNNNNNNNNNNGUUGUAGCUCCCUUUCUC*AUUUCGCAGUGCUACAAUGAAAAUUGUCGC
ACUGCGAAAU*GAGAACCGUUGCUACAAUAAGGCCGUCUGAAAAGAUGUGCCGCAACGCUCUGCCCCUUAAA
GCUUCUGCUUUAAGGGGC*

NM_gRNA_mutant 1 (SEQ ID 43)
NNNNNNNNNNNNNNNNNNNNGUUGUAGCUCCCUUUCUCGAAAGAGAACCGUUGCUACAAUAAGGCCGU
CUGAAAAGAUGUGCCGCAACGCUCUGCCCCUUAAAGCUUCUGCUUUAACGGGCUUUUUUU NM_gRNA_mutant 2 (SEQ ID 44)
NNNNNNNNNNNNNNNNNNNNGUUGUAGCUCCCUUUCGAAAGAACCGUUGCUACAAUAAGGCCGUCUGA
AAAGAUGUGCCGCAACGCUCUGCCCCUUAAAGCUUCUGCUUUAACGGGCUUUUUUU NM_gRNA_mutant 3 (SEQ ID 45)
NNNNNNNNNNNNNNNNNNNNGUUGUAGCUCCCGAAACGUUGCUACAAUAAGGCCGUCUGAAAAGAUGU
GCCGCAACGCUCUGCCCCUUAAAGCUUCUGCUUUAACGGGCUUUUUUU NM_gRNA_mutant 4 (SEQ ID 46)
NNNNNNNNNNNNNNNNNNNNGUUGUAGCUCCCUUUCUCAUUUCGCAGUGCUACAAUGAAAAUUGUCGC
ACUGCGAAAUGAGAACCGUUGCUACAAUAAGGCCGUCUGAAAAGAUGUGCCGCAACGCUCUGCCCCUUAAA
GCUUCUGCUUUAAGGGGCUUUUUUU NM_sgRNA (SEQ ID 47)
NNNNNNNNNNNNNNNNNNNNGUUGUAGCUCCCUUUCUCAUUUCGGAAACGAAAUGAGAACCGUUGCUA
CAAUAAGGCCGUCUGAAAAGAUGUGCCGCAACGCUCUGCCCCUUAAAGCUUCUGCUUUAAGGGGCAUCGU
UUA Fig. 16
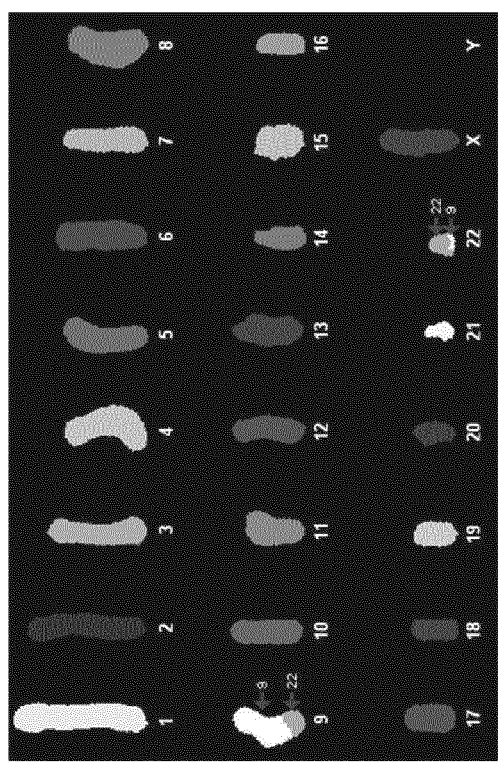
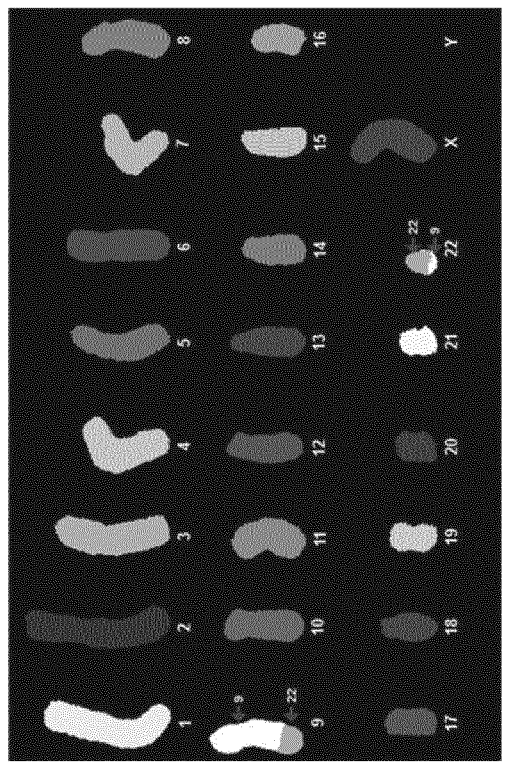
Clone A11
Clone E9

Fig. 23
(A)
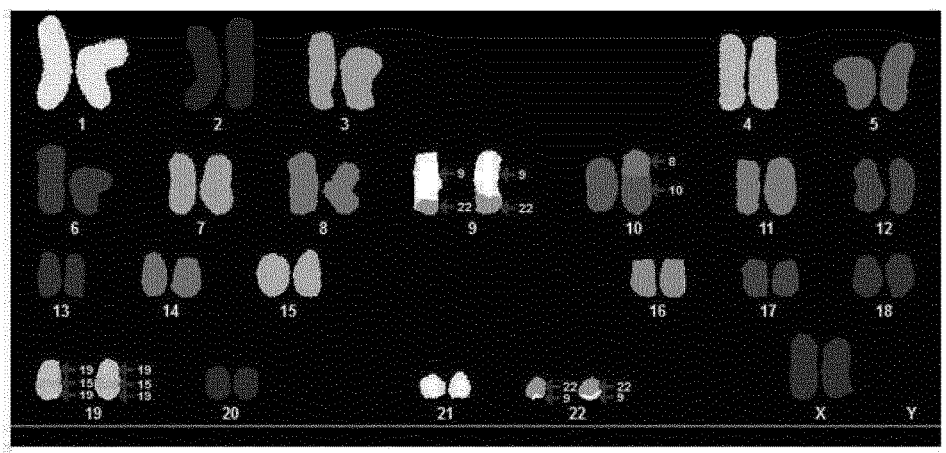
(B)
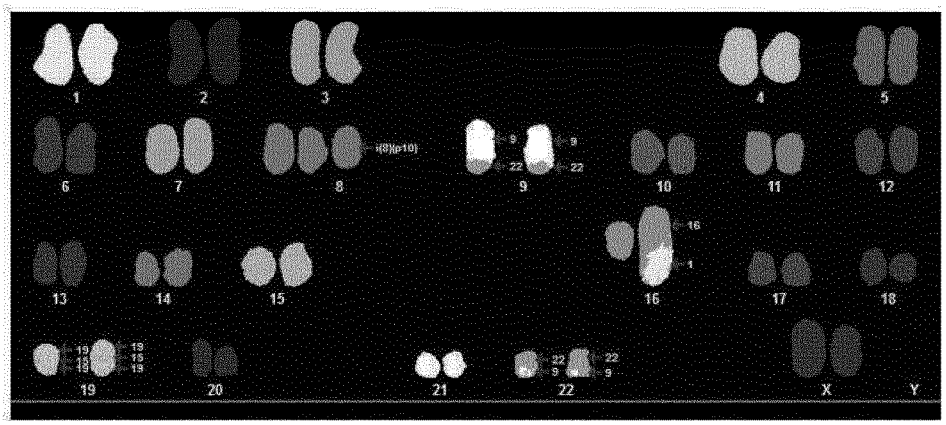
(C)
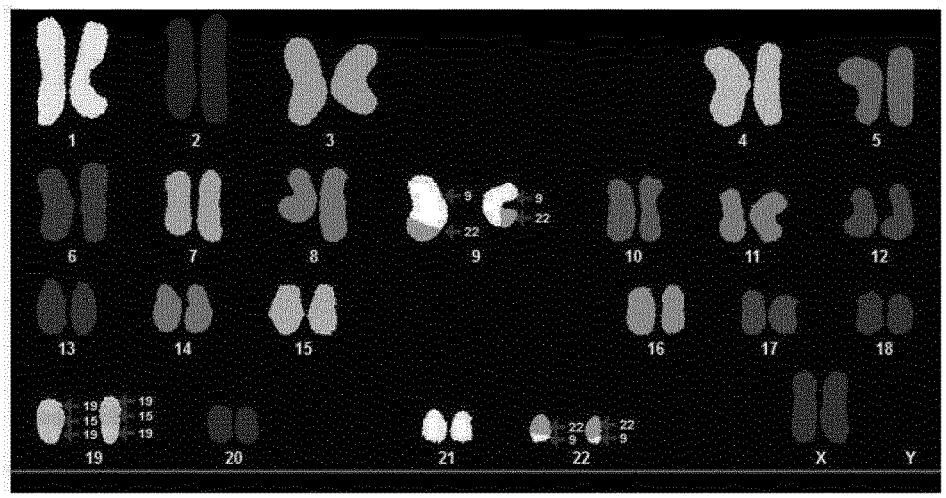

SEQUENCE LISTING

<160> NUMBER OF SEQ ID NOS: 111

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
```

-continued

```
               225                 230                 235                 240
Leu Ile Ala Leu Ser Leu Gly Leu Thr Pro Asn Phe Lys Ser Asn Phe
                   245                 250                 255

Asp Leu Ala Glu Asp Ala Lys Leu Gln Leu Ser Lys Asp Thr Tyr Asp
                   260                 265                 270

Asp Asp Leu Asp Asn Leu Leu Ala Gln Ile Gly Asp Gln Tyr Ala Asp
                   275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                    325                 330                 335

Ala Leu Val Arg Gln Gln Leu Pro Glu Lys Tyr Lys Glu Ile Phe Phe
                    340                 345                 350

Asp Gln Ser Lys Asn Gly Tyr Ala Gly Tyr Ile Asp Gly Gly Ala Ser
                    355                 360                 365

Gln Glu Glu Phe Tyr Lys Phe Ile Lys Pro Ile Leu Glu Lys Met Asp
                    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                    405                 410                 415

Gly Glu Leu His Ala Ile Leu Arg Arg Gln Glu Asp Phe Tyr Pro Phe
                    420                 425                 430

Leu Lys Asp Asn Arg Glu Lys Ile Glu Lys Ile Leu Thr Phe Arg Ile
                    435                 440                 445

Pro Tyr Tyr Val Gly Pro Leu Ala Arg Gly Asn Ser Arg Phe Ala Trp
                    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                    485                 490                 495

Asn Phe Asp Lys Asn Leu Pro Asn Glu Lys Val Leu Pro Lys His Ser
                    500                 505                 510

Leu Leu Tyr Glu Tyr Phe Thr Val Tyr Asn Glu Leu Thr Lys Val Lys
                    515                 520                 525

Tyr Val Thr Glu Gly Met Arg Lys Pro Ala Phe Leu Ser Gly Glu Gln
                    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                    565                 570                 575

Ser Val Glu Ile Ser Gly Val Glu Asp Arg Phe Asn Ala Ser Leu Gly
                    580                 585                 590

Thr Tyr His Asp Leu Leu Lys Ile Ile Lys Asp Lys Asp Phe Leu Asp
                    595                 600                 605

Asn Glu Glu Asn Glu Asp Ile Leu Glu Asp Ile Val Leu Thr Leu Thr
                    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                    645                 650                 655
```

-continued

```
Thr Gly Trp Gly Arg Leu Ser Arg Lys Leu Ile Asn Gly Ile Arg Asp
        660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
        820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065
```

-continued

Thr Gly Glu Ile Val Trp Asp Lys Gly Arg Asp Phe Ala Thr Val
1070             1075                 1080

Arg Lys Val Leu Ser Met Pro Gln Val Asn Ile Val Lys Lys Thr
1085             1090                 1095

Glu Val Gln Thr Gly Gly Phe Ser Lys Glu Ser Ile Leu Pro Lys
1100             1105                 1110

Arg Asn Ser Asp Lys Leu Ile Ala Arg Lys Lys Asp Trp Asp Pro
1115             1120                 1125

Lys Lys Tyr Gly Gly Phe Asp Ser Pro Thr Val Ala Tyr Ser Val
1130             1135                 1140

Leu Val Val Ala Lys Val Glu Lys Gly Lys Ser Lys Lys Leu Lys
1145             1150                 1155

Ser Val Lys Glu Leu Leu Gly Ile Thr Ile Met Glu Arg Ser Ser
1160             1165                 1170

Phe Glu Lys Asn Pro Ile Asp Phe Leu Glu Ala Lys Gly Tyr Lys
1175             1180                 1185

Glu Val Lys Lys Asp Leu Ile Ile Lys Leu Pro Lys Tyr Ser Leu
1190             1195                 1200

Phe Glu Leu Glu Asn Gly Arg Lys Arg Met Leu Ala Ser Ala Gly
1205             1210                 1215

Glu Leu Gln Lys Gly Asn Glu Leu Ala Leu Pro Ser Lys Tyr Val
1220             1225                 1230

Asn Phe Leu Tyr Leu Ala Ser His Tyr Glu Lys Leu Lys Gly Ser
1235             1240                 1245

Pro Glu Asp Asn Glu Gln Lys Gln Leu Phe Val Glu Gln His Lys
1250             1255                 1260

His Tyr Leu Asp Glu Ile Ile Glu Gln Ile Ser Glu Phe Ser Lys
1265             1270                 1275

Arg Val Ile Leu Ala Asp Ala Asn Leu Asp Lys Val Leu Ser Ala
1280             1285                 1290

Tyr Asn Lys His Arg Asp Lys Pro Ile Arg Glu Gln Ala Glu Asn
1295             1300                 1305

Ile Ile His Leu Phe Thr Leu Thr Asn Leu Gly Ala Pro Ala Ala
1310             1315                 1320

Phe Lys Tyr Phe Asp Thr Thr Ile Asp Arg Lys Arg Tyr Thr Ser
1325             1330                 1335

Thr Lys Glu Val Leu Asp Ala Thr Leu Ile His Gln Ser Ile Thr
1340             1345                 1350

Gly Leu Tyr Glu Thr Arg Ile Asp Leu Ser Gln Leu Gly Gly Asp
1355             1360                 1365

<210> SEQ ID NO 2
<211> LENGTH: 3
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(1)
<223> OTHER INFORMATION: N is any of nucleotides T, C, A or G

<400> SEQUENCE: 2 ngg                                                                        3

<210> SEQ ID NO 3
<211> LENGTH: 96

```
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 3
nnnnnnnnnn nnnnnnnnnn guuuuagagc uagaaauagc aaguuaaaau aaggcuaguc        60
cguuaucaac uugaaaaagu ggcaccgagu cggugc                                  96

<210> SEQ ID NO 4
<211> LENGTH: 76
<212> TYPE: RNA
<213> ORGANISM: Artificial Sequence
<220> FEATURE:
<223> OTHER INFORMATION: gRNA

<400> SEQUENCE: 4
guuuuagagc uagaaauagc aaguuaaaau aaggcuaguc cguuaucaac uugaaaaagu        60
ggcaccgagu cggugc                                                        76

<210> SEQ ID NO 5
<211> LENGTH: 1378
<212> TYPE: PRT
<213> ORGANISM: Streptococcus pyogenes

<400> SEQUENCE: 5

Met Pro Lys Lys Lys Arg Lys Val Gly Ser Met Asp Lys Lys Tyr Ser
 1               5                  10                  15

Ile Gly Leu Asp Ile Gly Thr Asn Ser Val Gly Trp Ala Val Ile Thr
            20                  25                  30

Asp Glu Tyr Lys Val Pro Ser Lys Lys Phe Lys Val Leu Gly Asn Thr
        35                  40                  45

Asp Arg His Ser Ile Lys Lys Asn Leu Ile Gly Ala Leu Leu Phe Asp
    50                  55                  60

Ser Gly Glu Thr Ala Glu Ala Thr Arg Leu Lys Arg Thr Ala Arg Arg
65                  70                  75                  80

Arg Tyr Thr Arg Arg Lys Asn Arg Ile Cys Tyr Leu Gln Glu Ile Phe
                85                  90                  95

Ser Asn Glu Met Ala Lys Val Asp Asp Ser Phe Phe His Arg Leu Glu
            100                 105                 110

Glu Ser Phe Leu Val Glu Glu Asp Lys Lys His Glu Arg His Pro Ile
        115                 120                 125

Phe Gly Asn Ile Val Asp Glu Val Ala Tyr His Glu Lys Tyr Pro Thr
    130                 135                 140

Ile Tyr His Leu Arg Lys Lys Leu Val Asp Ser Thr Asp Lys Ala Asp
145                 150                 155                 160

Leu Arg Leu Ile Tyr Leu Ala Leu Ala His Met Ile Lys Phe Arg Gly
                165                 170                 175

His Phe Leu Ile Glu Gly Asp Leu Asn Pro Asp Asn Ser Asp Val Asp
            180                 185                 190

Lys Leu Phe Ile Gln Leu Val Gln Thr Tyr Asn Gln Leu Phe Glu Glu
        195                 200                 205

Asn Pro Ile Asn Ala Ser Gly Val Asp Ala Lys Ala Ile Leu Ser Ala
    210                 215                 220
```

```
Arg Leu Ser Lys Ser Arg Arg Leu Glu Asn Leu Ile Ala Gln Leu Pro
225                 230                 235                 240

Gly Glu Lys Lys Asn Gly Leu Phe Gly Asn Leu Ile Ala Leu Ser Leu
                245                 250                 255

Gly Leu Thr Pro Asn Phe Lys Ser Asn Phe Asp Leu Ala Glu Asp Ala
            260                 265                 270

Lys Leu Gln Leu Ser Lys Asp Thr Tyr Asp Asp Leu Asp Asn Leu
        275                 280                 285

Leu Ala Gln Ile Gly Asp Gln Tyr Ala Asp Leu Phe Leu Ala Ala Lys
        290                 295                 300

Asn Leu Ser Asp Ala Ile Leu Leu Ser Asp Ile Leu Arg Val Asn Thr
305                 310                 315                 320

Glu Ile Thr Lys Ala Pro Leu Ser Ala Ser Met Ile Lys Arg Tyr Asp
                325                 330                 335

Glu His His Gln Asp Leu Thr Leu Leu Lys Ala Leu Val Arg Gln Gln
                340                 345                 350

Leu Pro Glu Lys Tyr Lys Glu Ile Phe Phe Asp Gln Ser Lys Asn Gly
            355                 360                 365

Tyr Ala Gly Tyr Ile Asp Gly Gly Ala Ser Gln Glu Glu Phe Tyr Lys
        370                 375                 380

Phe Ile Lys Pro Ile Leu Glu Lys Met Asp Gly Thr Glu Glu Leu Leu
385                 390                 395                 400

Val Lys Leu Asn Arg Glu Asp Leu Leu Arg Lys Gln Arg Thr Phe Asp
                405                 410                 415

Asn Gly Ser Ile Pro His Gln Ile His Leu Gly Glu Leu His Ala Ile
            420                 425                 430

Leu Arg Arg Gln Glu Asp Phe Tyr Pro Phe Leu Lys Asp Asn Arg Glu
        435                 440                 445

Lys Ile Glu Lys Ile Leu Thr Phe Arg Ile Pro Tyr Tyr Val Gly Pro
    450                 455                 460

Leu Ala Arg Gly Asn Ser Arg Phe Ala Trp Met Thr Arg Lys Ser Glu
465                 470                 475                 480

Glu Thr Ile Thr Pro Trp Asn Phe Glu Glu Val Val Asp Lys Gly Ala
                485                 490                 495

Ser Ala Gln Ser Phe Ile Glu Arg Met Thr Asn Phe Asp Lys Asn Leu
            500                 505                 510

Pro Asn Glu Lys Val Leu Pro Lys His Ser Leu Leu Tyr Glu Tyr Phe
        515                 520                 525

Thr Val Tyr Asn Glu Leu Thr Lys Val Lys Tyr Val Thr Glu Gly Met
530                 535                 540

Arg Lys Pro Ala Phe Leu Ser Gly Glu Gln Lys Lys Ala Ile Val Asp
545                 550                 555                 560

Leu Leu Phe Lys Thr Asn Arg Lys Val Thr Val Lys Gln Leu Lys Glu
                565                 570                 575

Asp Tyr Phe Lys Lys Ile Glu Cys Phe Asp Ser Val Glu Ile Ser Gly
            580                 585                 590

Val Glu Asp Arg Phe Asn Ala Ser Leu Gly Thr Tyr His Asp Leu Leu
        595                 600                 605

Lys Ile Ile Lys Asp Lys Asp Phe Leu Asp Asn Glu Glu Asn Glu Asp
        610                 615                 620

Ile Leu Glu Asp Ile Val Leu Thr Leu Thr Leu Phe Glu Asp Arg Glu
625                 630                 635                 640

Met Ile Glu Glu Arg Leu Lys Thr Tyr Ala His Leu Phe Asp Asp Lys
```

```
                        645                 650                 655
Val Met Lys Gln Leu Lys Arg Arg Tyr Thr Gly Trp Gly Arg Leu
                    660                 665                 670

Ser Arg Lys Leu Ile Asn Gly Ile Arg Asp Lys Gln Ser Gly Lys Thr
                675                 680                 685

Ile Leu Asp Phe Leu Lys Ser Asp Gly Phe Ala Asn Arg Asn Phe Met
            690                 695                 700

Gln Leu Ile His Asp Asp Ser Leu Thr Phe Lys Glu Asp Ile Gln Lys
705                 710                 715                 720

Ala Gln Val Ser Gly Gln Gly Asp Ser Leu His Glu His Ile Ala Asn
                725                 730                 735

Leu Ala Gly Ser Pro Ala Ile Lys Lys Gly Ile Leu Gln Thr Val Lys
                740                 745                 750

Val Val Asp Glu Leu Val Lys Val Met Gly Arg His Lys Pro Glu Asn
                755                 760                 765

Ile Val Ile Glu Met Ala Arg Glu Asn Gln Thr Thr Gln Lys Gly Gln
            770                 775                 780

Lys Asn Ser Arg Glu Arg Met Lys Arg Ile Glu Glu Gly Ile Lys Glu
785                 790                 795                 800

Leu Gly Ser Gln Ile Leu Lys Glu His Pro Val Glu Asn Thr Gln Leu
                805                 810                 815

Gln Asn Glu Lys Leu Tyr Leu Tyr Tyr Leu Gln Asn Gly Arg Asp Met
                820                 825                 830

Tyr Val Asp Gln Glu Leu Asp Ile Asn Arg Leu Ser Asp Tyr Asp Val
                835                 840                 845

Asp His Ile Val Pro Gln Ser Phe Leu Lys Asp Asp Ser Ile Asp Asn
            850                 855                 860

Lys Val Leu Thr Arg Ser Asp Lys Asn Arg Gly Lys Ser Asp Asn Val
865                 870                 875                 880

Pro Ser Glu Glu Val Val Lys Lys Met Lys Asn Tyr Trp Arg Gln Leu
                885                 890                 895

Leu Asn Ala Lys Leu Ile Thr Gln Arg Lys Phe Asp Asn Leu Thr Lys
                900                 905                 910

Ala Glu Arg Gly Gly Leu Ser Glu Leu Asp Lys Ala Gly Phe Ile Lys
                915                 920                 925

Arg Gln Leu Val Glu Thr Arg Gln Ile Thr Lys His Val Ala Gln Ile
            930                 935                 940

Leu Asp Ser Arg Met Asn Thr Lys Tyr Asp Glu Asn Asp Lys Leu Ile
945                 950                 955                 960

Arg Glu Val Lys Val Ile Thr Leu Lys Ser Lys Leu Val Ser Asp Phe
                965                 970                 975

Arg Lys Asp Phe Gln Phe Tyr Lys Val Arg Glu Ile Asn Asn Tyr His
                980                 985                 990

His Ala His Asp Ala Tyr Leu Asn Ala Val Val Gly Thr Ala Leu Ile
            995                 1000                1005

Lys Lys Tyr Pro Lys Leu Glu Ser Glu Phe Val Tyr Gly Asp Tyr
            1010                1015                1020

Lys Val Tyr Asp Val Arg Lys Met Ile Ala Lys Ser Glu Gln Glu
            1025                1030                1035

Ile Gly Lys Ala Thr Ala Lys Tyr Phe Phe Tyr Ser Asn Ile Met
            1040                1045                1050

Asn Phe Phe Lys Thr Glu Ile Thr Leu Ala Asn Gly Glu Ile Arg
            1055                1060                1065
```

```
Lys Arg Pro Leu Ile Glu Thr Asn Gly Glu Thr Gly Glu Ile Val
    1070                1075                1080

Trp Asp Lys Gly Arg Asp Phe Ala Thr Val Arg Lys Val Leu Ser
    1085                1090                1095

Met Pro Gln Val Asn Ile Val Lys Lys Thr Glu Val Gln Thr Gly
    1100                1105                1110

Gly Phe Ser Lys Glu Ser Ile Leu Pro Lys Arg Asn Ser Asp Lys
    1115                1120                1125

Leu Ile Ala Arg Lys Lys Asp Trp Asp Pro Lys Lys Tyr Gly Gly
    1130                1135                1140

Phe Asp Ser Pro Thr Val Ala Tyr Ser Val Leu Val Val Ala Lys
    1145                1150                1155

Val Glu Lys Gly Lys Ser Lys Lys Leu Lys Ser Val Lys Glu Leu
    1160                1165                1170

Leu Gly Ile Thr Ile Met Glu Arg Ser Ser Phe Glu Lys Asn Pro
    1175                1180                1185

Ile Asp Phe Leu Glu Ala Lys Gly Tyr Lys Glu Val Lys Lys Asp
    1190                1195                1200

Leu Ile Ile Lys Leu Pro Lys Tyr Ser Leu Phe Glu Leu Glu Asn
    1205                1210                1215

Gly Arg Lys Arg Met Leu Ala Ser Ala Gly Glu Leu Gln Lys Gly
    1220                1225                1230

Asn Glu Leu Ala Leu Pro Ser Lys Tyr Val Asn Phe Leu Tyr Leu
    1235                1240                1245

Ala Ser His Tyr Glu Lys Leu Lys Gly Ser Pro Glu Asp Asn Glu
    1250                1255                1260

Gln Lys Gln Leu Phe Val Glu Gln His Lys His Tyr Leu Asp Glu
    1265                1270                1275

Ile Ile Glu Gln Ile Ser Glu Phe Ser Lys Arg Val Ile Leu Ala
    1280                1285                1290

Asp Ala Asn Leu Asp Lys Val Leu Ser Ala Tyr Asn Lys His Arg
    1295                1300                1305

Asp Lys Pro Ile Arg Glu Gln Ala Glu Asn Ile Ile His Leu Phe
    1310                1315                1320

Thr Leu Thr Asn Leu Gly Ala Pro Ala Ala Phe Lys Tyr Phe Asp
    1325                1330                1335

Thr Thr Ile Asp Arg Lys Arg Tyr Thr Ser Thr Lys Glu Val Leu
    1340                1345                1350

Asp Ala Thr Leu Ile His Gln Ser Ile Thr Gly Leu Tyr Glu Thr
    1355                1360                1365

Arg Ile Asp Leu Ser Gln Leu Gly Gly Asp
    1370                1375

<210> SEQ ID NO 6
<211> LENGTH: 7
<212> TYPE: PRT
<213> ORGANISM: Artificial Sequence
<220> FEATURE:
<223> OTHER INFORMATION: Signal

<400> SEQUENCE: 6

Pro Lys Lys Lys Arg Lys Val
1               5

<210> SEQ ID NO 7
```

```
<211> LENGTH: 1377
<212> TYPE: PRT
<213> ORGANISM: Streptococcus pyogenes

<400> SEQUENCE: 7
```

| | | | | | | | | | | | | | | |
|---|---|---|---|---|---|---|---|---|---|---|---|---|---|---|
| Met | Asp | Lys | Lys | Tyr | Ser | Ile | Gly | Leu | Asp | Ile | Gly | Thr | Asn | Ser | Val |
| 1 | | | | 5 | | | | | 10 | | | | | 15 | |
| Gly | Trp | Ala | Val | Ile | Thr | Asp | Glu | Tyr | Lys | Val | Pro | Ser | Lys | Lys | Phe |
| | | | 20 | | | | | 25 | | | | | 30 | | |
| Lys | Val | Leu | Gly | Asn | Thr | Asp | Arg | His | Ser | Ile | Lys | Lys | Asn | Leu | Ile |
| | | | | 35 | | | | | 40 | | | | | 45 | |
| Gly | Ala | Leu | Leu | Phe | Asp | Ser | Gly | Glu | Thr | Ala | Glu | Ala | Thr | Arg | Leu |
| | 50 | | | | | 55 | | | | | 60 | | | | |
| Lys | Arg | Thr | Ala | Arg | Arg | Arg | Tyr | Thr | Arg | Arg | Lys | Asn | Arg | Ile | Cys |
| 65 | | | | | 70 | | | | | 75 | | | | | 80 |
| Tyr | Leu | Gln | Glu | Ile | Phe | Ser | Asn | Glu | Met | Ala | Lys | Val | Asp | Asp | Ser |
| | | | | 85 | | | | | 90 | | | | | 95 | |
| Phe | Phe | His | Arg | Leu | Glu | Glu | Ser | Phe | Leu | Val | Glu | Glu | Asp | Lys | Lys |
| | | | 100 | | | | | 105 | | | | | 110 | | |
| His | Glu | Arg | His | Pro | Ile | Phe | Gly | Asn | Ile | Val | Asp | Glu | Val | Ala | Tyr |
| | | | | 115 | | | | | 120 | | | | | 125 | |
| His | Glu | Lys | Tyr | Pro | Thr | Ile | Tyr | His | Leu | Arg | Lys | Lys | Leu | Val | Asp |
| | 130 | | | | | 135 | | | | | 140 | | | | |
| Ser | Thr | Asp | Lys | Ala | Asp | Leu | Arg | Leu | Ile | Tyr | Leu | Ala | Leu | Ala | His |
| 145 | | | | | 150 | | | | | 155 | | | | | 160 |
| Met | Ile | Lys | Phe | Arg | Gly | His | Phe | Leu | Ile | Glu | Gly | Asp | Leu | Asn | Pro |
| | | | | 165 | | | | | 170 | | | | | 175 | |
| Asp | Asn | Ser | Asp | Val | Asp | Lys | Leu | Phe | Ile | Gln | Leu | Val | Gln | Thr | Tyr |
| | | | 180 | | | | | 185 | | | | | 190 | | |
| Asn | Gln | Leu | Phe | Glu | Glu | Asn | Pro | Ile | Asn | Ala | Ser | Gly | Val | Asp | Ala |
| | | | | 195 | | | | | 200 | | | | | 205 | |
| Lys | Ala | Ile | Leu | Ser | Ala | Arg | Leu | Ser | Lys | Ser | Arg | Arg | Leu | Glu | Asn |
| | 210 | | | | | 215 | | | | | 220 | | | | |
| Leu | Ile | Ala | Gln | Leu | Pro | Gly | Glu | Lys | Lys | Asn | Gly | Leu | Phe | Gly | Asn |
| 225 | | | | | 230 | | | | | 235 | | | | | 240 |
| Leu | Ile | Ala | Leu | Ser | Leu | Gly | Leu | Thr | Pro | Asn | Phe | Lys | Ser | Asn | Phe |
| | | | | 245 | | | | | 250 | | | | | 255 | |
| Asp | Leu | Ala | Glu | Asp | Ala | Lys | Leu | Gln | Leu | Ser | Lys | Asp | Thr | Tyr | Asp |
| | | | 260 | | | | | 265 | | | | | 270 | | |
| Asp | Asp | Leu | Asp | Asn | Leu | Leu | Ala | Gln | Ile | Gly | Asp | Gln | Tyr | Ala | Asp |
| | | | | 275 | | | | | 280 | | | | | 285 | |
| Leu | Phe | Leu | Ala | Ala | Lys | Asn | Leu | Ser | Asp | Ala | Ile | Leu | Leu | Ser | Asp |
| | 290 | | | | | 295 | | | | | 300 | | | | |
| Ile | Leu | Arg | Val | Asn | Thr | Glu | Ile | Thr | Lys | Ala | Pro | Leu | Ser | Ala | Ser |
| 305 | | | | | 310 | | | | | 315 | | | | | 320 |
| Met | Ile | Lys | Arg | Tyr | Asp | Glu | His | His | Gln | Asp | Leu | Thr | Leu | Leu | Lys |
| | | | | 325 | | | | | 330 | | | | | 335 | |
| Ala | Leu | Val | Arg | Gln | Gln | Leu | Pro | Glu | Lys | Tyr | Lys | Glu | Ile | Phe | Phe |
| | | | 340 | | | | | 345 | | | | | 350 | | |
| Asp | Gln | Ser | Lys | Asn | Gly | Tyr | Ala | Gly | Tyr | Ile | Asp | Gly | Gly | Ala | Ser |
| | | | | 355 | | | | | 360 | | | | | 365 | |
| Gln | Glu | Glu | Phe | Tyr | Lys | Phe | Ile | Lys | Pro | Ile | Leu | Glu | Lys | Met | Asp |
| | 370 | | | | | 375 | | | | | 380 | | | | |
| Gly | Thr | Glu | Glu | Leu | Leu | Val | Lys | Leu | Asn | Arg | Glu | Asp | Leu | Leu | Arg |

-continued

```
                385                 390                 395                 400
Lys Gln Arg Thr Phe Asp Asn Gly Ser Ile Pro His Gln Ile His Leu
                    405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                    435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                    500                 505                 510

Leu Leu Tyr Glu Tyr Phe Thr Val Tyr Asn Glu Leu Thr Lys Val Lys
                    515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                    565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                    595                 600                 605

Asn Glu Glu Asn Glu Asp Ile Leu Glu Asp Ile Val Leu Thr Leu Thr
                    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                    645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                    675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
                    740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
                770                 775                 780

Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                    805                 810                 815
```

-continued

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Gly Ser Pro Lys Lys Lys Arg Lys Val
    1370                1375

<210> SEQ ID NO 8
<211> LENGTH: 1387
<212> TYPE: PRT
<213> ORGANISM: Streptococcus pyogenes

<400> SEQUENCE: 8

Met Pro Lys Lys Lys Arg Lys Val Gly Ser Met Asp Lys Tyr Ser
1               5                   10                  15

Ile Gly Leu Asp Ile Gly Thr Asn Ser Val Gly Trp Ala Val Ile Thr
            20                  25                  30

Asp Glu Tyr Lys Val Pro Ser Lys Lys Phe Lys Val Leu Gly Asn Thr
        35                  40                  45

Asp Arg His Ser Ile Lys Lys Asn Leu Ile Gly Ala Leu Leu Phe Asp
    50                  55                  60

Ser Gly Glu Thr Ala Glu Ala Thr Arg Leu Lys Arg Thr Ala Arg Arg
65                  70                  75                  80

Arg Tyr Thr Arg Arg Lys Asn Arg Ile Cys Tyr Leu Gln Glu Ile Phe
                85                  90                  95

Ser Asn Glu Met Ala Lys Val Asp Asp Ser Phe Phe His Arg Leu Glu
            100                 105                 110

Glu Ser Phe Leu Val Glu Glu Asp Lys Lys His Glu Arg His Pro Ile
        115                 120                 125

Phe Gly Asn Ile Val Asp Glu Val Ala Tyr His Glu Lys Tyr Pro Thr
    130                 135                 140

Ile Tyr His Leu Arg Lys Lys Leu Val Asp Ser Thr Asp Lys Ala Asp
145                 150                 155                 160

Leu Arg Leu Ile Tyr Leu Ala Leu Ala His Met Ile Lys Phe Arg Gly
                165                 170                 175

His Phe Leu Ile Glu Gly Asp Leu Asn Pro Asp Asn Ser Asp Val Asp
            180                 185                 190

Lys Leu Phe Ile Gln Leu Val Gln Thr Tyr Asn Gln Leu Phe Glu Glu
        195                 200                 205

Asn Pro Ile Asn Ala Ser Gly Val Asp Ala Lys Ala Ile Leu Ser Ala
210                 215                 220

Arg Leu Ser Lys Ser Arg Arg Leu Glu Asn Leu Ile Ala Gln Leu Pro
225                 230                 235                 240

Gly Glu Lys Lys Asn Gly Leu Phe Gly Asn Leu Ile Ala Leu Ser Leu
                245                 250                 255

Gly Leu Thr Pro Asn Phe Lys Ser Asn Phe Asp Leu Ala Glu Asp Ala
                260                 265                 270

Lys Leu Gln Leu Ser Lys Asp Thr Tyr Asp Asp Leu Asp Asn Leu
            275                 280                 285

Leu Ala Gln Ile Gly Asp Gln Tyr Ala Asp Leu Phe Leu Ala Ala Lys
            290                 295                 300

Asn Leu Ser Asp Ala Ile Leu Leu Ser Asp Ile Leu Arg Val Asn Thr
305                 310                 315                 320

Glu Ile Thr Lys Ala Pro Leu Ser Ala Ser Met Ile Lys Arg Tyr Asp
                325                 330                 335

Glu His His Gln Asp Leu Thr Leu Leu Lys Ala Leu Val Arg Gln Gln
                340                 345                 350

Leu Pro Glu Lys Tyr Lys Glu Ile Phe Phe Asp Gln Ser Lys Asn Gly
            355                 360                 365

Tyr Ala Gly Tyr Ile Asp Gly Gly Ala Ser Gln Glu Glu Phe Tyr Lys
            370                 375                 380

Phe Ile Lys Pro Ile Leu Glu Lys Met Asp Gly Thr Glu Glu Leu Leu
385                 390                 395                 400

Val Lys Leu Asn Arg Glu Asp Leu Leu Arg Lys Gln Arg Thr Phe Asp
                405                 410                 415

Asn Gly Ser Ile Pro His Gln Ile His Leu Gly Glu Leu His Ala Ile
                420                 425                 430

Leu Arg Arg Gln Glu Asp Phe Tyr Pro Phe Leu Lys Asp Asn Arg Glu
            435                 440                 445

Lys Ile Glu Lys Ile Leu Thr Phe Arg Ile Pro Tyr Tyr Val Gly Pro
450                 455                 460

Leu Ala Arg Gly Asn Ser Arg Phe Ala Trp Met Thr Arg Lys Ser Glu
465                 470                 475                 480

Glu Thr Ile Thr Pro Trp Asn Phe Glu Glu Val Val Asp Lys Gly Ala
                485                 490                 495

Ser Ala Gln Ser Phe Ile Glu Arg Met Thr Asn Phe Asp Lys Asn Leu
            500                 505                 510

Pro Asn Glu Lys Val Leu Pro Lys His Ser Leu Leu Tyr Glu Tyr Phe
            515                 520                 525

Thr Val Tyr Asn Glu Leu Thr Lys Val Lys Tyr Val Thr Glu Gly Met
530                 535                 540

Arg Lys Pro Ala Phe Leu Ser Gly Glu Gln Lys Lys Ala Ile Val Asp
545                 550                 555                 560

Leu Leu Phe Lys Thr Asn Arg Lys Val Thr Val Lys Gln Leu Lys Glu
                565                 570                 575

Asp Tyr Phe Lys Lys Ile Glu Cys Phe Asp Ser Val Glu Ile Ser Gly
            580                 585                 590

Val Glu Asp Arg Phe Asn Ala Ser Leu Gly Thr Tyr His Asp Leu Leu
            595                 600                 605

Lys Ile Ile Lys Asp Lys Asp Phe Leu Asp Asn Glu Glu Asn Glu Asp
610                 615                 620

-continued

```
Ile Leu Glu Asp Ile Val Leu Thr Leu Thr Leu Phe Glu Asp Arg Glu
625                 630                 635                 640

Met Ile Glu Glu Arg Leu Lys Thr Tyr Ala His Leu Phe Asp Asp Lys
            645                 650                 655

Val Met Lys Gln Leu Lys Arg Arg Tyr Thr Gly Trp Gly Arg Leu
        660                 665                 670

Ser Arg Lys Leu Ile Asn Gly Ile Arg Asp Lys Gln Ser Gly Lys Thr
    675                 680                 685

Ile Leu Asp Phe Leu Lys Ser Asp Gly Phe Ala Asn Arg Asn Phe Met
690                 695                 700

Gln Leu Ile His Asp Asp Ser Leu Thr Phe Lys Glu Asp Ile Gln Lys
705                 710                 715                 720

Ala Gln Val Ser Gly Gln Gly Asp Ser Leu His Glu His Ile Ala Asn
            725                 730                 735

Leu Ala Gly Ser Pro Ala Ile Lys Lys Gly Ile Leu Gln Thr Val Lys
            740                 745                 750

Val Val Asp Glu Leu Val Lys Val Met Gly Arg His Lys Pro Glu Asn
        755                 760                 765

Ile Val Ile Glu Met Ala Arg Glu Asn Gln Thr Thr Gln Lys Gly Gln
770                 775                 780

Lys Asn Ser Arg Glu Arg Met Lys Arg Ile Glu Glu Gly Ile Lys Glu
785                 790                 795                 800

Leu Gly Ser Gln Ile Leu Lys Glu His Pro Val Glu Asn Thr Gln Leu
            805                 810                 815

Gln Asn Glu Lys Leu Tyr Leu Tyr Tyr Leu Gln Asn Gly Arg Asp Met
        820                 825                 830

Tyr Val Asp Gln Glu Leu Asp Ile Asn Arg Leu Ser Asp Tyr Asp Val
    835                 840                 845

Asp His Ile Val Pro Gln Ser Phe Leu Lys Asp Asp Ser Ile Asp Asn
850                 855                 860

Lys Val Leu Thr Arg Ser Asp Lys Asn Arg Gly Lys Ser Asp Asn Val
865                 870                 875                 880

Pro Ser Glu Glu Val Val Lys Lys Met Lys Asn Tyr Trp Arg Gln Leu
            885                 890                 895

Leu Asn Ala Lys Leu Ile Thr Gln Arg Lys Phe Asp Asn Leu Thr Lys
        900                 905                 910

Ala Glu Arg Gly Gly Leu Ser Glu Leu Asp Lys Ala Gly Phe Ile Lys
    915                 920                 925

Arg Gln Leu Val Glu Thr Arg Gln Ile Thr Lys His Val Ala Gln Ile
930                 935                 940

Leu Asp Ser Arg Met Asn Thr Lys Tyr Asp Glu Asn Asp Lys Leu Ile
945                 950                 955                 960

Arg Glu Val Lys Val Ile Thr Leu Lys Ser Lys Leu Val Ser Asp Phe
            965                 970                 975

Arg Lys Asp Phe Gln Phe Tyr Lys Val Arg Glu Ile Asn Asn Tyr His
        980                 985                 990

His Ala His Asp Ala Tyr Leu Asn Ala Val Val Gly Thr Ala Leu Ile
    995                 1000                1005

Lys Lys Tyr Pro Lys Leu Glu Ser Glu Phe Val Tyr Gly Asp Tyr
        1010                1015                1020

Lys Val Tyr Asp Val Arg Lys Met Ile Ala Lys Ser Glu Gln Glu
    1025                1030                1035

Ile Gly Lys Ala Thr Ala Lys Tyr Phe Phe Tyr Ser Asn Ile Met
```

```
                    1040                1045                1050
Asn Phe Phe Lys Thr Glu Ile Thr Leu Ala Asn Gly Glu Ile Arg
            1055                1060                1065

Lys Arg Pro Leu Ile Glu Thr Asn Gly Glu Thr Gly Glu Ile Val
        1070                1075                1080

Trp Asp Lys Gly Arg Asp Phe Ala Thr Val Arg Lys Val Leu Ser
    1085                1090                1095

Met Pro Gln Val Asn Ile Val Lys Lys Thr Glu Val Gln Thr Gly
    1100                1105                1110

Gly Phe Ser Lys Glu Ser Ile Leu Pro Lys Arg Asn Ser Asp Lys
    1115                1120                1125

Leu Ile Ala Arg Lys Lys Asp Trp Asp Pro Lys Lys Tyr Gly Gly
    1130                1135                1140

Phe Asp Ser Pro Thr Val Ala Tyr Ser Val Leu Val Val Ala Lys
    1145                1150                1155

Val Glu Lys Gly Lys Ser Lys Lys Leu Lys Ser Val Lys Glu Leu
    1160                1165                1170

Leu Gly Ile Thr Ile Met Glu Arg Ser Ser Phe Glu Lys Asn Pro
    1175                1180                1185

Ile Asp Phe Leu Glu Ala Lys Gly Tyr Lys Glu Val Lys Lys Asp
    1190                1195                1200

Leu Ile Ile Lys Leu Pro Lys Tyr Ser Leu Phe Glu Leu Glu Asn
    1205                1210                1215

Gly Arg Lys Arg Met Leu Ala Ser Ala Gly Glu Leu Gln Lys Gly
    1220                1225                1230

Asn Glu Leu Ala Leu Pro Ser Lys Tyr Val Asn Phe Leu Tyr Leu
    1235                1240                1245

Ala Ser His Tyr Glu Lys Leu Lys Gly Ser Pro Glu Asp Asn Glu
    1250                1255                1260

Gln Lys Gln Leu Phe Val Glu Gln His Lys His Tyr Leu Asp Glu
    1265                1270                1275

Ile Ile Glu Gln Ile Ser Glu Phe Ser Lys Arg Val Ile Leu Ala
    1280                1285                1290

Asp Ala Asn Leu Asp Lys Val Leu Ser Ala Tyr Asn Lys His Arg
    1295                1300                1305

Asp Lys Pro Ile Arg Glu Gln Ala Glu Asn Ile Ile His Leu Phe
    1310                1315                1320

Thr Leu Thr Asn Leu Gly Ala Pro Ala Ala Phe Lys Tyr Phe Asp
    1325                1330                1335

Thr Thr Ile Asp Arg Lys Arg Tyr Thr Ser Thr Lys Glu Val Leu
    1340                1345                1350

Asp Ala Thr Leu Ile His Gln Ser Ile Thr Gly Leu Tyr Glu Thr
    1355                1360                1365

Arg Ile Asp Leu Ser Gln Leu Gly Gly Asp Gly Ser Pro Lys Lys
    1370                1375                1380

Lys Arg Lys Val
    1385

<210> SEQ ID NO 9
<211> LENGTH: 1423
<212> TYPE: PRT
<213> ORGANISM: Streptococcus pyogenes

<400> SEQUENCE: 9
```

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
        20                  25                  30

Gly Ile His Gly Val Pro Ala Ala Asp Lys Lys Tyr Ser Ile Gly Leu
            35                  40                  45

Asp Ile Gly Thr Asn Ser Val Gly Trp Ala Val Ile Thr Asp Glu Tyr
        50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Tyr Thr
            100                 105                 110

Arg Arg Lys Asn Arg Ile Cys Tyr Leu Gln Glu Ile Phe Ser Asn Glu
            115                 120                 125

Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
    195                 200                 205

Ile Glu Gly Asp Leu Asn Pro Asp Asn Ser Asp Val Asp Lys Leu Phe
210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
            275                 280                 285

Pro Asn Phe Lys Ser Asn Phe Asp Leu Ala Glu Asp Ala Lys Leu Gln
    290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
            355                 360                 365

Gln Asp Leu Thr Leu Leu Lys Ala Leu Val Arg Gln Gln Leu Pro Glu
    370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu

```
              420             425             430
Asn Arg Glu Asp Leu Leu Arg Lys Gln Arg Thr Phe Asp Asn Gly Ser
            435                 440                 445
Ile Pro His Gln Ile His Leu Gly Glu Leu His Ala Ile Leu Arg Arg
450                 455                 460
Gln Glu Asp Phe Tyr Pro Phe Leu Lys Asp Asn Arg Glu Lys Ile Glu
465                 470                 475                 480
Lys Ile Leu Thr Phe Arg Ile Pro Tyr Tyr Val Gly Pro Leu Ala Arg
                485                 490                 495
Gly Asn Ser Arg Phe Ala Trp Met Thr Arg Lys Ser Glu Glu Thr Ile
                500                 505                 510
Thr Pro Trp Asn Phe Glu Glu Val Val Asp Lys Gly Ala Ser Ala Gln
            515                 520                 525
Ser Phe Ile Glu Arg Met Thr Asn Phe Asp Lys Asn Leu Pro Asn Glu
            530                 535                 540
Lys Val Leu Pro Lys His Ser Leu Leu Tyr Glu Tyr Phe Thr Val Tyr
545                 550                 555                 560
Asn Glu Leu Thr Lys Val Lys Tyr Val Thr Glu Gly Met Arg Lys Pro
                565                 570                 575
Ala Phe Leu Ser Gly Glu Gln Lys Lys Ala Ile Val Asp Leu Leu Phe
                580                 585                 590
Lys Thr Asn Arg Lys Val Thr Val Lys Gln Leu Lys Glu Asp Tyr Phe
                595                 600                 605
Lys Lys Ile Glu Cys Phe Asp Ser Val Glu Ile Ser Gly Val Glu Asp
            610                 615                 620
Arg Phe Asn Ala Ser Leu Gly Thr Tyr His Asp Leu Leu Lys Ile Ile
625                 630                 635                 640
Lys Asp Lys Asp Phe Leu Asp Asn Glu Glu Asn Glu Asp Ile Leu Glu
                645                 650                 655
Asp Ile Val Leu Thr Leu Thr Leu Phe Glu Asp Arg Glu Met Ile Glu
                660                 665                 670
Glu Arg Leu Lys Thr Tyr Ala His Leu Phe Asp Asp Lys Val Met Lys
            675                 680                 685
Gln Leu Lys Arg Arg Arg Tyr Thr Gly Trp Gly Arg Leu Ser Arg Lys
            690                 695                 700
Leu Ile Asn Gly Ile Arg Asp Lys Gln Ser Gly Lys Thr Ile Leu Asp
705                 710                 715                 720
Phe Leu Lys Ser Asp Gly Phe Ala Asn Arg Asn Phe Met Gln Leu Ile
                725                 730                 735
His Asp Asp Ser Leu Thr Phe Lys Glu Asp Ile Gln Lys Ala Gln Val
            740                 745                 750
Ser Gly Gln Gly Asp Ser Leu His Glu His Ile Ala Asn Leu Ala Gly
            755                 760                 765
Ser Pro Ala Ile Lys Lys Gly Ile Leu Gln Thr Val Lys Val Val Asp
            770                 775                 780
Glu Leu Val Lys Val Met Gly Arg His Lys Pro Glu Asn Ile Val Ile
785                 790                 795                 800
Glu Met Ala Arg Glu Asn Gln Thr Thr Gln Lys Gly Gln Lys Asn Ser
                805                 810                 815
Arg Glu Arg Met Lys Arg Ile Glu Glu Gly Ile Lys Glu Leu Gly Ser
                820                 825                 830
Gln Ile Leu Lys Glu His Pro Val Glu Asn Thr Gln Leu Gln Asn Glu
            835                 840                 845
```

-continued

```
Lys Leu Tyr Leu Tyr Leu Gln Asn Gly Arg Asp Met Tyr Val Asp
    850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
                885                 890                 895

Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
        915                 920                 925

Lys Leu Ile Thr Gln Arg Lys Phe Asp Asn Leu Thr Lys Ala Glu Arg
    930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                965                 970                 975

Arg Met Asn Thr Lys Tyr Asp Glu Asn Asp Lys Leu Ile Arg Glu Val
            980                 985                 990

Lys Val Ile Thr Leu Lys Ser Lys Leu Val Ser Asp Phe Arg Lys Asp
        995                1000                1005

Phe Gln Phe Tyr Lys Val Arg Glu Ile Asn Asn Tyr His His Ala
    1010                1015                1020

His Asp Ala Tyr Leu Asn Ala Val Val Gly Thr Ala Leu Ile Lys
    1025                1030                1035

Lys Tyr Pro Lys Leu Glu Ser Glu Phe Val Tyr Gly Asp Tyr Lys
    1040                1045                1050

Val Tyr Asp Val Arg Lys Met Ile Ala Lys Ser Glu Gln Glu Ile
    1055                1060                1065

Gly Lys Ala Thr Ala Lys Tyr Phe Phe Tyr Ser Asn Ile Met Asn
    1070                1075                1080

Phe Phe Lys Thr Glu Ile Thr Leu Ala Asn Gly Glu Ile Arg Lys
    1085                1090                1095

Arg Pro Leu Ile Glu Thr Asn Gly Glu Thr Gly Glu Ile Val Trp
    1100                1105                1110

Asp Lys Gly Arg Asp Phe Ala Thr Val Arg Lys Val Leu Ser Met
    1115                1120                1125

Pro Gln Val Asn Ile Val Lys Lys Thr Glu Val Gln Thr Gly Gly
    1130                1135                1140

Phe Ser Lys Glu Ser Ile Leu Pro Lys Arg Asn Ser Asp Lys Leu
    1145                1150                1155

Ile Ala Arg Lys Lys Asp Trp Asp Pro Lys Lys Tyr Gly Gly Phe
    1160                1165                1170

Asp Ser Pro Thr Val Ala Tyr Ser Val Leu Val Val Ala Lys Val
    1175                1180                1185

Glu Lys Gly Lys Ser Lys Lys Leu Lys Ser Val Lys Glu Leu Leu
    1190                1195                1200

Gly Ile Thr Ile Met Glu Arg Ser Ser Phe Glu Lys Asn Pro Ile
    1205                1210                1215

Asp Phe Leu Glu Ala Lys Gly Tyr Lys Glu Val Lys Lys Asp Leu
    1220                1225                1230

Ile Ile Lys Leu Pro Lys Tyr Ser Leu Phe Glu Leu Glu Asn Gly
    1235                1240                1245
```

-continued

```
Arg Lys Arg Met Leu Ala Ser Ala Gly Glu Leu Gln Lys Gly Asn
    1250                1255                1260

Glu Leu Ala Leu Pro Ser Lys Tyr Val Asn Phe Leu Tyr Leu Ala
    1265                1270                1275

Ser His Tyr Glu Lys Leu Lys Gly Ser Pro Glu Asp Asn Glu Gln
    1280                1285                1290

Lys Gln Leu Phe Val Glu Gln His Lys His Tyr Leu Asp Glu Ile
    1295                1300                1305

Ile Glu Gln Ile Ser Glu Phe Ser Lys Arg Val Ile Leu Ala Asp
    1310                1315                1320

Ala Asn Leu Asp Lys Val Leu Ser Ala Tyr Asn Lys His Arg Asp
    1325                1330                1335

Lys Pro Ile Arg Glu Gln Ala Glu Asn Ile Ile His Leu Phe Thr
    1340                1345                1350

Leu Thr Asn Leu Gly Ala Pro Ala Ala Phe Lys Tyr Phe Asp Thr
    1355                1360                1365

Thr Ile Asp Arg Lys Arg Tyr Thr Ser Thr Lys Glu Val Leu Asp
    1370                1375                1380

Ala Thr Leu Ile His Gln Ser Ile Thr Gly Leu Tyr Glu Thr Arg
    1385                1390                1395

Ile Asp Leu Ser Gln Leu Gly Gly Asp Lys Arg Pro Ala Ala Thr
    1400                1405                1410

Lys Lys Ala Gly Gln Ala Lys Lys Lys Lys
    1415                1420

<210> SEQ ID NO 10
<211> LENGTH: 1121
<212> TYPE: PRT
<213> ORGANISM: Streptococcus thermophilus

<400> SEQUENCE: 10

Met Ser Asp Leu Val Leu Gly Leu Asp Ile Gly Ile Gly Ser Val
1               5                   10                  15

Val Gly Ile Leu Asn Lys Val Thr Gly Glu Ile Ile His Lys Asn Ser
                20                  25                  30

Arg Ile Phe Pro Ala Ala Gln Ala Glu Asn Asn Leu Val Arg Arg Thr
                35                  40                  45

Asn Arg Gln Gly Arg Arg Leu Ala Arg Arg Lys His Arg Arg Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
                100                 105                 110

Val Lys His Arg Gly Ile Ser Tyr Leu Asp Asp Ala Ser Asp Asp Gly
                115                 120                 125

Asn Ser Ser Val Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
                180                 185                 190
```

-continued

```
Ala Leu Arg Ile Leu Gln Thr Gln Gln Glu Phe Asn Pro Gln Ile Thr
        195                 200                 205
Asp Glu Phe Ile Asn Arg Tyr Leu Glu Ile Leu Thr Gly Lys Arg Lys
    210                 215                 220
Tyr Tyr His Gly Pro Gly Asn Glu Lys Ser Arg Thr Asp Tyr Gly Arg
225                 230                 235                 240
Tyr Arg Thr Ser Gly Glu Thr Leu Asp Asn Ile Phe Gly Ile Leu Ile
                245                 250                 255
Gly Lys Cys Thr Phe Tyr Pro Asp Glu Phe Arg Ala Ala Lys Ala Ser
            260                 265                 270
Tyr Thr Ala Gln Glu Phe Asn Leu Leu Asn Asp Leu Asn Asn Leu Thr
        275                 280                 285
Val Pro Thr Glu Thr Lys Lys Leu Ser Lys Glu Gln Lys Asn Gln Ile
    290                 295                 300
Ile Asn Tyr Val Lys Asn Glu Lys Ala Met Gly Pro Ala Lys Leu Phe
305                 310                 315                 320
Lys Tyr Ile Ala Lys Leu Leu Ser Cys Asp Val Ala Asp Ile Lys Gly
                325                 330                 335
Tyr Arg Ile Asp Lys Ser Gly Lys Ala Glu Ile His Thr Phe Glu Ala
            340                 345                 350
Tyr Arg Lys Met Lys Thr Leu Glu Thr Leu Asp Ile Glu Gln Met Asp
        355                 360                 365
Arg Glu Thr Leu Asp Lys Leu Ala Tyr Val Leu Thr Leu Asn Thr Glu
    370                 375                 380
Arg Glu Gly Ile Gln Glu Ala Leu Glu His Glu Phe Ala Asp Gly Ser
385                 390                 395                 400
Phe Ser Gln Lys Gln Val Asp Glu Leu Val Gln Phe Arg Lys Ala Asn
                405                 410                 415
Ser Ser Ile Phe Gly Lys Gly Trp His Asn Phe Ser Val Lys Leu Met
            420                 425                 430
Met Glu Leu Ile Pro Glu Leu Tyr Glu Thr Ser Glu Glu Gln Met Thr
        435                 440                 445
Ile Leu Thr Arg Leu Gly Lys Gln Lys Thr Thr Ser Ser Ser Asn Lys
    450                 455                 460
Thr Lys Tyr Ile Asp Glu Lys Leu Leu Thr Glu Glu Ile Tyr Asn Pro
465                 470                 475                 480
Val Val Ala Lys Ser Val Arg Gln Ala Ile Lys Ile Val Asn Ala Ala
                485                 490                 495
Ile Lys Glu Tyr Gly Asp Phe Asp Asn Ile Val Ile Glu Met Ala Arg
            500                 505                 510
Glu Thr Asn Glu Asp Asp Glu Lys Lys Ala Ile Gln Lys Ile Gln Lys
        515                 520                 525
Ala Asn Lys Asp Glu Lys Asp Ala Ala Met Leu Lys Ala Ala Asn Gln
    530                 535                 540
Tyr Asn Gly Lys Ala Glu Leu Pro His Ser Val Phe His Gly His Lys
545                 550                 555                 560
Gln Leu Ala Thr Lys Ile Arg Leu Trp His Gln Gln Gly Glu Arg Cys
                565                 570                 575
Leu Tyr Thr Gly Lys Thr Ile Ser Ile His Asp Leu Ile Asn Asn Ser
            580                 585                 590
Asn Gln Phe Glu Val Asp His Ile Leu Pro Leu Ser Ile Thr Phe Asp
        595                 600                 605
```

```
Asp Ser Leu Ala Asn Lys Val Leu Val Tyr Ala Thr Ala Asn Gln Glu
            610                 615                 620

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
                645                 650                 655

Ser Asn Lys Lys Lys Glu Tyr Leu Leu Thr Glu Glu Asp Ile Ser Lys
            660                 665                 670

Phe Asp Val Arg Lys Lys Phe Ile Glu Arg Asn Leu Val Asp Thr Arg
            675                 680                 685

Tyr Ala Ser Arg Val Val Leu Asn Ala Leu Gln Glu His Phe Arg Ala
690                 695                 700

His Lys Ile Asp Thr Lys Val Ser Val Val Arg Gly Gln Phe Thr Ser
705                 710                 715                 720

Gln Leu Arg Arg His Trp Gly Ile Glu Lys Thr Arg Asp Thr Tyr His
                725                 730                 735

His Ala Val Asp Ala Leu Ile Ile Ala Ala Ser Ser Gln Leu Asn
            740                 745                 750

Leu Trp Lys Lys Gln Lys Asn Thr Leu Val Ser Tyr Ser Glu Asp Gln
        755                 760                 765

Leu Leu Asp Ile Glu Thr Gly Glu Leu Ile Ser Asp Asp Glu Tyr Lys
770                 775                 780

Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
            805                 810                 815

Lys Phe Asn Arg Lys Ile Ser Asp Ala Thr Ile Tyr Ala Thr Arg Gln
            820                 825                 830

Ala Lys Val Gly Lys Asp Lys Ala Asp Glu Thr Tyr Val Leu Gly Lys
        835                 840                 845

Ile Lys Asp Ile Tyr Thr Gln Asp Gly Tyr Asp Ala Phe Met Lys Ile
    850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
                885                 890                 895

Gln Ile Asn Asp Lys Gly Lys Glu Val Pro Cys Asn Pro Phe Leu Lys
            900                 905                 910

Tyr Lys Glu Glu His Gly Tyr Ile Arg Lys Tyr Ser Lys Lys Gly Asn
            915                 920                 925

Gly Pro Glu Ile Lys Ser Leu Lys Tyr Tyr Asp Ser Lys Leu Gly Asn
930                 935                 940

His Ile Asp Ile Thr Pro Lys Asp Ser Asn Asn Lys Val Val Leu Gln
945                 950                 955                 960

Ser Val Ser Pro Trp Arg Ala Asp Val Tyr Phe Asn Lys Thr Thr Gly
                965                 970                 975

Lys Tyr Glu Ile Leu Gly Leu Lys Tyr Ala Asp Leu Gln Phe Asp Lys
            980                 985                 990

Gly Thr Gly Thr Tyr Lys Ile Ser  Gln Glu Lys Tyr Asn  Asp Ile Lys
            995                 1000                1005

Lys Lys  Glu Gly Val Asp Ser  Asp Ser Glu Phe Lys  Phe Thr Leu
    1010                1015                1020

Tyr Lys  Asn Asp Leu Leu Leu  Val Lys Asp Thr Glu  Thr Lys Glu
```

-continued

```
              1025                1030                1035

Gln Gln Leu Phe Arg Phe Leu Ser Arg Thr Met Pro Lys Gln Lys
        1040                1045                1050

His Tyr Val Glu Leu Lys Pro Tyr Asp Lys Gln Lys Phe Glu Gly
        1055                1060                1065

Gly Glu Ala Leu Ile Lys Val Leu Gly Asn Val Ala Asn Ser Gly
        1070                1075                1080

Gln Cys Lys Lys Gly Leu Gly Lys Ser Asn Ile Ser Ile Tyr Lys
        1085                1090                1095

Val Arg Thr Asp Val Leu Gly Asn Gln His Ile Ile Lys Asn Glu
        1100                1105                1110

Gly Asp Lys Pro Lys Leu Asp Phe
        1115                1120
```

```
<210> SEQ ID NO 11
<211> LENGTH: 6
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(2)
<223> OTHER INFORMATION: wherein N is any of the nucleotide T, C, A or G
<220> FEATURE:
<221> NAME/KEY: misc_feature
<222> LOCATION: (3)..(3)
<223> OTHER INFORMATION: wherein N is any of the nucleotide A or G
<220> FEATURE:
<221> NAME/KEY: misc_feature
<222> LOCATION: (5)..(5)
<223> OTHER INFORMATION: wherein N is any of the nucleotide A or G

<400> SEQUENCE: 11 nnngna                                                              6

<210> SEQ ID NO 12
<211> LENGTH: 7
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(2)
<223> OTHER INFORMATION: wherein N is any of the nucleotide T, C, A or G
<220> FEATURE:
<221> NAME/KEY: misc_feature
<222> LOCATION: (7)..(7)
<223> OTHER INFORMATION: wherein N is any of the nucleotide A or T

<400> SEQUENCE: 12 nnagaan                                                             7

<210> SEQ ID NO 13
<211> LENGTH: 152
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 13
nnnnnnnnnn nnnnnnnnnn guuuuuguac ucucaagauu uaaguaacug uacaacgaaa      60
```

-continued cuuacacagu uacuuaaauc uugcagaagc uacaaagaua aggcuucaug ccgaaaucaa   120
cacccuguca uuuuauggca ggguguuuuu uu   152

<210> SEQ ID NO 14
<211> LENGTH: 132
<212> TYPE: RNA
<213> ORGANISM: Artificial Sequence
<220> FEATURE:
<223> OTHER INFORMATION: gRNA

<400> SEQUENCE: 14
guuuuuguac ucucaagauu uaaguaacug uacaacgaaa cuuacacagu uacuuaaauc   60
uugcagaagc uacaaagaua aggcuucaug ccgaaaucaa cacccuguca uuuuauggca   120
ggguguuuuu uu   132

<210> SEQ ID NO 15
<211> LENGTH: 1152
<212> TYPE: PRT
<213> ORGANISM: Streptococcus thermophilus

<400> SEQUENCE: 15

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

Asn Arg Gln Gly Arg Arg Leu Ala Arg Arg Lys Lys His Arg Arg Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Asp Gly
        115                 120                 125

Asn Ser Ser Val Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
        195                 200                 205

Asp Glu Phe Ile Asn Arg Tyr Leu Glu Ile Leu Thr Gly Lys Arg Lys
    210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

```
Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
        290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
                340                 345                 350

Tyr Arg Lys Met Lys Thr Leu Glu Thr Leu Asp Ile Glu Gln Met Asp
                355                 360                 365

Arg Glu Thr Leu Asp Lys Leu Ala Tyr Val Leu Thr Leu Asn Thr Glu
        370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
                420                 425                 430

Met Glu Leu Ile Pro Glu Leu Tyr Glu Thr Ser Glu Glu Gln Met Thr
        435                 440                 445

Ile Leu Thr Arg Leu Gly Lys Gln Lys Thr Thr Ser Ser Ser Asn Lys
        450                 455                 460

Thr Lys Tyr Ile Asp Glu Lys Leu Leu Thr Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
                500                 505                 510

Glu Thr Asn Glu Asp Asp Glu Lys Lys Ala Ile Gln Lys Ile Gln Lys
        515                 520                 525

Ala Asn Lys Asp Glu Lys Asp Ala Ala Met Leu Lys Ala Ala Asn Gln
        530                 535                 540

Tyr Asn Gly Lys Ala Glu Leu Pro His Ser Val Phe His Gly His Lys
545                 550                 555                 560

Gln Leu Ala Thr Lys Ile Arg Leu Trp His Gln Gln Gly Glu Arg Cys
                565                 570                 575

Leu Tyr Thr Gly Lys Thr Ile Ser Ile His Asp Leu Ile Asn Asn Ser
                580                 585                 590

Asn Gln Phe Glu Val Asp His Ile Leu Pro Leu Ser Ile Thr Phe Asp
        595                 600                 605

Asp Ser Leu Ala Asn Lys Val Leu Val Tyr Ala Thr Ala Asn Gln Glu
        610                 615                 620

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
                645                 650                 655

Ser Asn Lys Lys Lys Glu Tyr Leu Leu Thr Glu Glu Asp Ile Ser Lys
                660                 665                 670

Phe Asp Val Arg Lys Lys Phe Ile Glu Arg Asn Leu Val Asp Thr Arg
                675                 680                 685
```

```
Tyr Ala Ser Arg Val Val Leu Asn Ala Leu Gln Glu His Phe Arg Ala
    690             695                 700
His Lys Ile Asp Thr Lys Val Ser Val Val Arg Gly Gln Phe Thr Ser
705             710                 715                 720
Gln Leu Arg Arg His Trp Gly Ile Glu Lys Thr Arg Asp Thr Tyr His
            725                 730                 735
His His Ala Val Asp Ala Leu Ile Ile Ala Ala Ser Ser Gln Leu Asn
            740                 745                 750
Leu Trp Lys Gln Lys Asn Thr Leu Val Ser Tyr Ser Glu Asp Gln
        755                 760                 765
Leu Leu Asp Ile Glu Thr Gly Glu Leu Ile Ser Asp Asp Glu Tyr Lys
    770                 775                 780
Glu Ser Val Phe Lys Ala Pro Tyr Gln His Phe Val Asp Thr Leu Lys
785                 790                 795                 800
Ser Lys Glu Phe Glu Asp Ser Ile Leu Phe Ser Tyr Gln Val Asp Ser
                805                 810                 815
Lys Phe Asn Arg Lys Ile Ser Asp Ala Thr Ile Tyr Ala Thr Arg Gln
            820                 825                 830
Ala Lys Val Gly Lys Asp Lys Ala Asp Glu Thr Tyr Val Leu Gly Lys
            835                 840                 845
Ile Lys Asp Ile Tyr Thr Gln Asp Gly Tyr Asp Ala Phe Met Lys Ile
    850                 855                 860
Tyr Lys Lys Asp Lys Ser Lys Phe Leu Met Tyr Arg His Asp Pro Gln
865                 870                 875                 880
Thr Phe Glu Lys Val Ile Glu Pro Ile Leu Glu Asn Tyr Pro Asn Lys
                885                 890                 895
Gln Ile Asn Asp Lys Gly Lys Glu Val Pro Cys Asn Pro Phe Leu Lys
            900                 905                 910
Tyr Lys Glu Glu His Gly Tyr Ile Arg Lys Tyr Ser Lys Lys Gly Asn
            915                 920                 925
Gly Pro Glu Ile Lys Ser Leu Lys Tyr Tyr Asp Ser Lys Leu Gly Asn
    930                 935                 940
His Ile Asp Ile Thr Pro Lys Asp Ser Asn Asn Lys Val Val Leu Gln
945                 950                 955                 960
Ser Val Ser Pro Trp Arg Ala Asp Val Tyr Phe Asn Lys Thr Thr Gly
                965                 970                 975
Lys Tyr Glu Ile Leu Gly Leu Lys Tyr Ala Asp Leu Gln Phe Asp Lys
            980                 985                 990
Gly Thr Gly Thr Tyr Lys Ile Ser Gln Glu Lys Tyr Asn Asp Ile Lys
            995                 1000                1005
Lys Lys Glu Gly Val Asp Ser Asp Ser Glu Phe Lys Phe Thr Leu
    1010                1015                1020
Tyr Lys Asn Asp Leu Leu Leu Val Lys Asp Thr Glu Thr Lys Glu
    1025                1030                1035
Gln Gln Leu Phe Arg Phe Leu Ser Arg Thr Met Pro Lys Gln Lys
    1040                1045                1050
His Tyr Val Glu Leu Lys Pro Tyr Asp Lys Gln Lys Phe Glu Gly
    1055                1060                1065
Gly Glu Ala Leu Ile Lys Val Leu Gly Asn Val Ala Asn Ser Gly
    1070                1075                1080
Gln Cys Lys Lys Gly Leu Gly Lys Ser Asn Ile Ser Ile Tyr Lys
    1085                1090                1095
Val Arg Thr Asp Val Leu Gly Asn Gln His Ile Ile Lys Asn Glu
```

Gly Asp Lys Pro Lys Leu Asp Phe Ala Ala Ala Asp Pro Lys Lys
    1115                1120                1125

Lys Arg Lys Val Asp Pro Lys Lys Arg Lys Val Asp Pro Lys
    1130                1135                1140

Lys Lys Arg Lys Val Asp Thr Ala Ala
    1145                1150

<210> SEQ ID NO 16
<211> LENGTH: 1081
<212> TYPE: PRT
<213> ORGANISM: Neisseria meningitidis

<400> SEQUENCE: 16

Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
            20                  25                  30

Glu Asn Pro Ile Cys Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
        195                 200                 205

Gln Ala Glu Leu Ile Leu Leu Phe Glu Lys Gln Lys Glu Phe Gly Asn
    210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
        275                 280                 285

Leu Glu Gln Gly Ser Glu Arg Pro Leu Thr Asp Thr Glu Arg Ala Thr
    290                 295                 300

Leu Met Asp Glu Pro Tyr Arg Lys Ser Lys Leu Thr Tyr Ala Gln Ala
305                 310                 315                 320

-continued

```
Arg Lys Leu Leu Gly Leu Glu Asp Thr Ala Phe Phe Lys Gly Leu Arg
            325                 330                 335
Tyr Gly Lys Asp Asn Ala Glu Ala Ser Thr Leu Met Glu Met Lys Ala
        340                 345                 350
Tyr His Ala Ile Ser Arg Ala Leu Glu Lys Glu Gly Leu Lys Asp Lys
    355                 360                 365
Lys Ser Pro Leu Asn Leu Ser Pro Glu Leu Gln Asp Glu Ile Gly Thr
370                 375                 380
Ala Phe Ser Leu Phe Lys Thr Asp Glu Asp Ile Thr Gly Arg Leu Lys
385                 390                 395                 400
Asp Arg Ile Gln Pro Glu Ile Leu Glu Ala Leu Leu Lys His Ile Ser
                405                 410                 415
Phe Asp Lys Phe Val Gln Ile Ser Leu Lys Ala Leu Arg Arg Ile Val
            420                 425                 430
Pro Leu Met Glu Gln Gly Lys Arg Tyr Asp Glu Ala Cys Ala Glu Ile
        435                 440                 445
Tyr Gly Asp His Tyr Gly Lys Lys Asn Thr Glu Lys Ile Tyr Leu
    450                 455                 460
Pro Pro Ile Pro Ala Asp Glu Ile Arg Asn Pro Val Val Leu Arg Ala
465                 470                 475                 480
Leu Ser Gln Ala Arg Lys Val Ile Asn Gly Val Val Arg Arg Tyr Gly
                485                 490                 495
Ser Pro Ala Arg Ile His Ile Glu Thr Ala Arg Glu Val Gly Lys Ser
            500                 505                 510
Phe Lys Asp Arg Lys Glu Ile Glu Lys Arg Gln Glu Glu Asn Arg Lys
        515                 520                 525
Asp Arg Glu Lys Ala Ala Ala Lys Phe Arg Glu Tyr Phe Pro Asn Phe
    530                 535                 540
Val Gly Glu Pro Lys Ser Lys Asp Ile Leu Lys Leu Arg Leu Tyr Glu
545                 550                 555                 560
Gln Gln His Gly Lys Cys Leu Tyr Ser Gly Lys Glu Ile Asn Leu Gly
                565                 570                 575
Arg Leu Asn Glu Lys Gly Tyr Val Glu Ile Asp His Ala Leu Pro Phe
            580                 585                 590
Ser Arg Thr Trp Asp Asp Ser Phe Asn Asn Lys Val Leu Val Leu Gly
        595                 600                 605
Ser Glu Asn Gln Asn Lys Gly Asn Gln Thr Pro Tyr Glu Tyr Phe Asn
    610                 615                 620
Gly Lys Asp Asn Ser Arg Glu Trp Gln Glu Phe Lys Ala Arg Val Glu
625                 630                 635                 640
Thr Ser Arg Phe Pro Arg Ser Lys Lys Gln Arg Ile Leu Leu Gln Lys
                645                 650                 655
Phe Asp Glu Asp Gly Phe Lys Glu Arg Asn Leu Asn Asp Thr Arg Tyr
            660                 665                 670
Val Asn Arg Phe Leu Cys Phe Val Ala Asp Arg Met Arg Leu Thr Gly
        675                 680                 685
Lys Gly Lys Lys Arg Val Phe Ala Ser Asn Gly Gln Ile Thr Asn Leu
    690                 695                 700
Leu Arg Gly Phe Trp Gly Leu Arg Lys Val Arg Ala Glu Asn Asp Arg
705                 710                 715                 720
His His Ala Leu Asp Ala Val Val Val Ala Cys Ser Thr Val Ala Met
                725                 730                 735
Gln Gln Lys Ile Thr Arg Phe Val Arg Tyr Lys Glu Met Asn Ala Phe
```

```
                740                 745                 750
Asp Gly Lys Thr Ile Asp Lys Glu Thr Gly Glu Val Leu His Gln Lys
            755                 760                 765
Thr His Phe Pro Gln Pro Trp Glu Phe Phe Ala Gln Glu Val Met Ile
        770                 775                 780
Arg Val Phe Gly Lys Pro Asp Gly Lys Pro Glu Phe Glu Glu Ala Asp
785                 790                 795                 800
Thr Pro Glu Lys Leu Arg Thr Leu Leu Ala Glu Lys Leu Ser Ser Arg
                805                 810                 815
Pro Glu Ala Val His Glu Tyr Val Thr Pro Leu Phe Val Ser Arg Ala
            820                 825                 830
Pro Asn Arg Lys Met Ser Gly Gln Gly His Met Glu Thr Val Lys Ser
        835                 840                 845
Ala Lys Arg Leu Asp Glu Gly Val Ser Val Leu Arg Val Pro Leu Thr
    850                 855                 860
Gln Leu Lys Leu Lys Asp Leu Glu Lys Met Val Asn Arg Glu Arg Glu
865                 870                 875                 880
Pro Lys Leu Tyr Glu Ala Leu Lys Ala Arg Leu Glu Ala His Lys Asp
                885                 890                 895
Asp Pro Ala Lys Ala Phe Ala Glu Pro Phe Tyr Lys Tyr Asp Lys Ala
            900                 905                 910
Gly Asn Arg Thr Gln Gln Val Lys Ala Val Arg Val Glu Gln Val Gln
        915                 920                 925
Lys Thr Gly Val Trp Val Arg Asn His Asn Gly Ile Ala Asp Asn Ala
    930                 935                 940
Thr Met Val Arg Val Asp Val Phe Glu Lys Gly Asp Lys Tyr Tyr Leu
945                 950                 955                 960
Val Pro Ile Tyr Ser Trp Gln Val Ala Lys Gly Ile Leu Pro Asp Arg
                965                 970                 975
Ala Val Val Gln Gly Lys Asp Glu Glu Asp Trp Gln Leu Ile Asp Asp
            980                 985                 990
Ser Phe Asn Phe Lys Phe Ser Leu His Pro Asn Asp Leu Val Glu Val
        995                 1000                1005
Ile Thr Lys Lys Ala Arg Met Phe Gly Tyr Phe Ala Ser Cys His
    1010                1015                1020
Arg Gly Thr Gly Asn Ile Asn Ile Arg Ile His Asp Leu Asp His
    1025                1030                1035
Lys Ile Gly Lys Asn Gly Ile Leu Glu Gly Ile Gly Val Lys Thr
    1040                1045                1050
Ala Leu Ser Phe Gln Lys Tyr Gln Ile Asp Glu Leu Gly Lys Glu
    1055                1060                1065
Ile Arg Pro Cys Arg Leu Lys Lys Arg Pro Pro Val Arg
    1070                1075                1080

<210> SEQ ID NO 17
<211> LENGTH: 8
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(4)
<223> OTHER INFORMATION: wherein N is any of the nucleotide T, C, A or G
<220> FEATURE:
<221> NAME/KEY: misc_feature
<222> LOCATION: (7)..(8)
```

-continued

```
<223> OTHER INFORMATION: wherein N is any of the nucleotide T, C, A or G

<400> SEQUENCE: 17 nnnngann                                                                    8

<210> SEQ ID NO 18
<211> LENGTH: 8
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(4)
<223> OTHER INFORMATION: wherein N is any of the nucleotide T, C, A or G

<400> SEQUENCE: 18 nnnngatt                                                                    8

<210> SEQ ID NO 19
<211> LENGTH: 145
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(24)
<223> OTHER INFORMATION: wherein N is any of the nucleotide U, C, A or G

<400> SEQUENCE: 19
nnnnnnnnnn nnnnnnnnnn nnnnguugua gcucccuuuc ucauuuggga aacgaaauga         60
gaaccguugc uacaauaagg ccgucugaaa agaugugccg caacgcucug cccccuuaaag       120 cuucugcuuu aaggggcauc guuua                                              145

<210> SEQ ID NO 20
<211> LENGTH: 121
<212> TYPE: RNA
<213> ORGANISM: Artificial Sequence
<220> FEATURE:
<223> OTHER INFORMATION: gRNA

<400> SEQUENCE: 20
guuguagcuc ccuuucucau uuggaaacg aaaugagaac cguugcuaca auaaggccgu          60
cugaaaagau gugccgcaac gcucugcccc uuaaagcuuc ugcuuuaagg ggcaucguuu        120
a                                                                       121

<210> SEQ ID NO 21
<211> LENGTH: 1113
<212> TYPE: PRT
<213> ORGANISM: Neisseria meningitidis

<400> SEQUENCE: 21
```

Met Ala Ala Phe Lys Pro Asn Pro Ile Asn Tyr Ile Leu Gly Leu Asp
1               5                   10                  15

Ile Gly Ile Ala Ser Val Gly Trp Ala Met Val Glu Ile Asp Glu Asp
                20                  25                  30

Glu Asn Pro Ile Cys Leu Ile Asp Leu Gly Val Arg Val Phe Glu Arg
            35                  40                  45

Ala Glu Val Pro Lys Thr Gly Asp Ser Leu Ala Met Ala Arg Arg Leu
        50                  55                  60

Ala Arg Ser Val Arg Arg Leu Thr Arg Arg Arg Ala His Arg Leu Leu

```
            65                  70                  75                  80
        Arg Ala Arg Arg Leu Leu Lys Arg Glu Gly Val Leu Gln Ala Ala Asp
                         85                  90                  95

Phe Asp Glu Asn Gly Leu Ile Lys Ser Leu Pro Asn Thr Pro Trp Gln
                        100                 105                 110

Leu Arg Ala Ala Ala Leu Asp Arg Lys Leu Thr Pro Leu Glu Trp Ser
                        115                 120                 125

Ala Val Leu Leu His Leu Ile Lys His Arg Gly Tyr Leu Ser Gln Arg
                        130                 135                 140

Lys Asn Glu Gly Glu Thr Ala Asp Lys Glu Leu Gly Ala Leu Leu Lys
        145                 150                 155                 160

Gly Val Ala Asp Asn Ala His Ala Leu Gln Thr Gly Asp Phe Arg Thr
                        165                 170                 175

Pro Ala Glu Leu Ala Leu Asn Lys Phe Glu Lys Glu Ser Gly His Ile
                        180                 185                 190

Arg Asn Gln Arg Gly Asp Tyr Ser His Thr Phe Ser Arg Lys Asp Leu
                        195                 200                 205

Gln Ala Glu Leu Ile Leu Leu Phe Glu Lys Gln Lys Glu Phe Gly Asn
                        210                 215                 220

Pro His Val Ser Gly Gly Leu Lys Glu Gly Ile Glu Thr Leu Leu Met
        225                 230                 235                 240

Thr Gln Arg Pro Ala Leu Ser Gly Asp Ala Val Gln Lys Met Leu Gly
                        245                 250                 255

His Cys Thr Phe Glu Pro Ala Glu Pro Lys Ala Ala Lys Asn Thr Tyr
                        260                 265                 270

Thr Ala Glu Arg Phe Ile Trp Leu Thr Lys Leu Asn Asn Leu Arg Ile
                        275                 280                 285

Leu Glu Gln Gly Ser Glu Arg Pro Leu Thr Asp Thr Glu Arg Ala Thr
                        290                 295                 300

Leu Met Asp Glu Pro Tyr Arg Lys Ser Lys Leu Thr Tyr Ala Gln Ala
        305                 310                 315                 320

Arg Lys Leu Leu Gly Leu Glu Asp Thr Ala Phe Phe Lys Gly Leu Arg
                        325                 330                 335

Tyr Gly Lys Asp Asn Ala Glu Ala Ser Thr Leu Met Glu Met Lys Ala
                        340                 345                 350

Tyr His Ala Ile Ser Arg Ala Leu Glu Lys Glu Gly Leu Lys Asp Lys
                        355                 360                 365

Lys Ser Pro Leu Asn Leu Ser Pro Glu Leu Gln Asp Glu Ile Gly Thr
                        370                 375                 380

Ala Phe Ser Leu Phe Lys Thr Asp Glu Asp Ile Thr Gly Arg Leu Lys
        385                 390                 395                 400

Asp Arg Ile Gln Pro Glu Ile Leu Glu Ala Leu Leu Lys His Ile Ser
                        405                 410                 415

Phe Asp Lys Phe Val Gln Ile Ser Leu Lys Ala Leu Arg Arg Ile Val
                        420                 425                 430

Pro Leu Met Glu Gln Gly Lys Arg Tyr Asp Glu Ala Cys Ala Glu Ile
                        435                 440                 445

Tyr Gly Asp His Tyr Gly Lys Lys Asn Thr Glu Lys Ile Tyr Leu
                        450                 455                 460

Pro Pro Ile Pro Ala Asp Glu Ile Arg Asn Pro Val Val Leu Arg Ala
        465                 470                 475                 480

Leu Ser Gln Ala Arg Lys Val Ile Asn Gly Val Val Arg Arg Tyr Gly
                        485                 490                 495
```

-continued

```
Ser Pro Ala Arg Ile His Ile Glu Thr Ala Arg Glu Val Gly Lys Ser
            500                 505                 510
Phe Lys Asp Arg Lys Glu Ile Glu Lys Arg Gln Glu Glu Asn Arg Lys
        515                 520                 525
Asp Arg Glu Lys Ala Ala Lys Phe Arg Glu Tyr Phe Pro Asn Phe
    530                 535                 540
Val Gly Glu Pro Lys Ser Lys Asp Ile Leu Lys Leu Arg Leu Tyr Glu
545                 550                 555                 560
Gln Gln His Gly Lys Cys Leu Tyr Ser Gly Lys Glu Ile Asn Leu Gly
                565                 570                 575
Arg Leu Asn Glu Lys Gly Tyr Val Glu Ile Asp His Ala Leu Pro Phe
            580                 585                 590
Ser Arg Thr Trp Asp Asp Ser Phe Asn Asn Lys Val Leu Val Leu Gly
        595                 600                 605
Ser Glu Asn Gln Asn Lys Gly Asn Gln Thr Pro Tyr Glu Tyr Phe Asn
    610                 615                 620
Gly Lys Asp Asn Ser Arg Glu Trp Gln Glu Phe Lys Ala Arg Val Glu
625                 630                 635                 640
Thr Ser Arg Phe Pro Arg Ser Lys Lys Gln Arg Ile Leu Leu Gln Lys
                645                 650                 655
Phe Asp Glu Asp Gly Phe Lys Glu Arg Asn Leu Asn Asp Thr Arg Tyr
            660                 665                 670
Val Asn Arg Phe Leu Cys Gln Phe Val Ala Asp Arg Met Arg Leu Thr
        675                 680                 685
Gly Lys Gly Lys Lys Arg Val Phe Ala Ser Asn Gly Gln Ile Thr Asn
    690                 695                 700
Leu Leu Arg Gly Phe Trp Gly Leu Arg Lys Val Arg Ala Glu Asn Asp
705                 710                 715                 720
Arg His His Ala Leu Asp Ala Val Val Ala Cys Ser Thr Val Ala
                725                 730                 735
Met Gln Gln Lys Ile Thr Arg Phe Val Arg Tyr Lys Glu Met Asn Ala
            740                 745                 750
Phe Asp Gly Lys Thr Ile Asp Lys Glu Thr Gly Glu Val Leu His Gln
        755                 760                 765
Lys Thr His Phe Pro Gln Pro Trp Glu Phe Phe Ala Gln Glu Val Met
    770                 775                 780
Ile Arg Val Phe Gly Lys Pro Asp Gly Lys Pro Glu Phe Glu Glu Ala
785                 790                 795                 800
Asp Thr Pro Glu Lys Leu Arg Thr Leu Leu Ala Glu Lys Leu Ser Ser
                805                 810                 815
Arg Pro Glu Ala Val His Glu Tyr Val Thr Pro Leu Phe Val Ser Arg
            820                 825                 830
Ala Pro Asn Arg Lys Met Ser Gly Gln Gly His Met Glu Thr Val Lys
        835                 840                 845
Ser Ala Lys Arg Leu Asp Glu Gly Val Ser Val Leu Arg Val Pro Leu
    850                 855                 860
Thr Gln Leu Lys Leu Lys Asp Leu Glu Lys Met Val Asn Arg Glu Arg
865                 870                 875                 880
Glu Pro Lys Leu Tyr Glu Ala Leu Lys Ala Arg Leu Glu Ala His Lys
                885                 890                 895
Asp Asp Pro Ala Lys Ala Phe Ala Glu Pro Phe Tyr Lys Tyr Asp Lys
            900                 905                 910
```

Ala Gly Asn Arg Thr Gln Gln Val Lys Ala Val Arg Val Glu Gln Val
            915                 920                 925

Gln Lys Thr Gly Val Trp Val Arg Asn His Asn Gly Ile Ala Asp Asn
        930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Asp Trp Gln Leu Ile Asp
            980                 985                 990

Asp Ser Phe Asn Phe Lys Phe Ser Leu His Pro Asn Asp Leu Val Glu
        995                 1000                1005

Val Ile Thr Lys Lys Ala Arg Met Phe Gly Tyr Phe Ala Ser Cys
    1010                1015                1020

His Arg Gly Thr Gly Asn Ile Asn Ile Arg Ile His Asp Leu Asp
    1025                1030                1035

His Lys Ile Gly Lys Asn Gly Ile Leu Glu Gly Ile Gly Val Lys
    1040                1045                1050

Thr Ala Leu Ser Phe Gln Lys Tyr Gln Ile Asp Glu Leu Gly Lys
    1055                1060                1065

Glu Ile Arg Pro Cys Arg Leu Lys Lys Arg Pro Val Arg Ala
    1070                1075                1080

Ala Ala Asp Pro Lys Lys Lys Arg Lys Val Asp Pro Lys Lys Lys
    1085                1090                1095

Arg Lys Val Asp Pro Lys Lys Lys Arg Lys Val Asp Thr Ala Ala
    1100                1105                1110

<210> SEQ ID NO 22
<211> LENGTH: 1395
<212> TYPE: PRT
<213> ORGANISM: Treponema denticola

<400> SEQUENCE: 22

Met Lys Lys Glu Ile Lys Asp Tyr Phe Leu Gly Leu Asp Val Gly Thr
1               5                   10                  15

Gly Ser Val Gly Trp Ala Val Thr Asp Thr Asp Tyr Lys Leu Leu Lys
            20                  25                  30

Ala Asn Arg Lys Asp Leu Trp Gly Met Arg Cys Phe Glu Thr Ala Glu
        35                  40                  45

Thr Ala Glu Val Arg Arg Leu His Arg Gly Ala Arg Arg Ile Glu
    50                  55                  60

Arg Arg Lys Lys Arg Ile Lys Leu Leu Gln Glu Leu Phe Ser Gln Glu
65                  70                  75                  80

Ile Ala Lys Thr Asp Glu Gly Phe Phe Gln Arg Met Lys Glu Ser Pro
                85                  90                  95

Phe Tyr Ala Glu Asp Lys Thr Ile Leu Gln Glu Asn Thr Leu Phe Asn
            100                 105                 110

Asp Lys Asp Phe Ala Asp Lys Thr Tyr His Lys Ala Tyr Pro Thr Ile
        115                 120                 125

Asn His Leu Ile Lys Ala Trp Ile Glu Asn Lys Val Lys Pro Asp Pro
    130                 135                 140

Arg Leu Leu Tyr Leu Ala Cys His Asn Ile Ile Lys Lys Arg Gly His
145                 150                 155                 160

Phe Leu Phe Glu Gly Asp Phe Asp Ser Glu Asn Gln Phe Asp Thr Ser
                165                 170                 175

```
Ile Gln Ala Leu Phe Glu Tyr Leu Arg Glu Asp Met Glu Val Asp Ile
            180                 185                 190

Asp Ala Asp Ser Gln Lys Val Lys Glu Ile Leu Lys Asp Ser Ser Leu
        195                 200                 205

Lys Asn Ser Glu Lys Gln Ser Arg Leu Asn Lys Ile Leu Gly Leu Lys
    210                 215                 220

Pro Ser Asp Lys Gln Lys Lys Ala Ile Thr Asn Leu Ile Ser Gly Asn
225                 230                 235                 240

Lys Ile Asn Phe Ala Asp Leu Tyr Asp Asn Pro Asp Leu Lys Asp Ala
                245                 250                 255

Glu Lys Asn Ser Ile Ser Phe Ser Lys Asp Asp Phe Asp Ala Leu Ser
            260                 265                 270

Asp Asp Leu Ala Ser Ile Leu Gly Asp Ser Phe Glu Leu Leu Leu Lys
        275                 280                 285

Ala Lys Ala Val Tyr Asn Cys Ser Val Leu Ser Lys Val Ile Gly Asp
    290                 295                 300

Glu Gln Tyr Leu Ser Phe Ala Lys Val Lys Ile Tyr Glu Lys His Lys
305                 310                 315                 320

Thr Asp Leu Thr Lys Leu Lys Asn Val Ile Lys Lys His Phe Pro Lys
                325                 330                 335

Asp Tyr Lys Lys Val Phe Gly Tyr Asn Lys Asn Glu Lys Asn Asn Asn
            340                 345                 350

Asn Tyr Ser Gly Tyr Val Gly Val Cys Lys Thr Lys Ser Lys Lys Leu
        355                 360                 365

Ile Ile Asn Asn Ser Val Asn Gln Glu Asp Phe Tyr Lys Phe Leu Lys
    370                 375                 380

Thr Ile Leu Ser Ala Lys Ser Glu Ile Lys Glu Val Asn Asp Ile Leu
385                 390                 395                 400

Thr Glu Ile Glu Thr Gly Thr Phe Leu Pro Lys Gln Ile Ser Lys Ser
                405                 410                 415

Asn Ala Glu Ile Pro Tyr Gln Leu Arg Lys Met Glu Leu Glu Lys Ile
            420                 425                 430

Leu Ser Asn Ala Glu Lys His Phe Ser Phe Leu Lys Gln Lys Asp Glu
        435                 440                 445

Lys Gly Leu Ser His Ser Glu Lys Ile Ile Met Leu Leu Thr Phe Lys
    450                 455                 460

Ile Pro Tyr Tyr Ile Gly Pro Ile Asn Asp Asn His Lys Lys Phe Phe
465                 470                 475                 480

Pro Asp Arg Cys Trp Val Val Lys Lys Glu Lys Ser Pro Ser Gly Lys
                485                 490                 495

Thr Thr Pro Trp Asn Phe Phe Asp His Ile Asp Lys Glu Lys Thr Ala
            500                 505                 510

Glu Ala Phe Ile Thr Ser Arg Thr Asn Phe Cys Thr Tyr Leu Val Gly
        515                 520                 525

Glu Ser Val Leu Pro Lys Ser Ser Leu Leu Tyr Ser Glu Tyr Thr Val
    530                 535                 540

Leu Asn Glu Ile Asn Asn Leu Gln Ile Ile Asp Gly Lys Asn Ile
545                 550                 555                 560

Cys Asp Ile Lys Leu Lys Gln Lys Ile Tyr Glu Asp Leu Phe Lys Lys
                565                 570                 575

Tyr Lys Lys Ile Thr Gln Lys Gln Ile Ser Thr Phe Ile Lys His Glu
            580                 585                 590
```

```
Gly Ile Cys Asn Lys Thr Asp Glu Val Ile Ile Leu Gly Ile Asp Lys
            595                 600                 605

Glu Cys Thr Ser Ser Leu Lys Ser Tyr Ile Glu Leu Lys Asn Ile Phe
    610                 615                 620

Gly Lys Gln Val Asp Glu Ile Ser Thr Lys Asn Met Leu Glu Glu Ile
625                 630                 635                 640

Ile Arg Trp Ala Thr Ile Tyr Asp Glu Gly Glu Gly Lys Thr Ile Leu
                645                 650                 655

Lys Thr Lys Ile Lys Ala Glu Tyr Gly Lys Tyr Cys Ser Asp Glu Gln
                660                 665                 670

Ile Lys Lys Ile Leu Asn Leu Lys Phe Ser Gly Trp Gly Arg Leu Ser
            675                 680                 685

Arg Lys Phe Leu Glu Thr Val Thr Ser Glu Met Pro Gly Phe Ser Glu
    690                 695                 700

Pro Val Asn Ile Ile Thr Ala Met Arg Glu Thr Gln Asn Asn Leu Met
705                 710                 715                 720

Glu Leu Leu Ser Ser Glu Phe Thr Phe Thr Glu Asn Ile Lys Lys Ile
                725                 730                 735

Asn Ser Gly Phe Glu Asp Ala Glu Lys Gln Phe Ser Tyr Asp Gly Leu
                740                 745                 750

Val Lys Pro Leu Phe Leu Ser Pro Ser Val Lys Lys Met Leu Trp Gln
            755                 760                 765

Thr Leu Lys Leu Val Lys Glu Ile Ser His Ile Thr Gln Ala Pro Pro
770                 775                 780

Lys Lys Ile Phe Ile Glu Met Ala Lys Gly Ala Glu Leu Glu Pro Ala
785                 790                 795                 800

Arg Thr Lys Thr Arg Leu Lys Ile Leu Gln Asp Leu Tyr Asn Asn Cys
                805                 810                 815

Lys Asn Asp Ala Asp Ala Phe Ser Ser Glu Ile Lys Asp Leu Ser Gly
                820                 825                 830

Lys Ile Glu Asn Glu Asp Asn Leu Arg Leu Arg Ser Asp Lys Leu Tyr
            835                 840                 845

Leu Tyr Tyr Thr Gln Leu Gly Lys Cys Met Tyr Cys Gly Lys Pro Ile
    850                 855                 860

Glu Ile Gly His Val Phe Asp Thr Ser Asn Tyr Asp Ile Asp His Ile
865                 870                 875                 880

Tyr Pro Gln Ser Lys Ile Lys Asp Asp Ser Ile Ser Asn Arg Val Leu
                885                 890                 895

Val Cys Ser Ser Cys Asn Lys Asn Lys Glu Asp Lys Tyr Pro Leu Lys
                900                 905                 910

Ser Glu Ile Gln Ser Lys Gln Arg Gly Phe Trp Asn Phe Leu Gln Arg
            915                 920                 925

Asn Asn Phe Ile Ser Leu Glu Lys Leu Asn Arg Leu Thr Arg Ala Thr
    930                 935                 940

Pro Ile Ser Asp Asp Glu Thr Ala Lys Phe Ile Ala Arg Gln Leu Val
945                 950                 955                 960

Glu Thr Arg Gln Ala Thr Lys Val Ala Ala Lys Val Leu Glu Lys Met
                965                 970                 975

Phe Pro Glu Thr Lys Ile Val Tyr Ser Lys Ala Glu Thr Val Ser Met
                980                 985                 990

Phe Arg Asn Lys Phe Asp Ile Val  Lys Cys Arg Glu Ile  Asn Asp Phe
            995                 1000                 1005

His His  Ala His Asp Ala Tyr  Leu Asn Ile Val Val  Gly Asn Val
```

-continued

```
           1010                1015                1020
Tyr Asn Thr Lys Phe Thr Asn Asn Pro Trp Asn Phe Ile Lys Glu
           1025                1030                1035
Lys Arg Asp Asn Pro Lys Ile Ala Asp Thr Tyr Asn Tyr Tyr Lys
           1040                1045                1050
Val Phe Asp Tyr Asp Val Lys Arg Asn Asn Ile Thr Ala Trp Glu
           1055                1060                1065
Lys Gly Lys Thr Ile Ile Thr Val Lys Asp Met Leu Lys Arg Asn
           1070                1075                1080
Thr Pro Ile Tyr Thr Arg Gln Ala Ala Cys Lys Lys Gly Glu Leu
           1085                1090                1095
Phe Asn Gln Thr Ile Met Lys Lys Gly Leu Gly Gln His Pro Leu
           1100                1105                1110
Lys Lys Glu Gly Pro Phe Ser Asn Ile Ser Lys Tyr Gly Gly Tyr
           1115                1120                1125
Asn Lys Val Ser Ala Ala Tyr Tyr Thr Leu Ile Glu Tyr Glu Glu
           1130                1135                1140
Lys Gly Asn Lys Ile Arg Ser Leu Glu Thr Ile Pro Leu Tyr Leu
           1145                1150                1155
Val Lys Asp Ile Gln Lys Asp Gln Asp Val Leu Lys Ser Tyr Leu
           1160                1165                1170
Thr Asp Leu Leu Gly Lys Lys Glu Phe Lys Ile Leu Val Pro Lys
           1175                1180                1185
Ile Lys Ile Asn Ser Leu Leu Lys Ile Asn Gly Phe Pro Cys His
           1190                1195                1200
Ile Thr Gly Lys Thr Asn Asp Ser Phe Leu Leu Arg Pro Ala Val
           1205                1210                1215
Gln Phe Cys Cys Ser Asn Asn Glu Val Leu Tyr Phe Lys Lys Ile
           1220                1225                1230
Ile Arg Phe Ser Glu Ile Arg Ser Gln Arg Glu Lys Ile Gly Lys
           1235                1240                1245
Thr Ile Ser Pro Tyr Glu Asp Leu Ser Phe Arg Ser Tyr Ile Lys
           1250                1255                1260
Glu Asn Leu Trp Lys Lys Thr Lys Asn Asp Glu Ile Gly Glu Lys
           1265                1270                1275
Glu Phe Tyr Asp Leu Leu Gln Lys Lys Asn Leu Glu Ile Tyr Asp
           1280                1285                1290
Met Leu Leu Thr Lys His Lys Asp Thr Ile Tyr Lys Lys Arg Pro
           1295                1300                1305
Asn Ser Ala Thr Ile Asp Ile Leu Val Lys Gly Lys Glu Lys Phe
           1310                1315                1320
Lys Ser Leu Ile Ile Glu Asn Gln Phe Glu Val Ile Leu Glu Ile
           1325                1330                1335
Leu Lys Leu Phe Ser Ala Thr Arg Asn Val Ser Asp Leu Gln His
           1340                1345                1350
Ile Gly Gly Ser Lys Tyr Ser Gly Val Ala Lys Ile Gly Asn Lys
           1355                1360                1365
Ile Ser Ser Leu Asp Asn Cys Ile Leu Ile Tyr Gln Ser Ile Thr
           1370                1375                1380
Gly Ile Phe Glu Lys Arg Ile Asp Leu Leu Lys Val
           1385                1390                1395

<210> SEQ ID NO 23
```

```
<211> LENGTH: 6
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(1)
<223> OTHER INFORMATION: wherein N is any of the nucleotide T, C, A or G
<220> FEATURE:
<221> NAME/KEY: misc_feature
<222> LOCATION: (6)..(6)
<223> OTHER INFORMATION: wherein N is any of the nucleotide T, C, A or G

<400> SEQUENCE: 23 naaaan                                                                    6

<210> SEQ ID NO 24
<211> LENGTH: 1426
<212> TYPE: PRT
<213> ORGANISM: Treponema denticola

<400> SEQUENCE: 24
```

Met Lys Lys Glu Ile Lys Asp Tyr Phe Leu Gly Leu Asp Val Gly Thr
1               5                   10                  15

Gly Ser Val Gly Trp Ala Val Thr Asp Thr Asp Tyr Lys Leu Leu Lys
            20                  25                  30

Ala Asn Arg Lys Asp Leu Trp Gly Met Arg Cys Phe Glu Thr Ala Glu
        35                  40                  45

Thr Ala Glu Val Arg Arg Leu His Arg Gly Ala Arg Arg Arg Ile Glu
    50                  55                  60

Arg Arg Lys Lys Arg Ile Lys Leu Leu Gln Glu Leu Phe Ser Gln Glu
65                  70                  75                  80

Ile Ala Lys Thr Asp Glu Gly Phe Phe Gln Arg Met Lys Glu Ser Pro
                85                  90                  95

Phe Tyr Ala Glu Asp Lys Thr Ile Leu Gln Glu Asn Thr Leu Phe Asn
            100                 105                 110

Asp Lys Asp Phe Ala Asp Lys Thr Tyr His Lys Ala Tyr Pro Thr Ile
        115                 120                 125

Asn His Leu Ile Lys Ala Trp Ile Glu Asn Lys Val Lys Pro Asp Pro
    130                 135                 140

Arg Leu Leu Tyr Leu Ala Cys His Asn Ile Ile Lys Lys Arg Gly His
145                 150                 155                 160

Phe Leu Phe Glu Gly Asp Phe Asp Ser Glu Asn Gln Phe Asp Thr Ser
                165                 170                 175

Ile Gln Ala Leu Phe Glu Tyr Leu Arg Glu Asp Met Glu Val Asp Ile
            180                 185                 190

Asp Ala Asp Ser Gln Lys Val Lys Glu Ile Leu Lys Asp Ser Ser Leu
        195                 200                 205

Lys Asn Ser Glu Lys Gln Ser Arg Leu Asn Lys Ile Leu Gly Leu Lys
    210                 215                 220

Pro Ser Asp Lys Gln Lys Lys Ala Ile Thr Asn Leu Ile Ser Gly Asn
225                 230                 235                 240

Lys Ile Asn Phe Ala Asp Leu Tyr Asp Asn Pro Asp Leu Lys Asp Ala
                245                 250                 255

Glu Lys Asn Ser Ile Ser Phe Ser Lys Asp Asp Phe Asp Ala Leu Ser
            260                 265                 270

Asp Asp Leu Ala Ser Ile Leu Gly Asp Ser Phe Glu Leu Leu Leu Lys
        275                 280                 285

```
Ala Lys Ala Val Tyr Asn Cys Ser Val Leu Ser Lys Val Ile Gly Asp
290                 295                 300

Glu Gln Tyr Leu Ser Phe Ala Lys Val Lys Ile Tyr Glu Lys His Lys
305                 310                 315                 320

Thr Asp Leu Thr Lys Leu Lys Asn Val Ile Lys Lys His Phe Pro Lys
            325                 330                 335

Asp Tyr Lys Lys Val Phe Gly Tyr Asn Lys Asn Glu Lys Asn Asn Asn
            340                 345                 350

Asn Tyr Ser Gly Tyr Val Gly Val Cys Lys Thr Lys Ser Lys Lys Leu
            355                 360                 365

Ile Ile Asn Asn Ser Val Asn Gln Glu Asp Phe Tyr Lys Phe Leu Lys
370                 375                 380

Thr Ile Leu Ser Ala Lys Ser Glu Ile Lys Glu Val Asn Asp Ile Leu
385                 390                 395                 400

Thr Glu Ile Glu Thr Gly Thr Phe Leu Pro Lys Gln Ile Ser Lys Ser
            405                 410                 415

Asn Ala Glu Ile Pro Tyr Gln Leu Arg Lys Met Glu Leu Glu Lys Ile
            420                 425                 430

Leu Ser Asn Ala Glu Lys His Phe Ser Phe Leu Lys Gln Lys Asp Glu
            435                 440                 445

Lys Gly Leu Ser His Ser Glu Lys Ile Ile Met Leu Leu Thr Phe Lys
450                 455                 460

Ile Pro Tyr Tyr Ile Gly Pro Ile Asn Asp Asn His Lys Lys Phe Phe
465                 470                 475                 480

Pro Asp Arg Cys Trp Val Val Lys Lys Glu Lys Ser Pro Ser Gly Lys
            485                 490                 495

Thr Thr Pro Trp Asn Phe Phe Asp His Ile Asp Lys Gly Lys Thr Ala
            500                 505                 510

Glu Ala Phe Ile Thr Ser Arg Thr Asn Phe Cys Thr Tyr Leu Val Gly
            515                 520                 525

Glu Ser Val Leu Pro Lys Ser Ser Leu Leu Tyr Ser Glu Tyr Thr Val
530                 535                 540

Leu Asn Glu Ile Asn Asn Leu Gln Ile Ile Asp Gly Lys Asn Ile
545                 550                 555                 560

Cys Asp Ile Lys Leu Lys Gln Lys Ile Tyr Glu Asp Leu Phe Lys Lys
            565                 570                 575

Tyr Lys Lys Ile Thr Gln Lys Gln Ile Ser Thr Phe Ile Lys His Glu
            580                 585                 590

Gly Ile Cys Asn Lys Thr Asp Glu Val Ile Ile Leu Gly Ile Asp Lys
            595                 600                 605

Glu Cys Thr Ser Ser Leu Lys Ser Tyr Ile Glu Leu Lys Asn Ile Phe
610                 615                 620

Gly Lys Gln Val Asp Glu Ile Ser Thr Lys Asn Met Leu Glu Glu Ile
625                 630                 635                 640

Ile Arg Trp Ala Thr Ile Tyr Asp Glu Gly Glu Gly Lys Thr Ile Leu
            645                 650                 655

Lys Thr Lys Ile Lys Ala Glu Tyr Gly Lys Tyr Cys Ser Asp Glu Gln
            660                 665                 670

Ile Lys Lys Ile Leu Asn Leu Lys Phe Ser Gly Trp Gly Arg Leu Ser
            675                 680                 685

Arg Lys Phe Leu Glu Thr Val Thr Ser Glu Met Pro Gly Phe Ser Glu
690                 695                 700
```

```
Pro Val Asn Ile Ile Thr Ala Met Arg Glu Thr Gln Asn Asn Leu Met
705                 710                 715                 720

Glu Leu Leu Ser Ser Glu Phe Thr Phe Thr Glu Asn Ile Lys Lys Ile
            725                 730                 735

Asn Ser Gly Phe Glu Asp Ala Glu Lys Gln Phe Ser Tyr Asp Gly Leu
                740                 745                 750

Val Lys Pro Leu Phe Leu Ser Pro Ser Val Lys Lys Met Leu Trp Gln
            755                 760                 765

Thr Leu Lys Leu Val Lys Glu Ile Ser His Ile Thr Gln Ala Pro Pro
        770                 775                 780

Lys Lys Ile Phe Ile Glu Met Ala Lys Gly Ala Glu Leu Glu Pro Ala
785                 790                 795                 800

Arg Thr Lys Thr Arg Leu Lys Ile Leu Gln Asp Leu Tyr Asn Asn Cys
                805                 810                 815

Lys Asn Asp Ala Asp Ala Phe Ser Ser Glu Ile Lys Asp Leu Ser Gly
                820                 825                 830

Lys Ile Glu Asn Glu Asp Asn Leu Arg Leu Arg Ser Lys Leu Tyr
            835                 840                 845        Tyr

Leu Tyr Tyr Thr Gln Leu Gly Lys Cys Met Tyr Cys Gly Lys Pro Ile
    850                 855                 860

Glu Ile Gly His Val Phe Asp Thr Ser Asn Tyr Asp Ile Asp His Ile
865                 870                 875                 880

Tyr Pro Gln Ser Lys Ile Lys Asp Asp Ser Ile Ser Asn Arg Val Leu
                885                 890                 895

Val Cys Ser Ser Cys Asn Lys Asn Lys Glu Asp Lys Tyr Pro Leu Lys
            900                 905                 910

Ser Glu Ile Gln Ser Lys Gln Arg Gly Phe Trp Asn Phe Leu Gln Arg
        915                 920                 925

Asn Asn Phe Ile Ser Leu Glu Lys Leu Asn Arg Leu Thr Arg Ala Thr
    930                 935                 940

Pro Ile Ser Asp Asp Glu Thr Ala Lys Phe Ile Ala Arg Gln Leu Val
945                 950                 955                 960

Glu Thr Arg Gln Ala Thr Lys Val Ala Ala Lys Val Leu Glu Lys Met
                965                 970                 975

Phe Pro Glu Thr Lys Ile Val Tyr Ser Lys Ala Glu Thr Val Ser Met
            980                 985                 990

Phe Arg Asn Lys Phe Asp Ile Val  Lys Cys Arg Glu Ile  Asn Asp Phe
        995                 1000                1005

His His Ala His Asp Ala Tyr  Leu Asn Ile Val Val  Gly Asn Val
    1010                1015                1020

Tyr Asn Thr Lys Phe Thr Asn  Asn Pro Trp Asn Phe  Ile Lys Glu
    1025                1030                1035

Lys Arg Asp Asn Pro Lys Ile  Ala Asp Thr Tyr Asn  Tyr Tyr Lys
    1040                1045                1050

Val Phe Asp Tyr Asp Val Lys  Arg Asn Asn Ile Thr  Ala Trp Glu
    1055                1060                1065

Lys Gly Lys Thr Ile Ile Thr  Val Lys Asp Met Leu  Lys Arg Asn
    1070                1075                1080

Thr Pro Ile Tyr Thr Arg Gln  Ala Ala Cys Lys Lys  Gly Glu Leu
    1085                1090                1095

Phe Asn Gln Thr Ile Met Lys  Lys Gly Leu Gly Gln  His Pro Leu
    1100                1105                1110

Lys Lys Glu Gly Pro Phe Ser  Asn Ile Ser Lys Tyr  Gly Gly Tyr
```

| | | | | | | | | | | | | |
|---|---|---|---|---|---|---|---|---|---|---|---|---|
| | | 1115 | | | | 1120 | | | | 1125 | | |
| Asn | Lys | Val | Ser | Ala | Ala | Tyr | Tyr | Thr | Leu | Ile | Glu | Tyr Glu Glu |
| | 1130 | | | | | 1135 | | | | 1140 | | |
| Lys | Gly | Asn | Lys | Ile | Arg | Ser | Leu | Glu | Thr | Ile | Pro | Leu Tyr Leu |
| | 1145 | | | | | 1150 | | | | 1155 | | |
| Val | Lys | Asp | Ile | Gln | Lys | Asp | Gln | Asp | Val | Leu | Lys | Ser Tyr Leu |
| | 1160 | | | | | 1165 | | | | 1170 | | |
| Thr | Asp | Leu | Leu | Gly | Lys | Lys | Glu | Phe | Lys | Ile | Leu | Val Pro Lys |
| | 1175 | | | | | 1180 | | | | 1185 | | |
| Ile | Lys | Ile | Asn | Ser | Leu | Leu | Lys | Ile | Asn | Gly | Phe | Pro Cys His |
| | 1190 | | | | | 1195 | | | | 1200 | | |
| Ile | Thr | Gly | Lys | Thr | Asn | Asp | Ser | Phe | Leu | Leu | Arg | Pro Ala Val |
| | 1205 | | | | | 1210 | | | | 1215 | | |
| Gln | Phe | Cys | Cys | Ser | Asn | Asn | Glu | Val | Leu | Tyr | Phe | Lys Lys Ile |
| | 1220 | | | | | 1225 | | | | 1230 | | |
| Ile | Arg | Phe | Ser | Glu | Ile | Arg | Ser | Gln | Arg | Glu | Lys | Ile Gly Lys |
| | 1235 | | | | | 1240 | | | | 1245 | | |
| Thr | Ile | Ser | Pro | Tyr | Glu | Asp | Leu | Ser | Phe | Arg | Ser | Tyr Ile Lys |
| | 1250 | | | | | 1255 | | | | 1260 | | |
| Glu | Asn | Leu | Trp | Lys | Lys | Thr | Lys | Asn | Asp | Glu | Ile | Gly Glu Lys |
| | 1265 | | | | | 1270 | | | | 1275 | | |
| Glu | Phe | Tyr | Asp | Leu | Leu | Gln | Lys | Lys | Asn | Leu | Glu | Ile Tyr Asp |
| | 1280 | | | | | 1285 | | | | 1290 | | |
| Met | Leu | Leu | Thr | Lys | His | Lys | Asp | Thr | Ile | Tyr | Lys | Lys Arg Pro |
| | 1295 | | | | | 1300 | | | | 1305 | | |
| Asn | Ser | Ala | Thr | Ile | Asp | Ile | Leu | Val | Lys | Gly | Lys | Glu Lys Phe |
| | 1310 | | | | | 1315 | | | | 1320 | | |
| Lys | Ser | Leu | Ile | Ile | Glu | Asn | Gln | Phe | Glu | Val | Ile | Leu Glu Ile |
| | 1325 | | | | | 1330 | | | | 1335 | | |
| Leu | Lys | Leu | Phe | Ser | Ala | Thr | Arg | Asn | Val | Ser | Asp | Leu Gln His |
| | 1340 | | | | | 1345 | | | | 1350 | | |
| Ile | Gly | Gly | Ser | Lys | Tyr | Ser | Gly | Val | Ala | Lys | Ile | Gly Asn Lys |
| | 1355 | | | | | 1360 | | | | 1365 | | |
| Ile | Ser | Ser | Leu | Asp | Asn | Cys | Ile | Leu | Ile | Tyr | Gln | Ser Ile Thr |
| | 1370 | | | | | 1375 | | | | 1380 | | |
| Gly | Ile | Phe | Glu | Lys | Arg | Ile | Asp | Leu | Leu | Lys | Val | Ala Ala Ala |
| | 1385 | | | | | 1390 | | | | 1395 | | |
| Asp | Pro | Lys | Lys | Lys | Arg | Lys | Val | Asp | Pro | Lys | Lys | Lys Arg Lys |
| | 1400 | | | | | 1405 | | | | 1410 | | |
| Val | Asp | Pro | Lys | Lys | Lys | Arg | Lys | Val | Asp | Thr | Ala | Ala |
| | 1415 | | | | | 1420 | | | | 1425 | | |

<210> SEQ ID NO 25
<211> LENGTH: 102
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 25
nnnnnnnnnn nnnnnnnnnn guuuuagagc uagaaauagc aaguuaaaau aaggcuaguc    60
cguuaucaac uugaaaaagu ggcaccgagu cggugcuuuu uu    102

```
<210> SEQ ID NO 26
<211> LENGTH: 150
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 26
nnnnnnnnnn nnnnnnnnnn guuuuagagc uaugcuguuu ugaauggucc caaaacgaaa      60
uuguuggaac cauucaaaac agcauagcaa guuaaaauaa ggcuaguccg uuaucaacuu     120
gaaaaagugg caccgagucg gugcuuuuuu                                    150

<210> SEQ ID NO 27
<211> LENGTH: 105
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 27
nnnnnnnnnn nnnnnnnnnn guuuuuguac ucucagaaau gcagaagcua caaagauaag      60
gcuucaugcc gaaaucaaca cccugucauu uuauggcagg guguu                    105

<210> SEQ ID NO 28
<211> LENGTH: 147
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 28
nnnnnnnnnn nnnnnnnnnn guuuuuguac ucucaagauu uaaguaacug uacaacgaaa      60
cuuacacagu uacuuaaauc uugcagaagc uacaaagaua aggcuucaug ccgaaaucaa     120
cacccuguca uuuuauggca gggaguu                                       147

<210> SEQ ID NO 29
<211> LENGTH: 110
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 29
nnnnnnnnnn nnnnnnnnnn guuuuuguac ucucagaaau gcagaagcua caaagauaag      60
gcuucaugcc gaaaucaaca cccugucauu uuauggcagg guguuuuuuu               110

<210> SEQ ID NO 30
```

```
<211> LENGTH: 110
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 30
nnnnnnnnnn nnnnnnnnnn guuuuaguac ucucagaaau gcagaagcuu caaagauaag      60
gcuucaugcc gaaaucaaca cccugucauu uuauggcagg guguuuuuu                  110

<210> SEQ ID NO 31
<211> LENGTH: 110
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 31
nnnnnnnnnn nnnnnnnnnn guuuguguac ucucagaaau gcagaagcua caaagauaag      60
gcuucaugcc gaaaucaaca cccugucauu uuauggcagg guguuuuuu                  110

<210> SEQ ID NO 32
<211> LENGTH: 110
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 32
nnnnnnnnnn nnnnnnnnnn guuuauguac ucucagaaau gcagaagcua caaagauaag      60
gcuucaugcc gaaaucaaca cccugucauu uuauggcagg guguuuuuu                  110

<210> SEQ ID NO 33
<211> LENGTH: 105
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 33
nnnnnnnnnn nnnnnnnnnn guuuuguac ucugaaaaga agcuacaaag auaaggcuuc        60
augccgaaau caacacccug ucauuuuaug gcaggguguu uuuuu                      105

<210> SEQ ID NO 34
<211> LENGTH: 105
<212> TYPE: RNA
<213> ORGANISM: Artificial Sequence
<220> FEATURE:
<223> OTHER INFORMATION: gRNA
<220> FEATURE:
<221> NAME/KEY: misc_feature
```

-continued

<222> LOCATION: (1)..(20)
<223> OTHER INFORMATION: wherein N is any of the nucleotide U, C, A or G

<400> SEQUENCE: 34
nnnnnnnnnn nnnnnnnnnn guuuaguac ucugaaaaga agcuucaaag auaaggcuuc    60
augccgaaau caacacccug ucauuuaug gcagggguguu uuuuu                    105

<210> SEQ ID NO 35
<211> LENGTH: 105
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 35
nnnnnnnnnn nnnnnnnnnn guuuguguac ucugaaaaga agcuacaaag auaaggcuuc    60
augccgaaau caacacccug ucauuuaug gcaggguguu uuuuu                     105

<210> SEQ ID NO 36
<211> LENGTH: 105
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 36
nnnnnnnnnn nnnnnnnnnn guuuauguac ucugaaaaga agcuacaaag auaaggcuuc    60
augccgaaau caacacccug ucauuuaug gcaggguguu uuuuu                     105

<210> SEQ ID NO 37
<211> LENGTH: 152
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 37
nnnnnnnnnn nnnnnnnnnn guuuuguac ucucaagauu uaaguaacug uacaacgaaa    60
cuuacacagu uacuuaaauc uugcagaagc uacaagauua aggcuucaug ccgaaaucaa   120
cacccuguca uuuuauggca ggguguuuuu uu                                 152

<210> SEQ ID NO 38
<211> LENGTH: 152
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 38

-continued nnnnnnnnnn nnnnnnnnnn guuuaguac ucucaagauu uaaguaacug uacaacgaaa    60
cuuacacagu uacuuaaauc uugcagaagc uucaaagaua aggcuucaug ccgaaaucaa   120
cacccuguca uuuuauggca ggguguuuuu uu                                 152

<210> SEQ ID NO 39
<211> LENGTH: 152
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 39
nnnnnnnnnn nnnnnnnnnn guuuguguac ucucaagauu uaaguaacug uacaacgaaa    60
cuuacacagu uacuuaaauc uugcagaagc uacaaagaua aggcuucaug ccgaaaucaa   120
cacccuguca uuuuauggca ggguguuuuu uu                                 152

<210> SEQ ID NO 40
<211> LENGTH: 152
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 40
nnnnnnnnnn nnnnnnnnnn guuuauguac ucucaagauu uaaguaacug uacaacgaaa    60
cuuacacagu uacuuaaauc uugcagaagc uacaaagaua aggcuucaug ccgaaaucaa   120
cacccuguca uuuuauggca ggguguuuuu uu                                 152

<210> SEQ ID NO 41
<211> LENGTH: 121
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 41
nnnnnnnnnn nnnnnnnnnn guuguagcuc ccuuucucga aagagaaccg uugcuacaau    60
aaggccgucu gaaaagaugu gccgcaacgc ucugccccuu aaagcuucug cuuuaagggg   120
c                                                                   121

<210> SEQ ID NO 42
<211> LENGTH: 157
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 42
nnnnnnnnnn nnnnnnnnnn guuguagcuc ccuuucucau uucgcagugc uacaaugaaa    60
auugucgcac ugcgaaauga gaaccguugc uacaauaagg ccgucugaaa agaugugccg    120
caacgcucug ccccuuaaag cuucugcuuu aaggggc    157

<210> SEQ ID NO 43
<211> LENGTH: 128
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 43
nnnnnnnnnn nnnnnnnnnn guuguagcuc ccuuucucga aagagaaccg uugcuacaau    60
aaggccgucu gaaaagaugu gccgcaacgc ucugccccuu aaagcuucug cuuuaacggg    120
cuuuuuuu    128

<210> SEQ ID NO 44
<211> LENGTH: 124
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 44
nnnnnnnnnn nnnnnnnnnn guuguagcuc ccuuucgaaa gaaccguugc uacaauaagg    60
ccgucugaaa agaugugccg caacgcucug ccccuuaaag cuucugcuuu aacgggcuuu    120
uuuu    124

<210> SEQ ID NO 45
<211> LENGTH: 116
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 45
nnnnnnnnnn nnnnnnnnnn guuguagcuc ccgaaacguu gcuacaauaa ggccgucuga    60
aaagaugugc cgcaacgcuc ugccccuuaa agcuucugcu uuaacgggcu uuuuu    116

<210> SEQ ID NO 46
<211> LENGTH: 164
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 46

```
nnnnnnnnnn nnnnnnnnnn guuguagcuc ccuuucucau uucgcagugc uacaaugaaa    60
auugucgcac ugcgaaauga gaaccguugc uacaauaagg ccgucugaaa agaugugccg   120
caacgcucug ccccuuaaag cuucugcuuu aagggcuuu uuuu                     164
```

<210> SEQ ID NO 47
<211> LENGTH: 141
<212> TYPE: RNA
<213> ORGANISM: Artificial Sequence
<220> FEATURE:
<223> OTHER INFORMATION: gRNA
<220> FEATURE:
<221> NAME/KEY: misc_feature
<222> LOCATION: (1)..(20)
<223> OTHER INFORMATION: wherein N is any of the nucleotide U, C, A or G

<400> SEQUENCE: 47

```
nnnnnnnnnn nnnnnnnnnn guuguagcuc ccuuucucau uucggaaacg aaaugagaac    60
cguugcuaca auaaggccgu cugaaaagau gugccgcaac gcucugcccc uuaaagcuuc   120
ugcuuuaagg ggcaucguuu a                                             141
```

<210> SEQ ID NO 48
<211> LENGTH: 4
<212> TYPE: RNA
<213> ORGANISM: Artificial Sequence
<220> FEATURE:
<223> OTHER INFORMATION: Linker

<400> SEQUENCE: 48

```
gaaa                                                                  4
```

<210> SEQ ID NO 49
<211> LENGTH: 16
<212> TYPE: PRT
<213> ORGANISM: Artificial Sequence
<220> FEATURE:
<223> OTHER INFORMATION: Signal

<400> SEQUENCE: 49

Lys Arg Pro Ala Ala Thr Lys Lys Ala Gly Gln Ala Lys Lys Lys Lys
1               5                   10                  15

<210> SEQ ID NO 50
<211> LENGTH: 9
<212> TYPE: PRT
<213> ORGANISM: Artificial Sequence
<220> FEATURE:
<223> OTHER INFORMATION: Signal

<400> SEQUENCE: 50

Pro Ala Ala Lys Arg Val Lys Leu Asp
1               5

<210> SEQ ID NO 51
<211> LENGTH: 9
<212> TYPE: PRT
<213> ORGANISM: Artificial Sequence
<220> FEATURE:
<223> OTHER INFORMATION: Signal

<400> SEQUENCE: 51

Pro Pro Arg Lys Lys Arg Thr Val Val
1               5

<210> SEQ ID NO 52

```
<211> LENGTH: 11
<212> TYPE: PRT
<213> ORGANISM: Artificial Sequence
<220> FEATURE:
<223> OTHER INFORMATION: Signal

<400> SEQUENCE: 52

Pro Arg Pro Pro Lys Met Ala Arg Tyr Asp Asn
1               5                   10

<210> SEQ ID NO 53
<211> LENGTH: 20
<212> TYPE: DNA
<213> ORGANISM: Artificial Sequence
<220> FEATURE:
<223> OTHER INFORMATION: gRNA

<400> SEQUENCE: 53
ccaaggcaac gggactgtgc                                                    20

<210> SEQ ID NO 54
<211> LENGTH: 20
<212> TYPE: DNA
<213> ORGANISM: Artificial Sequence
<220> FEATURE:
<223> OTHER INFORMATION: gRNA

<400> SEQUENCE: 54
tcaggtctga tgcagatcgg                                                    20

<210> SEQ ID NO 55
<211> LENGTH: 20
<212> TYPE: DNA
<213> ORGANISM: Artificial Sequence
<220> FEATURE:
<223> OTHER INFORMATION: gRNA

<400> SEQUENCE: 55
cagccacatc taccgccatg                                                    20

<210> SEQ ID NO 56
<211> LENGTH: 20
<212> TYPE: DNA
<213> ORGANISM: Artificial Sequence
<220> FEATURE:
<223> OTHER INFORMATION: gRNA

<400> SEQUENCE: 56
gtacctcccg cttcaatgtc                                                    20

<210> SEQ ID NO 57
<211> LENGTH: 20
<212> TYPE: DNA
<213> ORGANISM: Artificial Sequence
<220> FEATURE:
<223> OTHER INFORMATION: Oligo

<400> SEQUENCE: 57
ccaaggcaac gggactgtgc                                                    20

<210> SEQ ID NO 58
<211> LENGTH: 20
<212> TYPE: DNA
<213> ORGANISM: Artificial Sequence
<220> FEATURE:
<223> OTHER INFORMATION: Oligo
```

<400> SEQUENCE: 58
cagccacatc taccgccatg                                                    20

<210> SEQ ID NO 59
<211> LENGTH: 20
<212> TYPE: DNA
<213> ORGANISM: Artificial Sequence
<220> FEATURE:
<223> OTHER INFORMATION: Oligo

<400> SEQUENCE: 59
ccaaggcaac gggactgtgc                                                    20

<210> SEQ ID NO 60
<211> LENGTH: 20
<212> TYPE: DNA
<213> ORGANISM: Artificial Sequence
<220> FEATURE:
<223> OTHER INFORMATION: Oligo

<400> SEQUENCE: 60
gtacctcccg cttcaatgtc                                                    20

<210> SEQ ID NO 61
<211> LENGTH: 20
<212> TYPE: DNA
<213> ORGANISM: Artificial Sequence
<220> FEATURE:
<223> OTHER INFORMATION: Oligo

<400> SEQUENCE: 61
tcaggtctga tgcagatcgg                                                    20

<210> SEQ ID NO 62
<211> LENGTH: 20
<212> TYPE: DNA
<213> ORGANISM: Artificial Sequence
<220> FEATURE:
<223> OTHER INFORMATION: Oligo

<400> SEQUENCE: 62
cagccacatc taccgccatg                                                    20

<210> SEQ ID NO 63
<211> LENGTH: 20
<212> TYPE: DNA
<213> ORGANISM: Artificial Sequence
<220> FEATURE:
<223> OTHER INFORMATION: Oligo

<400> SEQUENCE: 63
tcaggtctga tgcagatcgg                                                    20

<210> SEQ ID NO 64
<211> LENGTH: 20
<212> TYPE: DNA
<213> ORGANISM: Artificial Sequence
<220> FEATURE:
<223> OTHER INFORMATION: Oligo

<400> SEQUENCE: 64
gtacctcccg cttcaatgtc                                                    20

<210> SEQ ID NO 65
<211> LENGTH: 42

<212> TYPE: DNA
<213> ORGANISM: Artificial Sequence
<220> FEATURE:
<223> OTHER INFORMATION: Primer

<400> SEQUENCE: 65
tgtaaaacga cggccaggct gcttaaaatg cagattccaa ag       42

<210> SEQ ID NO 66
<211> LENGTH: 25
<212> TYPE: DNA
<213> ORGANISM: Artificial Sequence
<220> FEATURE:
<223> OTHER INFORMATION: Primer

<400> SEQUENCE: 66
ggagagatag gggataaaag tggtg       25

<210> SEQ ID NO 67
<211> LENGTH: 42
<212> TYPE: DNA
<213> ORGANISM: Artificial Sequence
<220> FEATURE:
<223> OTHER INFORMATION: Primer

<400> SEQUENCE: 67
tgtaaaacga cggccagcag actcttgaac ccaaactctt tc       42

<210> SEQ ID NO 68
<211> LENGTH: 25
<212> TYPE: DNA
<213> ORGANISM: Artificial Sequence
<220> FEATURE:
<223> OTHER INFORMATION: Primer

<400> SEQUENCE: 68
ggactgactt agtgtctttg ctttt       25

<210> SEQ ID NO 69
<211> LENGTH: 42
<212> TYPE: DNA
<213> ORGANISM: Artificial Sequence
<220> FEATURE:
<223> OTHER INFORMATION: Primer

<400> SEQUENCE: 69
tgtaaaacga cggccagaga aggattaagc tccacttacc aa       42

<210> SEQ ID NO 70
<211> LENGTH: 25
<212> TYPE: DNA
<213> ORGANISM: Artificial Sequence
<220> FEATURE:
<223> OTHER INFORMATION: Primer

<400> SEQUENCE: 70
tgaaaggtat gggagaatgt aacaa       25

<210> SEQ ID NO 71
<211> LENGTH: 42
<212> TYPE: DNA
<213> ORGANISM: Artificial Sequence
<220> FEATURE:
<223> OTHER INFORMATION: Primer

<400> SEQUENCE: 71

```
tgtaaaacga cggccagtgc agatgaaagt tgtttgccta at              42
```

<210> SEQ ID NO 72
<211> LENGTH: 25
<212> TYPE: DNA
<213> ORGANISM: Artificial Sequence
<220> FEATURE:
<223> OTHER INFORMATION: Primer

<400> SEQUENCE: 72

```
ggagggatag cattgggaga tatac                                 25
```

<210> SEQ ID NO 73
<211> LENGTH: 43
<212> TYPE: DNA
<213> ORGANISM: Artificial Sequence
<220> FEATURE:
<223> OTHER INFORMATION: Primer

<400> SEQUENCE: 73

```
tgtaaaacga cggccagact tagtcccttt aaattgtgct tca             43
```

<210> SEQ ID NO 74
<211> LENGTH: 25
<212> TYPE: DNA
<213> ORGANISM: Artificial Sequence
<220> FEATURE:
<223> OTHER INFORMATION: Primer

<400> SEQUENCE: 74

```
atacattgaa agagccatgt ctggg                                 25
```

<210> SEQ ID NO 75
<211> LENGTH: 8
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(4)
<223> OTHER INFORMATION: wherein N is any of the nucleotide T, C, A or G
<220> FEATURE:
<221> NAME/KEY: misc_feature
<222> LOCATION: (8)..(8)
<223> OTHER INFORMATION: wherein N is any of the nucleotide T, C, A or G

<400> SEQUENCE: 75

```
nnnngttn                                                    8
```

<210> SEQ ID NO 76
<211> LENGTH: 8
<212> TYPE: DNA
<213> ORGANISM: Artificial Sequence
<220> FEATURE:
<223> OTHER INFORMATION: Motif
<220> FEATURE:
<221> NAME/KEY: misc_feature
<222> LOCATION: (1)..(4)
<223> OTHER INFORMATION: wherein N is any of the nucleotide T, C, A or G
<220> FEATURE:
<221> NAME/KEY: misc_feature
<222> LOCATION: (6)..(7)
<223> OTHER INFORMATION: wherein N is any of the nucleotide T, C, A or G

<400> SEQUENCE: 76

```
nnnngnnt                                                    8
```

-continued

```
<210> SEQ ID NO 77
<211> LENGTH: 25
<212> TYPE: DNA
<213> ORGANISM: Artificial Sequence
<220> FEATURE:
<223> OTHER INFORMATION: Forward primer

<400> SEQUENCE: 77
aggtgaacat catccagaag gggca                                           25

<210> SEQ ID NO 78
<211> LENGTH: 25
<212> TYPE: DNA
<213> ORGANISM: Artificial Sequence
<220> FEATURE:
<223> OTHER INFORMATION: Reverse primer

<400> SEQUENCE: 78
aagcaggcac aaaaccaaag cctct                                           25

<210> SEQ ID NO 79
<211> LENGTH: 25
<212> TYPE: DNA
<213> ORGANISM: Artificial Sequence
<220> FEATURE:
<223> OTHER INFORMATION: Reverse primer

<400> SEQUENCE: 79
aaaataaggg gaccggacag gctgg                                           25

<210> SEQ ID NO 80
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: N is any of A, C, T or G

<400> SEQUENCE: 80
aacacnacca g                                                          11

<210> SEQ ID NO 81
<211> LENGTH: 11
<212> TYPE: DNA
<213> ORGANISM: Artificial Sequence
<220> FEATURE:
<223> OTHER INFORMATION: Primer

<400> SEQUENCE: 81
aacactacca g                                                          11

<210> SEQ ID NO 82
<211> LENGTH: 11
<212> TYPE: DNA
<213> ORGANISM: Artificial Sequence
<220> FEATURE:
<223> OTHER INFORMATION: Primer

<400> SEQUENCE: 82
aacactacca g                                                          11

<210> SEQ ID NO 83
<211> LENGTH: 11
<212> TYPE: DNA
```

```
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: N is any of A, C, T or G

<400> SEQUENCE: 83
actccntctc t                                                          11

<210> SEQ ID NO 84
<211> LENGTH: 11
<212> TYPE: DNA
<213> ORGANISM: Artificial Sequence
<220> FEATURE:
<223> OTHER INFORMATION: Primer

<400> SEQUENCE: 84
actccgtctc t                                                          11

<210> SEQ ID NO 85
<211> LENGTH: 11
<212> TYPE: DNA
<213> ORGANISM: Artificial Sequence
<220> FEATURE:
<223> OTHER INFORMATION: Primer

<400> SEQUENCE: 85
actccgtctc t                                                          11

<210> SEQ ID NO 86
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: N is any of A, C, T or G

<400> SEQUENCE: 86
aatttnagct a                                                          11

<210> SEQ ID NO 87
<211> LENGTH: 11
<212> TYPE: DNA
<213> ORGANISM: Artificial Sequence
<220> FEATURE:
<223> OTHER INFORMATION: Primer

<400> SEQUENCE: 87
aatttgagct a                                                          11

<210> SEQ ID NO 88
<211> LENGTH: 11
<212> TYPE: DNA
<213> ORGANISM: Artificial Sequence
<220> FEATURE:
<223> OTHER INFORMATION: Primer

<400> SEQUENCE: 88
aatttgagct a                                                          11

<210> SEQ ID NO 89
<211> LENGTH: 11
```

```
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: N is any of A, C, T or G

<400> SEQUENCE: 89
tcaacnctgc a                                                            11

<210> SEQ ID NO 90
<211> LENGTH: 11
<212> TYPE: DNA
<213> ORGANISM: Artificial Sequence
<220> FEATURE:
<223> OTHER INFORMATION: Primer

<400> SEQUENCE: 90
tcaacactgc a                                                            11

<210> SEQ ID NO 91
<211> LENGTH: 11
<212> TYPE: DNA
<213> ORGANISM: Artificial Sequence
<220> FEATURE:
<223> OTHER INFORMATION: Primer

<400> SEQUENCE: 91
tcaacactgc a                                                            11

<210> SEQ ID NO 92
<211> LENGTH: 11
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: N is any of A, C, T or G

<400> SEQUENCE: 92
tgtcangatg g                                                            11

<210> SEQ ID NO 93
<211> LENGTH: 11
<212> TYPE: DNA
<213> ORGANISM: Artificial Sequence
<220> FEATURE:
<223> OTHER INFORMATION: Primer

<400> SEQUENCE: 93
tgtcacgatg g                                                            11

<210> SEQ ID NO 94
<211> LENGTH: 11
<212> TYPE: DNA
<213> ORGANISM: Artificial Sequence
<220> FEATURE:
<223> OTHER INFORMATION: Primer

<400> SEQUENCE: 94
tgtcacgatg g                                                            11

<210> SEQ ID NO 95
```

```
<211> LENGTH: 428
<212> TYPE: DNA
<213> ORGANISM: Artificial Sequence
<220> FEATURE:
<223> OTHER INFORMATION: Clone A11

<400> SEQUENCE: 95
ccagaagggg catgtcctat cattgtaata aaaaaggaca ctgccagttt ctgaactata      60
gtgacaccac caaggcaacg gtagatgtgg ctgagagccc tgcccttgag cctttggct     120
tgaggcttca tgccagcatc cacggaggca cagcttcagg gtccctggtg gcccagccac    180
tgggcaagag aggatgctct tttccatccc tgggtctggc tagaggccct ggagggagtc    240
agggtccttg ccaaagagca gcagagcctg ccgtgaagtg aaggcttctg aaagaaatga    300
gtctgaatcc tggctccacc tgtccaaact gtgtgacctt aagcaaatta caagggagct    360
tgctgtgcct cagcatcctt gtctctataa tgggaaggtg atagcctcat aggggcttg    420
tgaggttt                                                             428

<210> SEQ ID NO 96
<211> LENGTH: 434
<212> TYPE: DNA
<213> ORGANISM: Artificial Sequence
<220> FEATURE:
<223> OTHER INFORMATION: Clone E9

<400> SEQUENCE: 96
ccagaagggg catgtcctat cattgtaata aaaaaggaca ctgccagttt ctgaactata      60
gtgacaccac caaggcaacg ggaccggtag atgtggctga gagccctgcc cttgagcctt    120
ttggcttgag gcttcatgcc agcatccacg gaggcacagc ttcagggtcc ctggtggccc    180
agccactggg caagagagga tgctcttttc catccctggg tctggctaga ggccctggag    240
ggagtcaggg tccttgccaa agagcagcag agcctgccgt gaagtgaagg cttctgaaag    300
aaatgagtct gaatcctggc tccacctgtc caaactgtgt gacctaagc aaattacaag    360
ggagcttgct gtgcctcagc atccttgtct ctataatggg aaggtgatag cctcataggg    420
ggcttgtgag gttt                                                      434

<210> SEQ ID NO 97
<211> LENGTH: 20
<212> TYPE: DNA
<213> ORGANISM: Artificial Sequence
<220> FEATURE:
<223> OTHER INFORMATION: gRNA

<400> SEQUENCE: 97
ccaaggcaac gggactgtgc                                                 20

<210> SEQ ID NO 98
<211> LENGTH: 20
<212> TYPE: DNA
<213> ORGANISM: Artificial Sequence
<220> FEATURE:
<223> OTHER INFORMATION: gRNA

<400> SEQUENCE: 98
tcaggtctga tgcagatcgg                                                 20

<210> SEQ ID NO 99
<211> LENGTH: 20
<212> TYPE: DNA
<213> ORGANISM: Artificial Sequence
```

```
<220> FEATURE:
<223> OTHER INFORMATION: gRNA

<400> SEQUENCE: 99
cagccacatc taccgccatg                                                     20

<210> SEQ ID NO 100
<211> LENGTH: 20
<212> TYPE: DNA
<213> ORGANISM: Artificial Sequence
<220> FEATURE:
<223> OTHER INFORMATION: gRNA

<400> SEQUENCE: 100
gtacctcccg cttcaatgtc                                                     20

<210> SEQ ID NO 101
<211> LENGTH: 42
<212> TYPE: DNA
<213> ORGANISM: Artificial Sequence
<220> FEATURE:
<223> OTHER INFORMATION: Primer

<400> SEQUENCE: 101
tgtaaaacga cggccaggct gcttaaaatg cagattccaa ag                            42

<210> SEQ ID NO 102
<211> LENGTH: 25
<212> TYPE: DNA
<213> ORGANISM: Artificial Sequence
<220> FEATURE:
<223> OTHER INFORMATION: Primer

<400> SEQUENCE: 102
ggagagatag gggataaaag tggtg                                               25

<210> SEQ ID NO 103
<211> LENGTH: 42
<212> TYPE: DNA
<213> ORGANISM: Artificial Sequence
<220> FEATURE:
<223> OTHER INFORMATION: Primer

<400> SEQUENCE: 103
tgtaaaacga cggccagaga aggattaagc tccacttacc aa                            42

<210> SEQ ID NO 104
<211> LENGTH: 25
<212> TYPE: DNA
<213> ORGANISM: Artificial Sequence
<220> FEATURE:
<223> OTHER INFORMATION: Primer

<400> SEQUENCE: 104
tgaaaggtat gggagaatgt aacaa                                               25

<210> SEQ ID NO 105
<211> LENGTH: 42
<212> TYPE: DNA
<213> ORGANISM: Artificial Sequence
<220> FEATURE:
<223> OTHER INFORMATION: Primer

<400> SEQUENCE: 105
tgtaaaacga cggccagtgc agatgaaagt tgtttgccta at                            42
```

```
<210> SEQ ID NO 106
<211> LENGTH: 25
<212> TYPE: DNA
<213> ORGANISM: Artificial Sequence
<220> FEATURE:
<223> OTHER INFORMATION: Primer

<400> SEQUENCE: 106
ggagggatag cattgggaga tatac                                       25

<210> SEQ ID NO 107
<211> LENGTH: 43
<212> TYPE: DNA
<213> ORGANISM: Artificial Sequence
<220> FEATURE:
<223> OTHER INFORMATION: Primer

<400> SEQUENCE: 107
tgtaaaacga cggccagact tagtcccttaa aaattgtgct tca                  43

<210> SEQ ID NO 108
<211> LENGTH: 25
<212> TYPE: DNA
<213> ORGANISM: Artificial Sequence
<220> FEATURE:
<223> OTHER INFORMATION: Primer

<400> SEQUENCE: 108
atacattgaa agagccatgt ctggg                                       25

<210> SEQ ID NO 109
<211> LENGTH: 42
<212> TYPE: DNA
<213> ORGANISM: Artificial Sequence
<220> FEATURE:
<223> OTHER INFORMATION: Primer

<400> SEQUENCE: 109
tgtaaaacga cggccagcag actcttgaac ccaaactctt tc                    42

<210> SEQ ID NO 110
<211> LENGTH: 25
<212> TYPE: DNA
<213> ORGANISM: Artificial Sequence
<220> FEATURE:
<223> OTHER INFORMATION: Primer

<400> SEQUENCE: 110
ggactgactt agtgtctttg ctttt                                       25

<210> SEQ ID NO 111
<211> LENGTH: 17
<212> TYPE: DNA
<213> ORGANISM: Artificial Sequence
<220> FEATURE:
<223> OTHER INFORMATION: Primer

<400> SEQUENCE: 111
tgtaaaacga cggccag                                                17
```

SOMATIC HAPLOID HUMAN CELL LINE

CROSS-REFERENCE TO RELATED APPLICATIONS

This application is a U.S. national stage filing under 35 U.S.C. § 371 of International Application No. PCT/EP2014/076029, filed on Nov. 28, 2014, incorporated by reference herein in its entirety, which claims the benefit of priority to European Patent Application No. 14191914.2, filed on Nov. 5,2014, European Patent Application No. 14181367.5, filed on Aug. 19, 2014, International Application No. PCT/EP2014/066732, filed on Aug. 4, 2014, European Patent Application No. 13194940.6, filed no Nov. 28, 2013, and European Patent Application No. 13194939.8, filed on Nov. 28, 2013.

SEQUENCE LISTING

This application contains a sequence listing, submitted electronically in ASCII format under the filename 00012-0016-00000_Sequence_Listing.txt, which is incorporated by reference herein in its entirety. The ASCII copy of the sequence listing was created on May 27, 2016, and is 150,637 bytes in size.

The invention refers to mutant somatic human cell lines which are fully haploid.

BACKGROUND

To protect genomic integrity, humans are diploid, ie. they possess two copies of each chromosome (with the exception of the X- and the Y-chromosome that only exist in one copy), one from their father and one from their mother. If one gene on one chromosome is damaged, in many instances, the remaining second copy is sufficient to maintain gene function, thereby alleviating the otherwise deleterious effect. This fail-save mechanism that is essential for the survival of humans as a species turns out to be a nightmare for human geneticists: Whenever one copy of a gene is inactivated, the second copy usually buffers the effect, thereby masking the phenotype of that particular gene.

For the longest time, the only human cells that were known to be haploid were the gametes, i.e. the sperm cell and the oocyte. However, as these cells could not be propagated, they could not be used for genetic experiments (apart from ethical restrictions). More than 15 years ago, a group of scientists at Tufts University stumbled upon a cell line that had been isolated from a patient with chronic myelogenous leukemia (CML). That cell line, referred to as KBM-7 [1], was haploid for most chromosomes with the exception of chromosome 8 and a portion of chromosome 15, which were found to be disomic. Its near-haploid state could be maintained for several months in culture. Yet, eventually, KBM-7 cells convert to diploid [1], suggesting that the near-haploid karyotype rather represents a "metastable" state.

While the authors [1] noted that this cell line could be used "to facilitate the application of somatic cell genetics to the study of mammalian cell biology", it took more than 10 years until Thijn Brummelkamp and his coworkers at the Whitehead Institute for Biomedical Research successfully applied KBM-7 cells for genetic experiments in human cells [2]. In this landmark paper, the authors used retroviral vectors to insert a conventional gene trap into the host genome and thereby disrupted gene expression at the site of integration. Most importantly, as retroviruses can be grown at very high titers, the method allowed the simultaneous disruptions of most non-essential human genes at very high coverage in a pool of mutant cells, thereby enabling unbiased positive selection screens [3]—similar to the screens done in yeast more than 15 years ago.

In addition to the unbiased genetics screens, the technology developed by Brummelkamp enabled the generation of a unique library of human cell lines in which every cell line bears one gene trap insertion at one defined position. Importantly, such libraries enable reverse genetics, ie. the study of individual mutants with regard to a specific phenotype under consideration. Such a library has recently been established. It contains almost 10,000 cell lines, covering more than 3,500 human genes [4]. In addition, this publication also contains a detailed genomic characterization of the parental KBM-7 cells by next generation sequencing and small nucleotide polymorphism (SNP) arrays. Based on these data, the disomic portion on chromosome 15 could be mapped to the region around chr15: 61,105,000-89,890,000.

While the genetic screens described above were very powerful, they were clearly limited by the availability of near-haploid human cell lines—at the time, KBM-7 was the only available cell line. Brummelkamp and coworkers therefore decided to reprogram KBM-7 cells to obtain induced pluripotent stem cells (iPSCs). While this turned out to be feasible, KBM-7-derived iPSCs lost their near-haploid karyotype during the de-differentiation procedure [5]. However, one by-product of this reaction was an adherent cell line called HAP1 that remained near-haploid and that showed a fibroblast-like morphology [6]. Importantly, HAP1 cells are not pluripotent, but they differ considerably from their KBM-7 parent cells in terms of growth, morphology and gene expression. Of note, HAP1 cells are also monosomic for chromosome 8 and are thus "more haploid" than their KBM-7 parents. However, HAP1 cells do retain the disomic fragment from chromosome 15 and can thus not be considered fully haploid. In addition, HAP1 cells are less stable than KBM-7 with regard to their near-haploid karyotype, i.e. they convert to the diploid state more readily than KBM-7 cells.

Bacteria have a need to maintain their genomic integrity and defend against invading viruses and plasmids. Recently, genomic loci with clustered, regularly interspaced, short palindromic repeats (CRISPRs) were found in bacteria and were shown to mediate adaptive immunity to invading phages [7]: Bacteria can capture short nucleic acid sequences from the phage and integrate them in the CRISPR loci. Small RNAs, produced by transcription of the CRISPR loci, can guide a set of bacterial endonucleases to cleave the genomes of invading pathogens.

The minimal requirements for one bacterial endonuclease, CAS9 from *Streptococcus pyogenes*, were characterized by purifying the enzyme and reconstituting the cleavage reaction in vitro [8]. Surprisingly, CAS9 itself is sufficient for endonuclease cleavage and no further polypeptides are required for the cleavage reaction. In addition, CAS9 requires two RNA cofactors: a constant tracrRNA and a variable crRNA. Importantly, the crRNA can be used to reprogram the cleavage specificity of CAS9, thereby enabling the targeting of CAS9 to genomic loci of interest. Cleavage specificity is limited by the protospacer adjacent motif (PAM) that is specific to CAS9 and lies adjacent to the cleavage site. In an attempt to simplify the system, crRNA and tracrRNA were fused to give rise to one chimeric RNA molecule referred to as the guide RNA.

US 2010/0076057 A1 discloses the target DNA interference with crRNA and CRISPR-associated (cas) proteins, in particular for horizontal gene transfer based on the use of CRISPR sequences.

The RNA-directed DNA cleavage by the CAS9-crRNA complex is described by WO 2013/141680 A1 and WO 2013/142578 A1.

It is the object of the present invention to engineer near-haploid cells to reduce diploidy of the cells. It is the further object to provide a cell line of haploid karyotype that is karyotypically stable.

SUMMARY OF THE INVENTION

The object is solved by the subject matter as claimed.

According to the invention, there is provided a somatic fully haploid, karyotypically stable human cell line. Specifically, the cell line is obtainable by targeted deletion of one or more disomic (herein also referred to as diploidic) chromosomal regions of a somatic near-haploid human parental cell.

Specifically, the cell line is an adherent cell line.

According to a specific embodiment, the cell line is the HAP2 cell line deposited under DSM ACC3220, or a functional variant thereof, preferably with a similar gene expression profile. Specifically, the functional variants are characterized by substantially the same gene expression profile, i.e., the functional variant comprises a genome, wherein the level of expression of the genes is substantially the same, e.g. the gene expression level of less than 1000 genes would differ, preferably less than 750, or less than 500, or less than 300 genes.

The cell line designated HAP2 is a fully haploid human cell line, which is provided as biological material deposited at the DSMZ—Deutsche Sammlung von Mikroorganismen und Zellkulturen, Mascheroder Weg 1b/Inhoffenstraβe 7B, 38124 Braunschweig (DE) under the accession number DSM ACC3220 (deposition date: Nov. 21, 2013; depositor: Haplogen GmbH, Vienna, Austria). The HAP2 cell line and functional variants comprise the complete set of human chromosomes in the monosomic state, even for at least 20 passages. Functional variants are preferably characterized by a similar gene expression pattern. Different clones of the cell line may show the same or similar gene expression pattern. For example, independent clones may be produced by mutating a parental clone, which independent clones are karyotypically stable and have substantially the same gene expression profile.

The cell line of the invention turned out to be karyotypically stable, preferred examples, such as the deposited material or functional variants thereof. The HAP2 cell line and functional variants comprise the complete set of human chromosomes in the monosomic state, even for at least 20 passages. Functional variants are preferably characterized by a similar gene expression pattern.

Different clones of the cell line of the invention may show the same or similar gene expression pattern. For example, when producing the HAP2 cell line as deposited, at least two clones have been derived from independent rounds of transfection with Cas9 and guide RNAs and identified which are karyotypically stable and have substantially the same gene expression profile. For example, two different clones provided according to the invention differ in the expression of only 284 genes.

According to a specific aspect, cells of the cell line comprise the complete set of human chromosomes in the monosomic state.

Specifically, the haploid karyotype is karyotypically stable over at least 10 passages, preferably over at least 20 passages.

According to a specific aspect, the cell line comprises one or more genomic mutations of interest (MOI) at a predefined genomic site of interest (GOI).

The MOI is specifically at least one of
(i) a mutation knocking out the function of a gene;
(ii) a mutation introducing at least one of a deletion, substitution, or insertion of one or more nucleotides; and/or
(iii) a mutation introducing an exchange sequence of a homology template.

Such MOI may specifically include frameshift mutations that disrupt gene function or gene expression (gene knockouts), defined point mutations (knock-ins), insertions of foreign DNA sequences that are non-naturally present (e.g. tags such as GFP or the TAP tag) or deletions of sequences that are naturally present (e.g. deletions of entire genes, exons or regulatory elements).

The mutation knocking out the function of a gene may e.g. down-modulate DNA expression, delete at least part of the gene and/or disrupt the open reading frame of the gene.

Specifically, the cell may comprise the exchange sequence in total or in part, e.g. such that the part of the exchange sequence is introduced into the cell which comprises at least one point mutation and optionally further mutations that may be present within the exchange sequence as compared to the GOI.

The exchange sequence may particularly be introduced by a homology template which is a human DNA fragment or a plasmid containing such fragment comprising a recombining sequence of at least 20 bp having a sequence homology of at least 90% to the GOI and capable of homologous recombination with the GOI, and an exchange sequence comprising a human nucleotide sequence that differs from the GOI in at least one point mutation. Specifically, the cell may comprise the exchange sequence in total or in part, e.g. such that the part of the exchange sequence is introduced into the cell which comprises at least one point mutation and optionally further mutations that may be present within the exchange sequence as compared to the GOI.

By such exchange sequence, a mutation may be knocked-in into a predetermined position. The mutation which is a knock-in mutation, may e.g. comprise the knock-in of individual point mutations or SNPs.

Specifically, the homology template is
a) an oligonucleotide of 20-200 bp length, specifically 20-100 bp; or
b) a PCR product of 20-5000 bp length, specifically 20-1000 bp; or
c) any of a) or b) comprised in a donor plasmid.

The exchange sequence may comprise only one point mutation, such as the substitution of one or more nucleotides thereby encoding a different amino acid, or a series of point mutations, e.g. to obtain a pattern of mutations, sometimes referred to as SNPs (Single Nucleotide Polymorphism) wherein a single nucleotide—A, T, C or G—in the genome differs between human beings or paired chromosomes, or the insert of larger constructs, e.g. such that endogenous genes are modified to contain a specific sequence tag (myc tag, His tag, HA tag, V5 tag, TAP tag, LAP tag, GFP, RFP, dsRed, mCherry). The exchange sequence may encompass non-coding or coding regions. Typically, the exchange sequence identifies a specific gene expression pattern or product, or a specific phenotype, including genetic predisposition or disorders, or disease conditions.

Specifically, the exchange sequence is embedded into a recombining sequence, or overlapping with the recombining sequence, or flanked by one or more recombining sequences, preferably comprising the exchange sequence and flanking sequences at the 5'-end and 3'-end capable of homologous recombination with the GOI. Specific examples refer to homology templates, wherein the recombining sequence incorporates the mutation, thus, the exchange sequence is incorporated into the recombining sequence. According to an alternative example, an exchange sequence is used which is larger than the recombining sequence. Thereby a larger segment within the GOI may be exchanged, e.g. to introduce more than one point mutations. Typically, the exchange sequence has a length of 1-1000 bp, typically at least 10 bp, or at least 20 bp, and may be even larger than 1000 bp, up to 5000 bp.

Specifically, the exchange sequence has a sequence homology of at least 90%, or at least 95%, at least 98%, or at least 99% to the GOI, preferably wherein the exchange sequence comprises one or more point mutations, specifically a sequence homology of less than 99.9% or less than 99.5% as compared to the GOI, or a modified DNA region causing a different DNA expression and/or a different phenotype.

Specific mutations or mutation pattern may be introduced by the CRISPR/CAS9 method, or alternative methods of mutagenesis.

The cell line may be used to produce diploid cell lines by duplication of chromosomes to obtain sister chromosomes, or endoreduplication of the set of chromosomes, thereby obtaining duplicated or identical sister chromosomes.

Such diploid cell line is specifically understood to comprise duplicated chromosomes, e.g. of near-haploid or fully haploid cells, so to obtain a near-diploid or fully-diploid cell. The duplicated chromosomes are specifically a set of duplicated sister chromosomes, or at least part thereof, wherein the duplicated region comprises homozygous SNPs, and is specifically characterized by the absence of heterozygous SNPs.

Specifically, in the cell line of the invention, the alleles of the sister chromosomes are identical and do not contain heterozygous single nucleotide polymorphisms (SNP). Identical sister chromosomes are specifically characterized by the homozygous SNPs or SNP pattern (or the absence of heterozygous SNPs).

Specifically, a diploid cell comprising two sets of duplicated sister chromosomes is produced from an adherent cell line of a somatic haploid (or near-haploid cell), e.g. by cultivating said cell line in a monolayer cell culture asexually replicating the chromosomes within the cells, thereby obtaining a population of individual cells, specifically adherent cells, and upon determination of the karyotype of individual cells, selecting a diploid cell, and expanding the diploid cell to obtain an adherent cell line comprising a diploid karyotype.

The cell line designated C665 (also referred to as diploid eHAP) is a diploid human cell line that is considered near-diploid (because it contains duplicated chromosomes of the near-haploid cell line HAP1), and which is provided as biological material deposited under DSM ACC3250 at the DSMZ—Deutsche Sammlung von Mikroorganismen und Zellkulturen, Mascheroder Weg 1b/Inhoffenstraße 7B, 38124 Braunschweig (DE), date of deposit: Oct. 29, 2014; depositor: Haplogen Genomics GmbH, Vienna, Austria).

A diploid cell line obtained by diploidization of the fully haploid cell line as described herein is considered fully diploid. Upon duplication of the chromosomes, the cell may comprise the complete set of duplicated chromosomes. In particular, the cell may comprise the complete set of human chromosomes in the disomic state. Upon duplication, the alleles of the sister chromosomes are identical and do not contain heterozygous single nucleotide polymorphisms (SNPs). Identical sister chromosomes are specifically characterized by the homozygous SNPs or SNP pattern (or the absence of heterozygous SNPs). Specific diploid cells as obtained upon diploidization of the cell line of the invention, are adherent cells.

Therefore, the invention further provides for a method of cultivating the cell line of the invention, asexually replicating the chromosomes within the cells, thereby obtaining a population of individual cells, and upon determination of the karyotype of individual cells, selecting a diploid cell, and further expanding the diploid cell to obtain a mutant cell line comprising a diploid karyotype.

Specifically, the haploid cell line is cultivated under cellular stress conditions for diploidization, thereby accelerating spontaneous conversion to the diploid state.

Specifically, the cellular stress conditions employ at least one of:

a) a temperature stress, preferably by heat or cold shock;
b) a physical stress, preferably by shearing force;
c) continued passaging, preferably by at least 20 or 25 passages;
d) a high cell density, preferably confluence for at least 24 hours;
e) a culture medium composition comprising a suboptimal but tolerable amount of nutrients, metabolites and/or toxins;
f) temporal lowering of oxygen levels to a suboptimal level; and
g) the presence of reactive oxygen species in the culture medium, preferably for at least 2 hours.

Such stress conditions are e.g.:

Heat shock: Exposure of the cells to higher temperatures, specifically any of the temperatures (+/−1° C.): 40° C., 42° C., 44° C., 46° C., 48° C., or 50° C., for a defined period of time (e.g. at least 1 h, 2 h, 4 h, 6 h, 8 h, up to 16 h);

Cold shock: Exposure of the cells to lower temperatures, specifically any of the temperatures (+/−2° C., however, above the freezing temperature): 0° C., 4° C., 8° C., 12° C., 16° C., 20° C., 24° C., 28° C., or 32° C., for a defined period of time (e.g. at least 1 h, 2 h, 4 h, 6 h, 8 h, up to 16 h);

Cell straining and shearing: Exposure of the cells to shearing force, e.g. by treating the adherent cells to obtain the cells in suspension, such as by treatment with trypsin or other enzymes, and aspiring the cells through a needle (e.g. at least 4, 8, 12, 16, or 20 passages through a 20-, 25- or 30-gauge needle), or mixing the suspension by physical means, or employing shearing stress to the cells when adherent to a solid carrier, by physical treatment;

High density of cells: Cells are not trypsinized in time, but are exposed to higher cell density in the cell culture dish, such as to obtain a higher density than monolayer density (e.g. at least for another 6 h, 12 h, 18 h, 24 h, 30 h, 36 h, 42 h, or 48 h at confluence);

Toxins: Treatment of cells with toxic compounds during cell culture (e.g. ricin toxin, shiga toxin or tunicamycin) in a tolerable amount, such as to obtain a level of surviving viable cells of at least 30%, preferably at least 50% or at least 70%;

Hypoxia: Temporal lowering of oxygen levels, specifically any of the amounts (+/−1% v/v): 1%, 2%, 4%, or 8% $O_2$ for a defined period of time, e.g. at least 24 h, 48 h, up to 72 h;

Presence of reactive oxygen species: Treatment of cells with hydrogen peroxide for 6 h, 12 h, 18 h, 24 h Continued passage of adherent cells, under suboptimal or optimal cell culture conditions, e.g. by at least 20, 25, 30 or 35 passages.

The cell line may further be used to obtain a preparation of genomic DNA by a DNA extraction method. Therefore, the invention further provides for a DNA preparation comprising the genomic DNA extracted from the cell line as described herein.

Any of the haploid or diploid cell lines as described herein can be subject to genomic DNA extraction, e.g. through methods of DNA extraction well-known in the art, e.g. using organic extraction, silica spin columns, and magnetic beads.

Therefore, the invention further provides for a DNA preparation comprising the genomic DNA extracted from the cell line as described herein. The genomic DNA extracted from a haploid cell has the unique property of carrying only one copy of each gene, and when it comes to preparing mixtures of genomic DNA, this can have a significant impact on the ability to create more uniform mixtures. Such preparation of genomic DNA can be used as a uniform standard preparation of genomic DNA, e.g. for use as a reference standard for any mutant or native (non-mutant) cell. By using haploid cells or even haploid cells driven to diploid status (diploidized cells, where the genome of haploid cells is duplicated to obtain the diploid status), these differences between alleles are significantly reduced, making for a more uniform standard preparation.

The invention further provides for a polyclonal population of adherent somatic cells, which is composed of cell lines of at least 2 different or independent clones, wherein each of the cell lines is a haploid or diploid cell line as described herein.

Specifically, the population is a heterogeneous mixture, such as a mixture of isolated clones with the desired karyotype, comprising at least 2, 3, 4, 5, 10, or 20 different clones, e.g. on only one solid carrier or on different carriers or compartments, e.g. wherein each clone is located at spatially distinct positions. Such mix of clones is specifically suitable to provide a stable population in which genetic drift of isolated single clones is compensated by the polyclonal nature of the mix.

Specifically, the population comprises functional variants which are independent clones. The genomic or karyotypic stability of the individual clones of such population can be determined, to select those, which are karyotypically stable as defined herein, and may be further produced as a cell line that can be provided as a commercial product, or further engineered to obtain mutants.

According to the invention, there is further provided a method of producing the haploid cell line of the invention, comprising a) providing a somatic near-haploid human parental cell;

b) identifying a disomic region in the genome of the parental cell;

c) targeting the lateral sites adjacent to the 5' and 3' end of the DNA of the chromosomal region, each by a guide RNA (gRNA) comprising a tracrRNA in conjunction with crRNA including an oligonucleotide sequence that hybridizes with the target site;

d) cleaving the DNA at the target sites upon contact with an RNA-guided endonuclease which catalyzes the DNA double-strand break upon hybridizing with the gRNA, thereby deleting the chromosomal region and obtaining a fully haploid cell; and e) expanding the cell to obtain a fully haploid cell line.

In parallel transfection rounds it is possible to produce functional variants which are independent clones. It is preferred to further determine the genomic or karyotypic stability of the individual clones, to select those, which are karyotypically stable as defined herein, and may be further produced as a cell line that can be provided as a commercial product, or further engineered to obtain mutants.

The guide RNA may be provided as a binary complex of tracrRNA and a crRNA, and optional further linker sequences, each provided as separate components that associate ex vivo or within a cell. Alternatively, tracrRNA and crRNA may also be provided as separate components. Preferably, the guide RNA is provided as a chimeric or recombination product which comprises the components tracrRNA and crRNA linked to each other, e.g. by a linkage where the crRNA is linked to the 5' end of the tracrRNA directly, with or without a linker sequence, e.g. a sequence of SEQ ID 48.

The crRNA typically comprises a constant part, which is the 3' part that provides for the association or linkage with the tracrRNA. The crRNA further comprises a variable part, designed to hybridize with a specific target site, which is typically incorporated in the 5' part or 5' end of the crRNA and gRNA, respectively.

According to a specific aspect, a component consisting of the RNA-guided endonuclease in conjunction with the tracrRNA may be used. Such component is preferably used in combination with the target specific RNA (crRNA).

The guide RNA and the RNA-guided endonuclease may be conveniently provided as a ternary complex of the endonuclease with the tracrRNA and the crRNA, each provided as separate components that associate ex vivo or within a cell. Preferably, there is provided a binary complex of the endonuclease with the guide RNA, each provided as separate components that associate ex vivo or within a cell. In such complex with the endonuclease, the guide RNA preferably comprises the tracrRNA and the crRNA linked to each other, thus is a chimeric RNA product.

Preferably functional pairs of tracrRNA or gRNA paired with an RNA-guided endonuclease are used, e.g. a functional pair of the constant part of the gRNA and the endonuclease, specifically functional pairs in a complex or as separate components. Specifically, the functional pairs are of a suitable type II CRISPR systems, such as a CRISPR system of bacterial origin.

Functional pairs of the tracrRNA/gRNA and the matching endonuclease are preferably used with one or more different crRNA components, e.g. with a series of crRNA oligonucleotides that target different genomic target sites.

Specifically, the cell is capable of cellular repair mechanism, e.g. non-homologous end joining, which is optionally following a DNA break.

Specifically, the parental cell is derived from a cancer patient, preferably a patient suffering from leukemia, such as Chronic Myelogenous Leukemia or Acute Lymphoblastic Leukemia, or a solid tumor, such as peripheral chondrosarcoma.

According to a specific aspect, at least one of the gRNAs comprises a sequence selected from the group consisting of SEQ ID 3, SEQ ID 13, SEQ ID 19, and any of SEQ ID 24-47, or a functional variant of any of the foregoing which is a co-substrate of the endonuclease.

According to another specific aspect, the endonucleases is selected from the group consisting of CAS9 enzymes originating from any of Streptococcus pyogenes, Streptococcus thermophiles, Neisseria Meningitis or Treponema Denticola, and functional variants of any of the foregoing, including Cas9 nickases or artificial enzymes, specifically including recombinant enzymes, e.g. mutant or chimeric enzymes. Specific Cas9 nickases are derived from the Cas9 of S. pyogenes and comprise an amino acid mutation at position D10A or H840A resulting in the inactivation of the catalytic activity of one nuclease domain and converting Cas9 to a "nickase" enzyme that makes single-stranded breaks at the target site.

According to a preferred embodiment, the method employs at least one of

A
the gRNA comprising the nucleotide sequence of any of SEQ ID 3, 25, or 26, or a functional variant of any of the foregoing; and
the endonuclease comprising the amino acid sequence of any of SEQ ID 1, 5, 7, 8, or 9, or a functional variant of any of the foregoing; or B
the gRNA comprising the nucleotide sequence of any of SEQ ID 13, 27-40, or a functional variant of any of the foregoing; and
the endonuclease comprising the amino acid sequence of SEQ ID 10 or 15, or a functional variant of any of the foregoing; or C
the gRNA comprising the nucleotide sequence of any of SEQ ID 19,41-47, or a functional variant of any of the foregoing; and
the endonuclease comprising the amino acid sequence of SEQ ID 16 or 21, or a functional variant of any of the foregoing.

Specifically, the cell is engineered to express the CAS9 endonuclease, optionally with one or more components of the gRNA, or with the gRNA.

Specifically, the DNA break is a double strand break or a paired single strand break, proximal to a protospacer associated motif (PAM), preferably 3 by upstream of the PAM. Exemplary PAM sequences are selected from the group consisting of SEQ ID 2, SEQ ID 11, SEQ ID 12, SEQ ID 17, SEQ ID 18, SEQ ID 23, SEQ ID 75 and SEQ ID 76, or a complementary sequence of any of the foregoing. The paired single strand break is herein sometimes referred to as a specific embodiment of a "double strand" break. The paired nicking (single strand break) is specifically proximal to two PAMs, one PAM for each single strand break.

The complementary DNA sequences are typically recognized for the DNA break of the complementary strand. It is preferred that a suitable PAM sequence is selected which is recognized by the specific endonuclease and the specific CRISPR system.

According to a further specific aspect, the genomic mutation is obtained by cellular repair mechanisms induced by the DNA break, preferably introducing at least one frameshift mutation, insertion, substitution and/or deletion of one or more nucleotides.

According to a further specific aspect, the mutation refers to larger areas of mutations. For example, an exon of the gene or the entire gene is deleted.

Therefore, the method specifically employs at least two DNA double-strand breaks (DSB), wherein at least one DSB is performed within a target site proximal to the 5' end and at least one DSB is performed within a target site proximal to the 3' end of the chromosomal region. Such DSB may result from two single strand breaks within a target region, which are located at different positions on the target site on each DNA strand, e.g. proximal to each other and in sum would provide for the DSB, or a DSB at the same position of the target site on each DNA strand.

According to a specific aspect, the deleted chromosomal region has a length of at least 1 million bp, preferably at least 10 million or at least 20 million bp. It was surprising that even a megabase scale deletion of 30 million by was possible with a human near-haploid cell, to obtain the fully haploid cell line of the invention, which was karyotypically stable.

Specifically, a double strand DNA break may be induced according to the invention, employing two crRNA molecules hybridizing on both sides lateral to the genomic (chromosomal) region to be excised, e.g. proximal or adjacent to the 5' and 3' end of the genomic region. Upon such DNA break the cellular repair would provide for the joining of the free ends, thereby excising the genomic region.

According to a further specific aspect, at least two different target sites are targeted by different crRNAs or gRNAs, employing the same or different functional pairs of tracrRNA and endonuclease or functional pairs of the constant part of gRNA and endonuclease.

According to the invention, there is further provided the use of the cell line of the invention for producing isogenic cell variants, comprising genomic mutations at different genomic target sites. Such genomic mutations, e.g. comprising the knock-out of individual genes, may be produced by a method of producing a mutant somatic human cell line of cells comprising a genomic mutation at a predefined genomic target site, which comprises:

a) providing a guide RNA comprising a tracrRNA in conjunction with crRNA including an oligonucleotide sequence that hybridizes with the target site;
b) providing an RNA-guided endonuclease which catalyzes the DNA break at the target site upon hybridizing with the gRNA;
c) introducing the guide RNA into the cells in the presence of the endonuclease to obtain a repertoire of cells comprising a variety of genomic mutations at the target site;
d) selecting a cell from said repertoire which comprises a mutation knocking out the function of a gene; and
e) expanding the cell to obtain the mutant cell line.

Specifically, the method employs
a) an expression plasmid incorporating a nucleic acid sequence to express the guide RNA used to transform the cells and to obtain a repertoire of transformant cells comprising the variety of genomic mutations at the target site, e.g. proximal to the target site; and
b) a transformant cell from said repertoire is selected that comprises the mutation knocking out the function of a gene.

Further methods may employ insertional mutagens, such as gene traps delivered by retroviruses or transposons, or other designer nucleases, such as Zinc finger nucleases or TALENs.

Specifically, the genomic mutation is obtained by cellular repair mechanisms induced by the DNA break, preferably introducing at least one frameshift mutation, insertion, substitution and/or deletion of one or more nucleotides.

For example, a genomic mutation could be obtained by HDR in the presence of a donor template, or by NHEJ if one wants to obtain frameshift mutants.

Specifically, a MOI may be obtained by any of the following methods:

1. Mutations are introduced by CRISPR/Cas-mediated breakage of DNA. To this end, at least one guide RNA and a Cas9 nickase can be used to introduce a single-strand break. However, more than one guide RNA (two in a specific embodiment: paired nicking) can be used, and Cas9 wild-type or nickase can be used.
2. Following cleavage, the cells will repair the DNA damage either by NHEJ or homology-directed repair (HDR), or other mechanisms. There are further possible repair pathways, e.g. including base-excision repair, mismatch repair or single strand annealing.
3. Mutations include:
   a. Small insertions of deletions (indels). If an exon is targeted, such mutations disrupt the frameshift (frameshift mutations) and the resulting cell line would qualify as a gene knockout. Such mutations are e.g. obtained by
      i. Single guide and Cas9 wt, followed by NHEJ;
      ii. Paired guides and Cas9 nickase, followed by NHEJ;
   b. Single nucleotide substitutions or point mutations. Such mutations are e.g. obtained by
      i. Single guide, Cas9 wt and donor template, followed by HDR;
      ii. Paired guides, Cas9 nickase and donor template, followed by HDR;
   c. Deletions of sequences that are naturally present. Such mutations are e.g. obtained by
      i. Paired guides (deleted sequence lies between the two guide RNAs) and Cas9 wt, followed by spontaneous end joining (NHEJ);
   d. Insertion of sequences that are naturally present (e.g. as genes or exons) or non-naturally present (e.g. GFP, Myc tag). Such mutations are e.g. obtained by
      i. Single guide, Cas9 wt and donor template, followed by HDR;
      ii. Paired guides, Cas9 nickase and donor template, followed by HDR;

For example, specific repair mechanisms integrating a nucleotide sequence include any of the following:

1. NHEJ-Mediated Integration

While the integration of a foreign exchange sequence (e.g. GFP) is usually achieved by homology-directed repair, it can also be obtained by non-homologous end joining. To this end, one can use a plasmid containing the exchange sequence, flanked by a guide RNA recognition site that is not present in the human genome. If such a plasmid is co-transfected with Cas9, a guide RNA that targets the human genome and a guide RNA that targets the recognition sites present in the plasmid, the exchange sequence will get liberated in cells expressing Cas9. Following liberation, it can be integrated in the human genome in a targeted fashion. The resulting cell line will carry a single integration of the exchange sequence, proximal to the site that was targeted in the human genome.

2. DNA Repair Mechanisms

DNA double-strand breaks, induced by Cas9, are repaired by NHEJ or HDR. While NHEJ is well understood, the mechanisms governing HDR are less well characterized. Though HDR is synonymously used with homologous recombination, it can be more complex and other repair pathways may additionally contribute. For instance, it has been shown that the mismatch repair pathway suppresses HDR and consequently, MSH2 or PMS2 knockout cells display higher rates of HDR. In addition, the contribution of other repair pathways may depend on the nature and the length of the donor template. For instance, when short oligonucleotides are used as donors, it has been speculated that incorporation is aided by DNA replication factors, similar to Okazaki fragments. With longer donors, factors involved in homologous recombination may contribute more.

Such mutation(s) are typically localized within 20 by upstream and downstream of the DNA double-strand break, specifically within 15 by or 10 by upstream and downstream of the DNA break. The mutation(s) specifically provided are located at one or more positions, e.g. at least 1 or 2 point mutations, including single insertions, deletions or substitutions of one or more basepairs, specifically at least 3, 4, 5, up to 10 point mutations.

According to a specific aspect the incorporation of the exchange sequence, (herein also referred to as mutation(s)) are localized within 500 by upstream and downstream of the DNA break, specifically within 250 by or 100 by upstream and downstream of the DNA break and more specifically within 50 by or 10 by upstream and downstream of the DNA break.

Specifically, the invention provides for a method of producing a library of somatic fully haploid human cells comprising genomic mutations (a MOI) at different genomic target sites (a GOI), by mutagenizing cells of a cell line of the invention.

According to the invention, there is further provided a library of somatic fully haploid, karyotypically stable human cells comprising a repertoire of isogenic cell variants comprising genomic mutations at different genomic target sites.

Specifically, the method of the invention provides for producing a library of such mutant human somatic cell lines of isogenic cells with a variety of genomic mutations at different predefined genomic target sites. Such library differs from libraries of the prior art, because of the fully haploid cells with a stable haploid karyotype and characteristic mutations, in particular the frameshift mutations or knock-out mutations, which are characteristic for the CRISPR system, i.e. mutations proximal to a PAM sequence.

Therefore, the invention further provides for a library of mutant human somatic cell lines of isogenic cells with a variety of genomic mutations at different predefined genomic target sites, wherein the cells are haploid with a stable haploid karyotype for the genomic locus of the target sites, obtainable by the method of the invention.

Specifically, the library comprises a repertoire of at least 50 cell lines with mutations at different genomic target sites, preferably at least 100, preferably at least 300, at least 1.000 or at least 10.000.

According to a specific embodiment, each cell line of a cell line repertoire or library is provided in separate containers.

According to a further specific embodiment, the library is comprised in an array including microarrays, wherein each cell line is located at spatially distinct positions, e.g. spots. Therefore, the invention provides for such array comprising the library of the invention.

The library can be used for specific screening purposes. Therefore, the invention provides for a method of identifying a human somatic cell line comprising a MOI at a predefined GOI by determining the functional characteristics of one or more cell lines of a library as described herein, and selecting a cell line according to its function as an indicator of the MOI.

FIGURES

FIG. 1: Sequence information of functional pairs of tracrRNA or gRNA and RNA-guided CAS9 endonuclease of *S. pyogenes*:

A)
amino acid sequence of CAS9 (SEQ ID 1)
PAM motif (SEQ ID 2)
gRNA (SEQ ID 3)
constant part of the gRNA, including the constant part of crRNA, a linker and the tracrRNA (SEQ ID 4)
B)
amino acid sequence of CAS9 with an additional NLS sequence located in the N-terminal extension of the amino acid sequence of SEQ ID 1(SEQ ID 5)
NLS sequence (SEQ ID 6)
C)
amino acid sequence of CAS9 with an additional NLS sequence located in the C-terminal extension of the amino acid sequence of SEQ ID 1(SEQ ID 7)
D)
amino acid sequence of CAS9 with an additional NLS sequence located in the N-terminal extension, and an additional NLS sequence located in the C-terminal extension of the amino acid sequence of SEQ ID 1 (SEQ ID 8)
E)
amino acid sequence of CAS9 with an additional NLS sequence located in the N-terminal extension, and an additional NLS sequence located in the C-terminal extension of the amino acid sequence of SEQ ID 1 (SEQ ID 9)

FIG. 2: Sequence information of functional pairs of tracrRNA or gRNA and RNA-guided CAS9 endonuclease of *S. thermophilus*:
A)
amino acid sequence of CAS9 (SEQ ID 10)
PAM motif (SEQ ID 11)
Exemplary PAM motif (SEQ ID 12)
gRNA (SEQ ID 13)
constant part of the gRNA, including the constant part of crRNA, a linker and the tracrRNA (SEQ ID 14)
B)
amino acid sequence of CAS9 with three additional NLS sequences (SEQ ID 6) located in the C-terminal extension of the amino acid sequence of SEQ ID 10 (SEQ ID 15)

FIG. 3: Sequence information of functional pairs of tracrRNA or gRNA and RNA-guided CAS9 endonuclease of *N. meningitis*:
A)
amino acid sequence of CAS9 (SEQ ID 16)
PAM motif (SEQ ID 17), or (SEQ ID 75), or (SEQ ID 76)
Exemplary PAM motif (SEQ ID 18)
gRNA (SEQ ID 19)
constant part of the gRNA, including the constant part of crRNA, a linker and the tracrRNA (SEQ ID 20)
B)
amino acid sequence of CAS9 with three additional NLS sequences (SEQ ID 6) located in the C-terminal extension of the amino acid sequence of SEQ ID 16 (SEQ ID 21)

FIG. 4: Sequence information of functional pairs of tracrRNA or gRNA and RNA-guided CAS9 endonuclease of *T. denticola*:
A)
amino acid sequence of CAS9 (SEQ ID 22)
PAM motif (SEQ ID 23)
B)
amino acid sequence of CAS9 with three additional NLS sequences (SEQ ID 6) located in the C-terminal extension of the amino acid sequence of SEQ ID 22 (SEQ ID 24)

FIG. 5: Functional gRNA sequences, including functional variants of parent sequences (SEQ ID 25-47), linker GAAA (SEQ ID 48).

FIG. 6: Spectral karyotyping (SKY) data for KBM-7 cells reveal two copies of chromosome 8 and a portion of chromosome 15, attached to chromosome 19.

Figure 7:
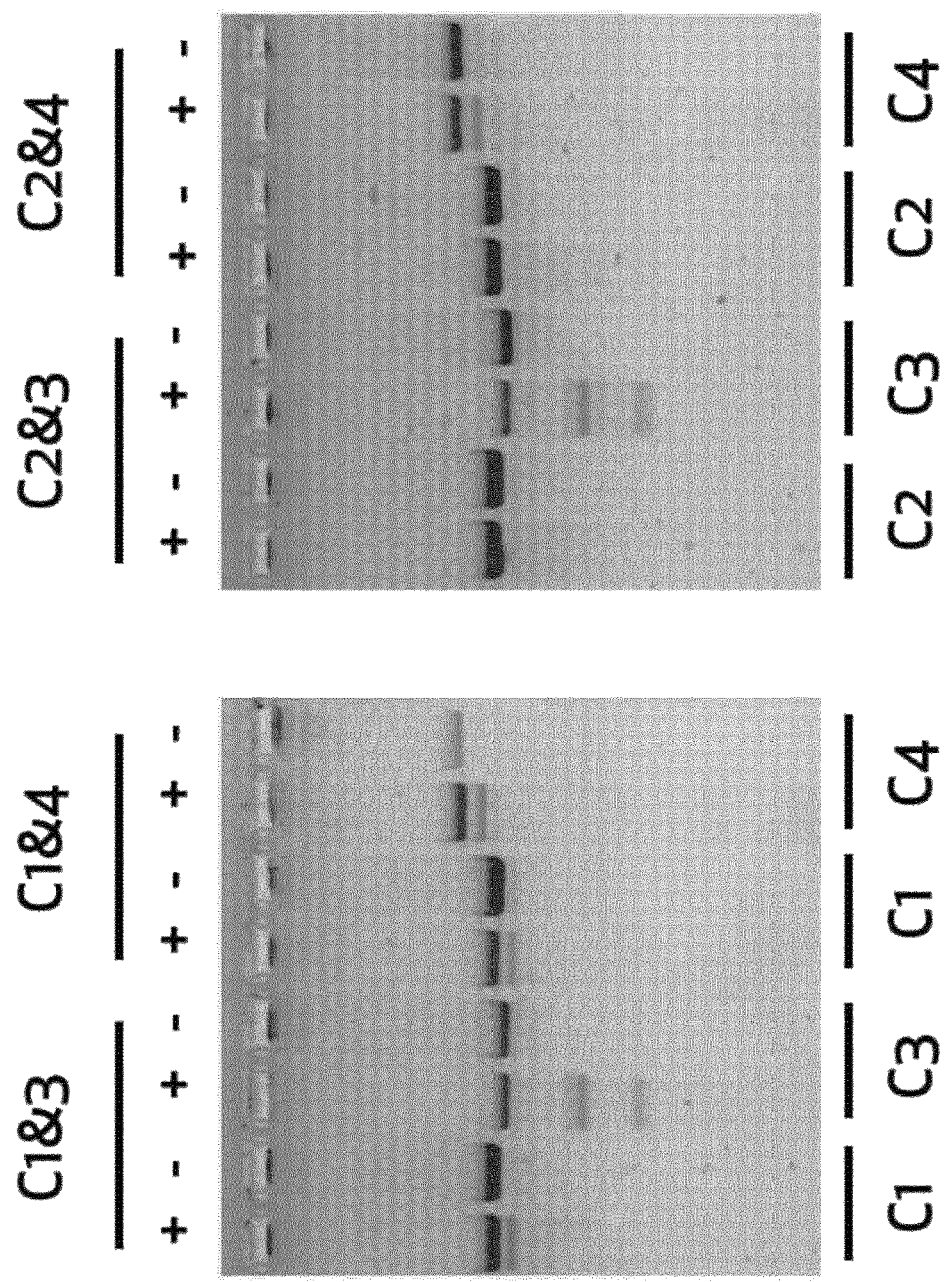

FIG. 7: T7 endonuclease assay from transfected pools of HAP1 cells. HAP1 cells were transfected with four different combinations of two CRISPRs (C1&3, C1&4, C2&3, C2&4), targeting each boundary of the disomic region with one CRISPR. Genomic DNA was isolated from pools of transduced cells. Editing at each locus was assessed by PCR and T7 endonuclease digestion.

Figure 8:
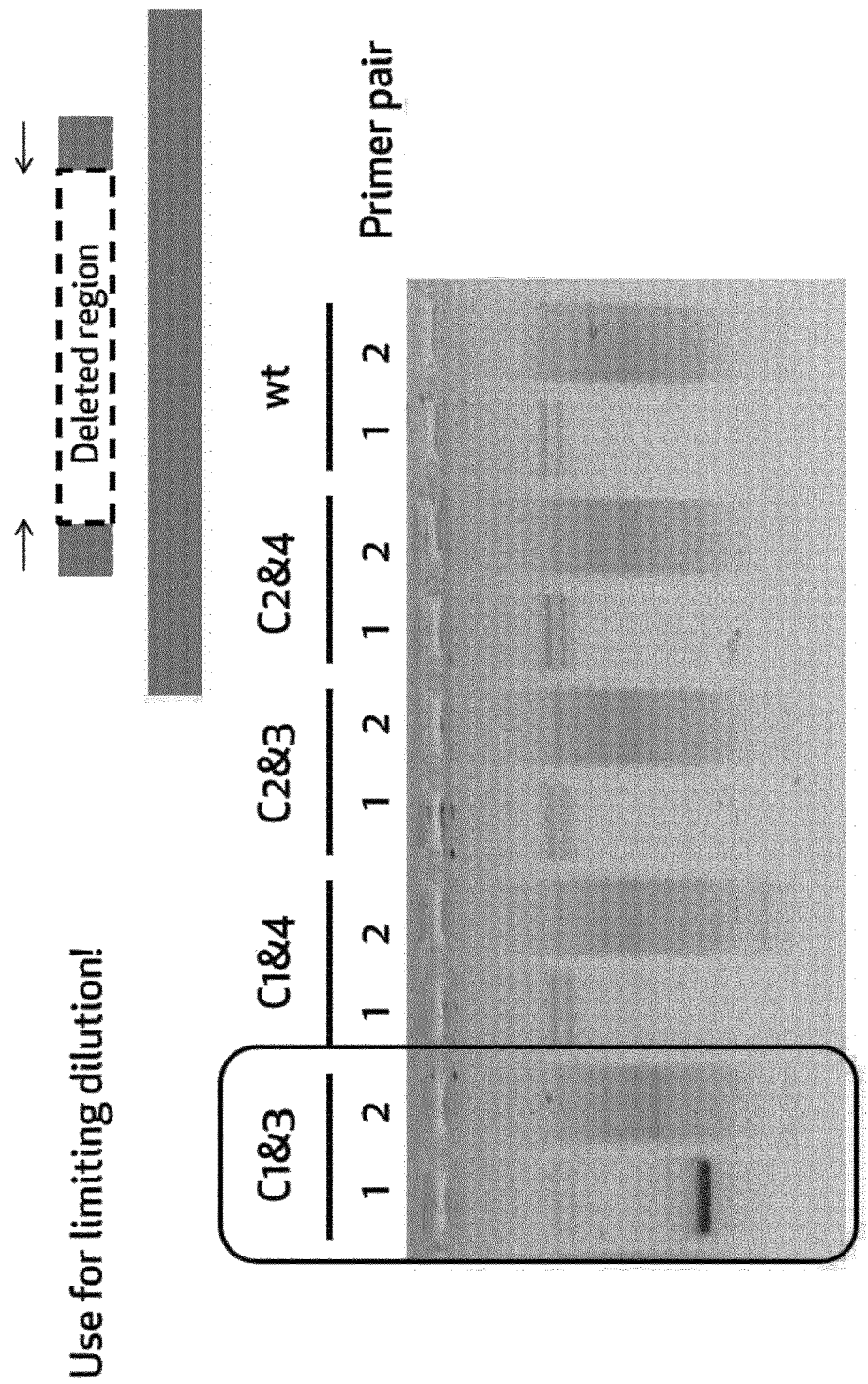

FIG. 8: Deletion PCR from pools of CRISPR-transfected cells. HAP1 cells were transfected with four different combinations of two CRISPRs (C1&3, C1&4, C2&3, C2&4), targeting each boundary of the disomic region with one CRISPR. Genomic DNA was isolated from pools of transduced cells. Two primer pairs flanking the deleted regions were used for PCR amplification, enabling the detection of a deletion-specific PCR amplicon that is not present in HAP1 wild-type cells.

Figure 9:
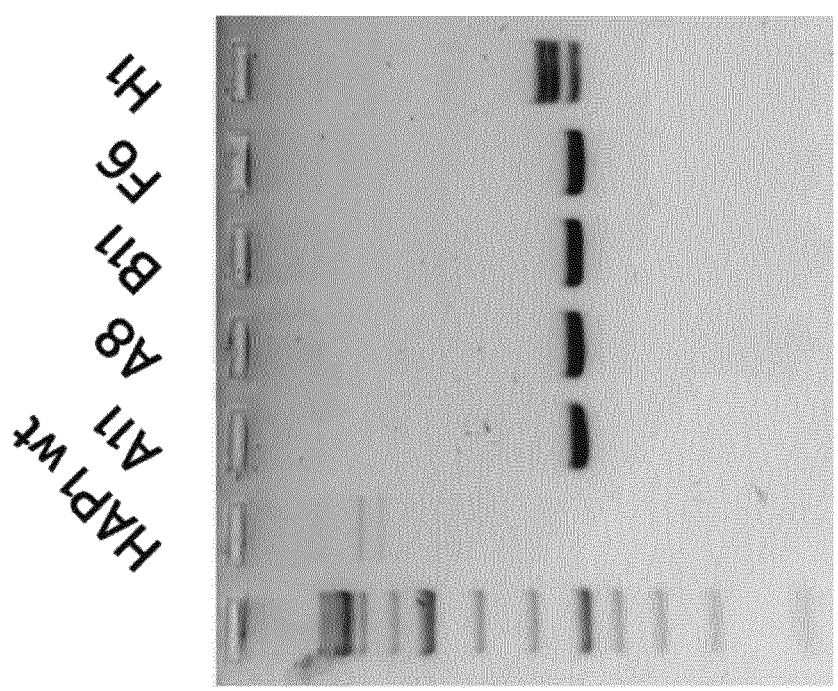

FIG. 9: Deletion PCR on individual clones. Individual HAP1 clones (designated A11, A8, B11, F6 and H1) were isolated from pools of CRISPR-transfected cells by limiting dilution. Genomic DNA was isolated from each clone and analyzed by PCR, using a primer pair enabling the detection of a deletion-specific PCR amplicon that is not present in HAP1 wild-type cells.

Figure 10:
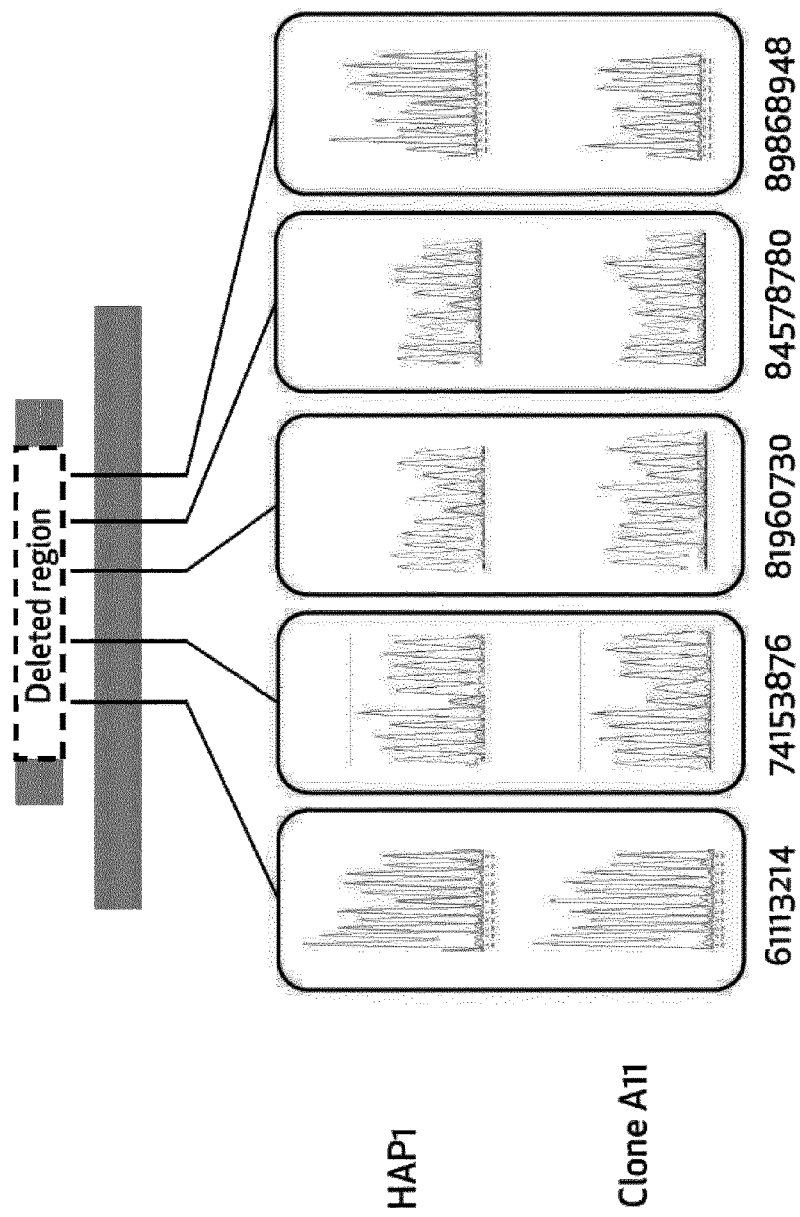

FIG. 10: Clone A11 is hemizygous at five genomic loci for which HAP1 cells are heterozygous. Five regions that contain heterozygous SNPs within the disomic region on chromosome 15 were amplified by PCR and subjected to Sanger sequencing. While HAP1 cells are heterozygous for all five SNPs, clone A11 displays loss of heterozygosity.

Figure 11:
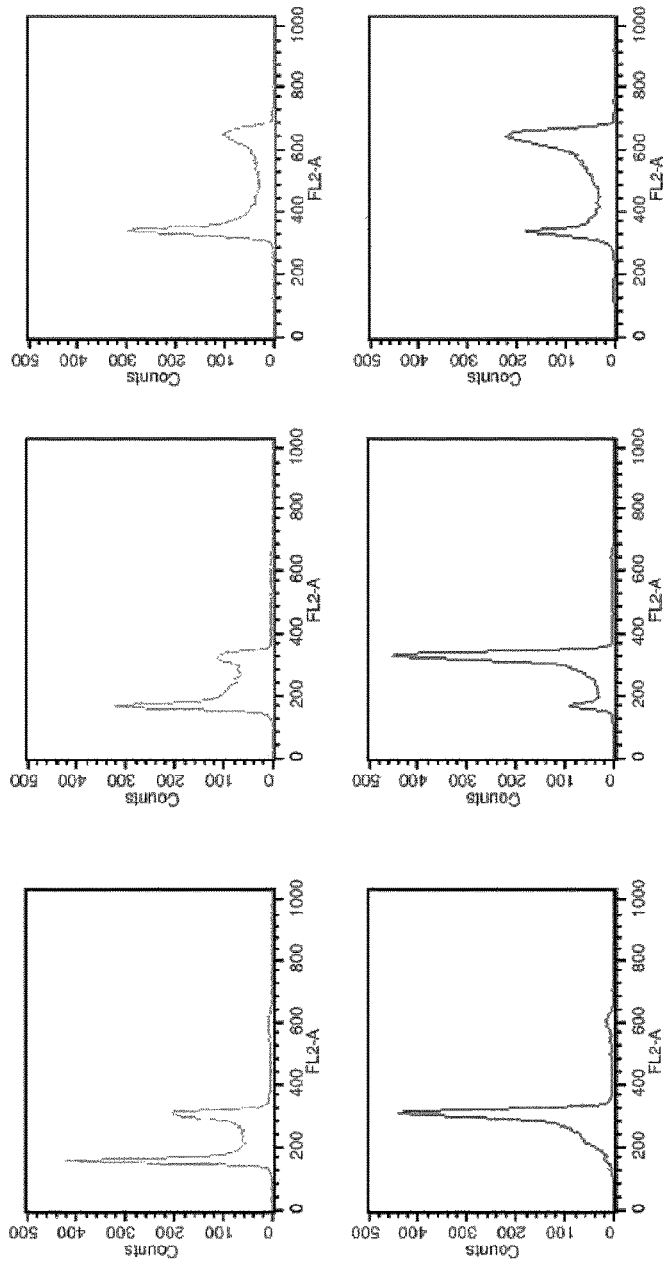

FIG. 11: Clone A11 is haploid. Three cell lines (clone A11, a haploid control (KBM-7) and a diploid KBM-7 clone 085) were stained with propidium iodide. Propidium iodide intercalates in the genomic DNA and thus provides a quantative measure for total DNA content. Propidium iodide staining was quantified by flow cytometry.

Figure 12:
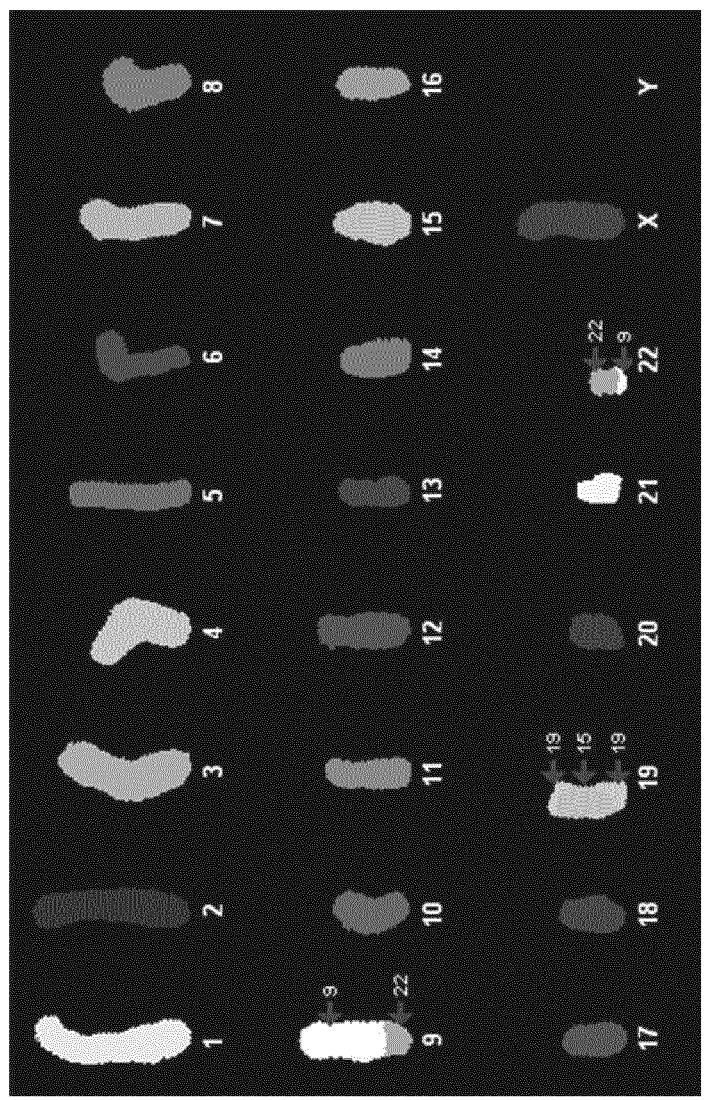

FIG. 12: Spectral karyotypic staining of HAP1 cells. HAP1 cells were analyzed by spectral karyotyping to assess the global genomic landscape of these clones.

Figure 13:
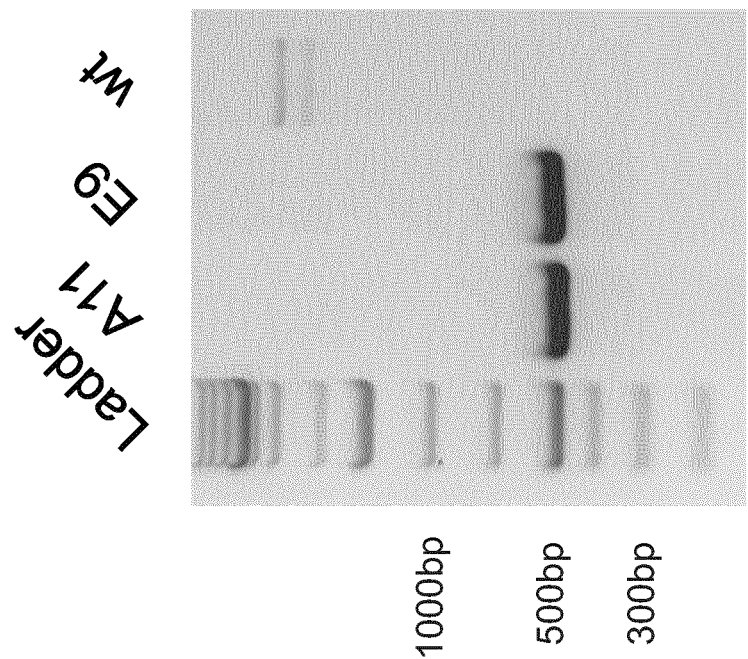

FIG. 13: Deletion PCR for clones A11 and E9, as well as HAP1 wt cells. To assess whether the fragment between guide RNAs 1 and 3 had been excised following Cas9 cleavage, a deletion PCR was performed using a forward primer (HG6090) that binds to position chr15:61,105,055 and a reverse primer (HG6093) that binds to position chr15:89,889,818.

Figure 14:
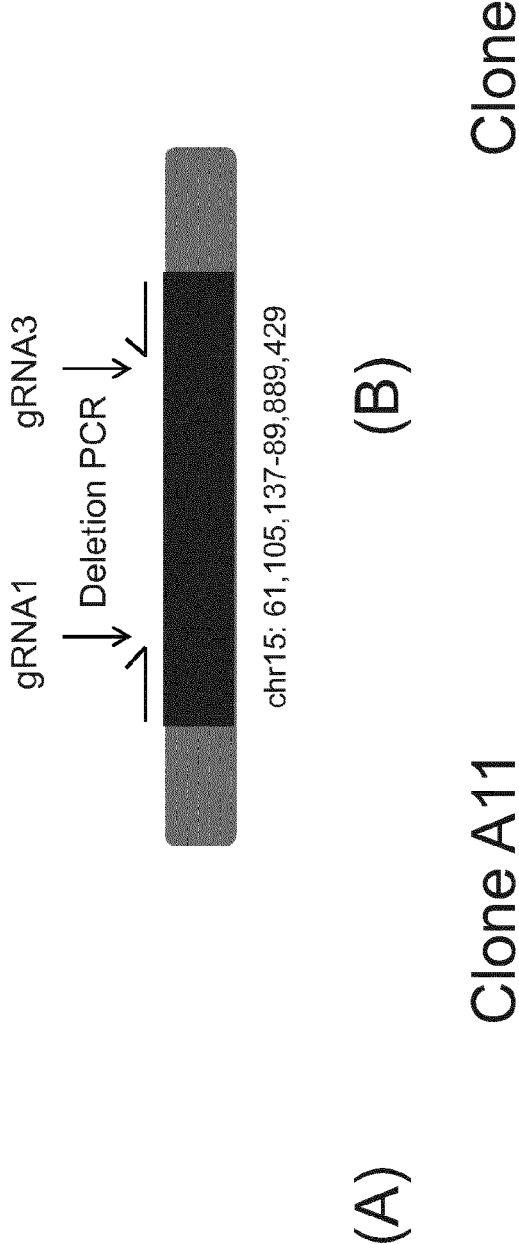

FIG. 14 Clones A11 and E9 arose from different editing events. Deletion PCR products obtained from clones A11 and E9 (FIG. 1) were sent for Sanger sequencing and aligned to the human genome.

Sequence shown for clone A11 (SEQ ID 95):
CCAGAAGGGGCATGTCCTATCATTGTAATAAAAAAGGACACTGCCAGTT

TCTGAACTATAGTGACACCACCAAGGCAACGGTAGATGTGGCTGAGAGC

CCTGCCCTTGAGCCTTTTGGCTTGAGGCTTCATGCCAGCATCCACGGAG

```
GCACAGCTTCAGGGTCCCTGGTGGCCCAGCCACTGGGCAAGAGAGGATG

CTCTTTTCCATCCCTGGGTCTGGCTAGAGGCCCTGGAGGGAGTCAGGGT

CCTTGCCAAAGAGCAGCAGAGCCTGCCGTGAAGTGAAGGCTTCTGAAAG

AAATGAGTCTGAATCCTGGCTCCACCTGTCCAAACTGTGTGACCTTAAG

CAAATTACAAGGGAGCTTGCTGTGCCTCAGCATCCTTGTCTCTATAATG

GGAAGGTGATAGCCTCATAGGGGGCTTGTGAGGTTT

Sequence shown for clone E9 (SEQ ID 96):
CCAGAAGGGGCATGTCCTATCATTGTAATAAAAAAAGGACACTGCCAGT

TTCTGAACTATAGTGACACCACCAAGGCAACGGGACCGGTAGATGTGGC

TGAGAGCCCTGCCCTTGAGCCTTTTGGCTTGAGGCTTCATGCCAGCATC

CACGGAGGCACAGCTTCAGGGTCCCTGGTGGCCCAGCCACTGGGCAAGA

GAGGATGCTCTTTTCCATCCCTGGGTCTGGCTAGAGGCCCTGGAGGGAG

TCAGGGTCCTTGCCAAAGAGCAGCAGAGCCTGCCGTGAAGTGAAGGCTT

CTGAAAGAAATGAGTCTGAATCCTGGCTCCACCTGTCCAAACTGTGTGA

CCTTAAGCAAATTACAAGGGAGCTTGCTGTGCCTCAGCATCCTTGTCTC

TATAATGGGAAGGTGATAGCCTCATAGGGGGCTTGTGAGGTTT
```

Figure 15:
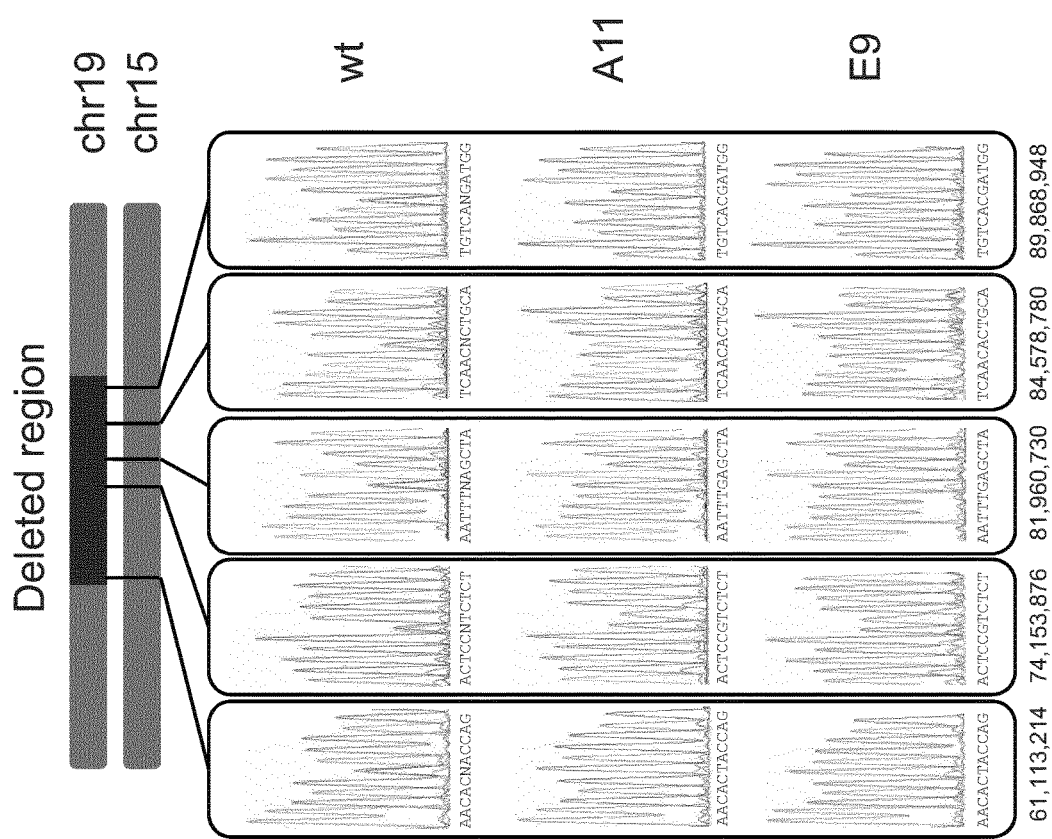

FIG. 15 Loss-of-heterozygosity in clones A11 and E9. To assess loss-of-heterozygosity in clones A11 and E9, genomic DNA was isolated and five genomic loci containing SNPs that were heterozygous in HAP1 cells were selected. Each locus was amplified by suitable PCR primers and the PCR products were sent for Sanger sequencing.

Sequences contained in FIG. 15:

```
61,113,214 in wt:
                                            (SEQ ID 80)
AACACNACCAG 61,113,214 in A11:
                                            (SEQ ID 81)
AACACTACCAG 61,113,214 in E9:
                                            (SEQ ID 82)
AACACTACCAG 74,153,876 in wt:
                                            (SEQ ID 83)
ACTCCNTCTCT 74,153,876 in A11:
                                            (SEQ ID 84)
ACTCCGTCTCT 74,153,876 in E9:
                                            (SEQ ID 85)
ACTCCGTCTCT 81,960,730 in wt:
                                            (SEQ ID 86)
AATTTNAGCTA 81,960,730 in A11:
                                            (SEQ ID 87)
AATTTGAGCTA 81,960,730 in E9:
                                            (SEQ ID 88)
AATTTGAGCTA 84,578,780 in wt:
                                            (SEQ ID 89)
TCAACNCTGCA 84,578,780 in A11:
                                            (SEQ ID 90)
TCAACACTGCA 84,578,780 in E9:
                                            (SEQ ID 91)
TCAACACTGCA 89,868,948 in wt:
                                            (SEQ ID 92)
TGTCANGATGG 89,868,948 in A11:
                                            (SEQ ID 93)
TGTCACGATGG 89,868,948 in E9:
                                            (SEQ ID 94)
TGTCACGATGG

Wherein N = any of A, C, T, or G
```

FIG. 16: Clones A11 and E9 are fully haploid human cell lines. Clones A11 and E9 were analyzed by spectral karyotyping to assess the global genomic landscape of these clones.

Figure 17:
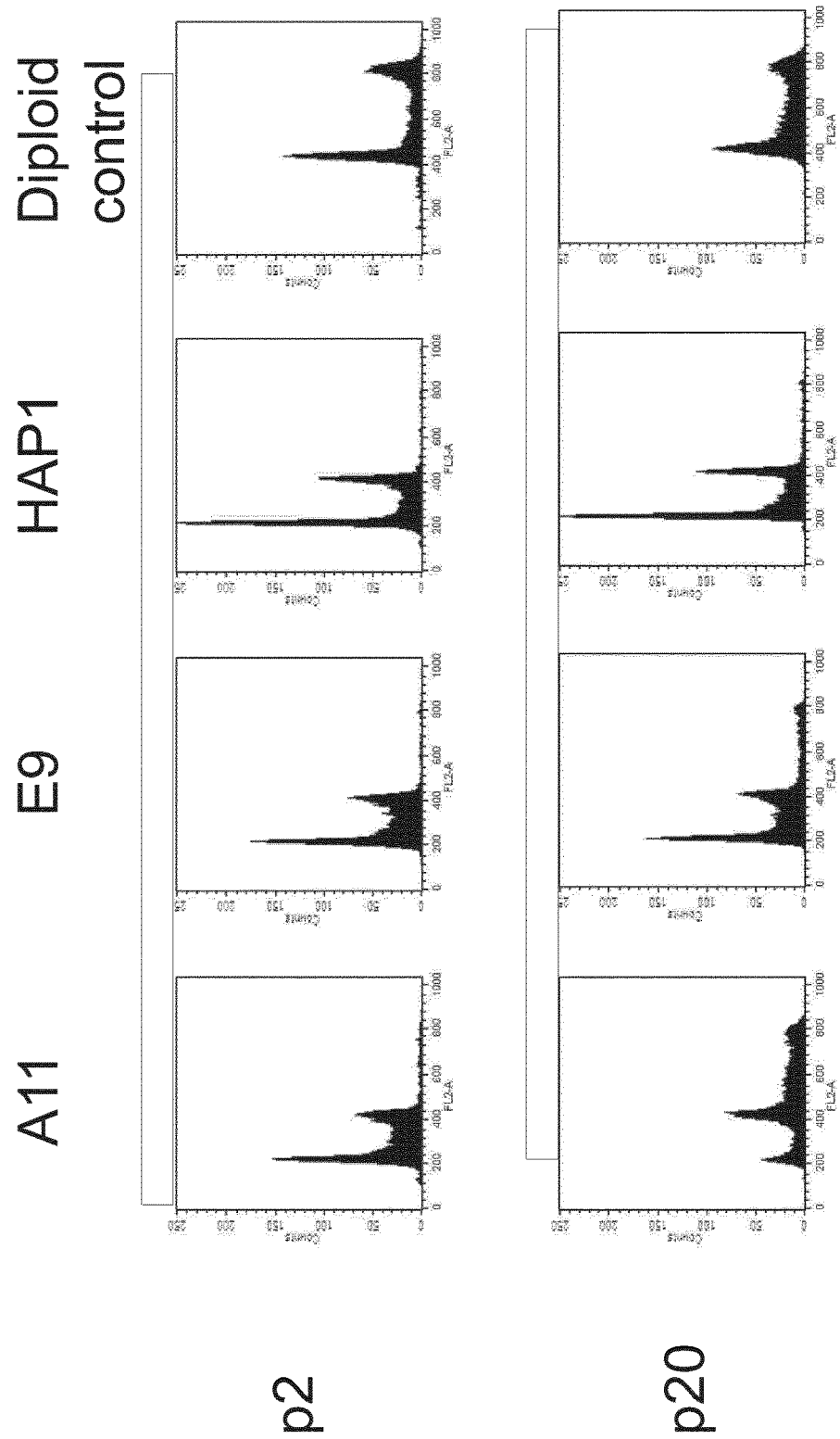

FIG. 17: Karyotypic stability of clones A11 and E9. Clones A11 and E9, as well as HAP1 wt cells, were passaged as indicated (for two passages or twenty passages). Following passaging, cells were stained by propidium iodide staining to assess the ploidy. A diploid control cell lines was included for reference.

Figure 18:
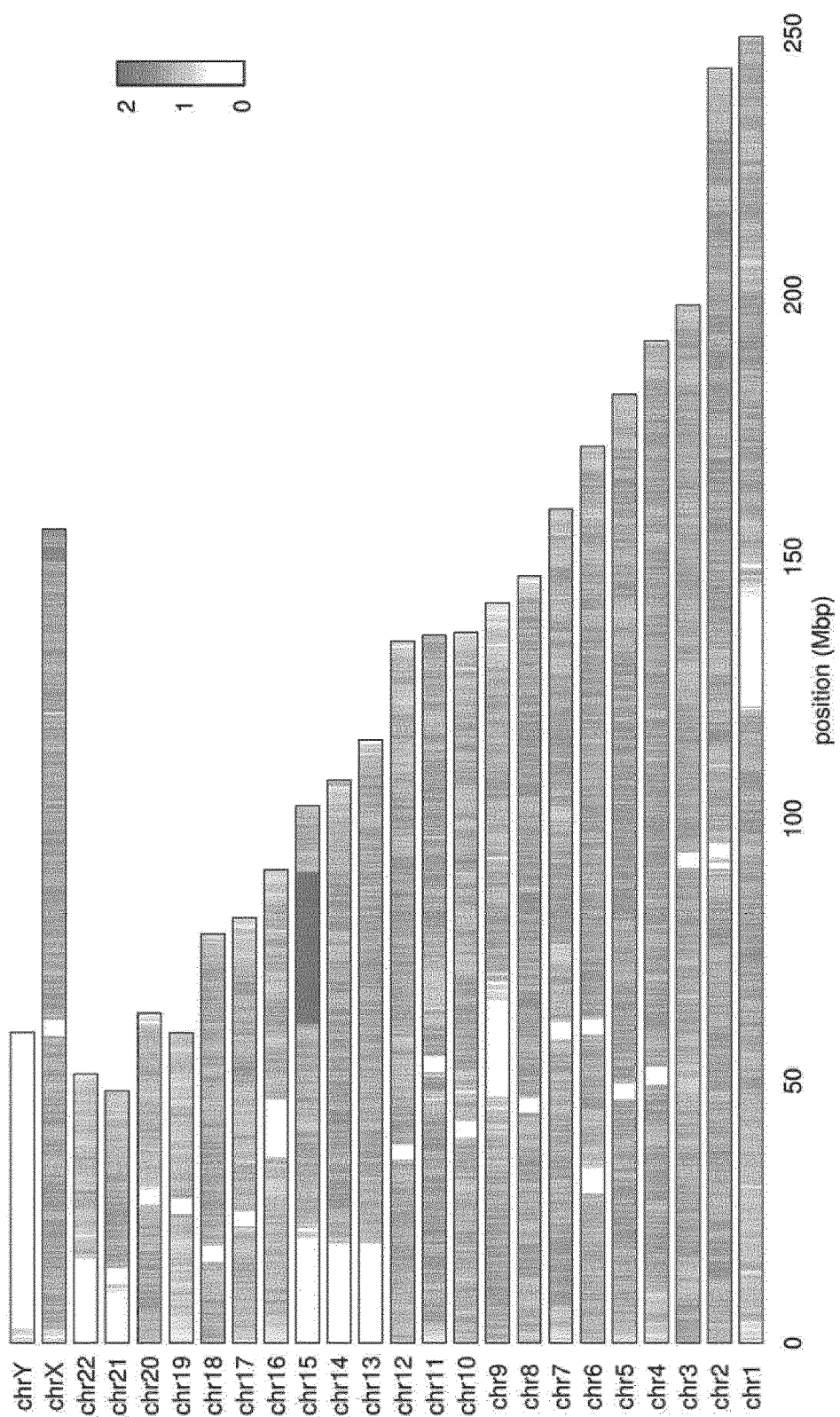

FIG. 18: Genomic changes in clone E9 are largely confined to chromosome 15. Whole genome sequencing was performed on parental HAP1 cells and clone E9. In this panel, relative coverage between HAP1 and E9 data reveals a copy number loss restricted to the edited chr15 fragment. Large white regions correspond to unassembled pieces of the human genome.

Figure 19:
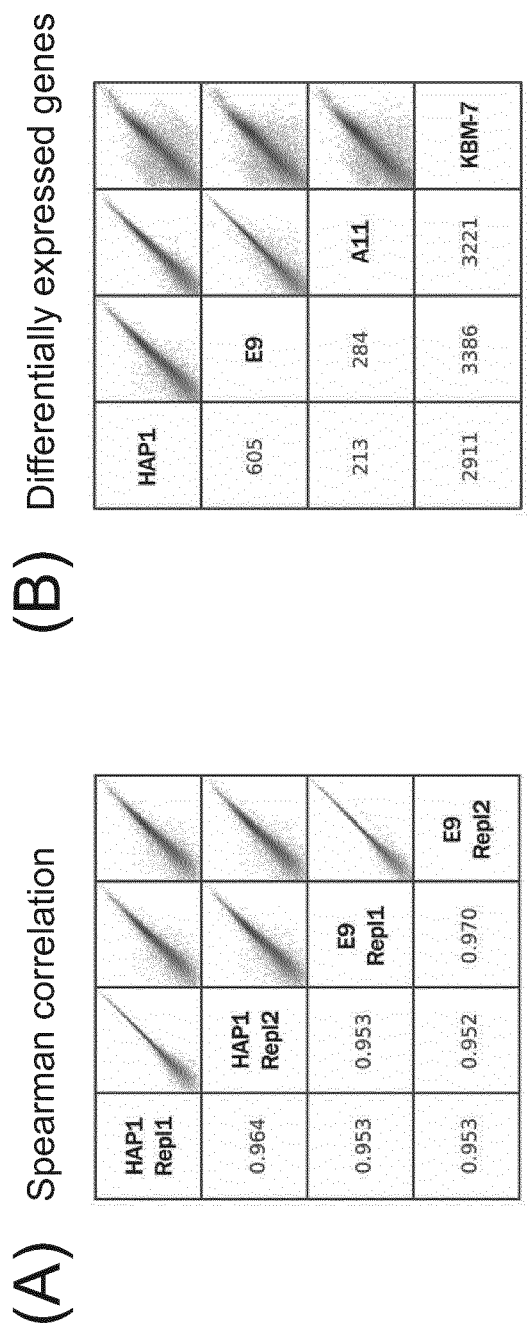

FIG. 19: RNA sequencing highlights overall similarity of clones A11 and E9 to their HAP1 parents. (A) Two biological replicates of HAP1 cells and two technical replicates of the E9 clone were subjected to RNA-sequencing. Spearman correlations between the samples show overall expression is consistent between the parental line and the edited clones. (B) Two replicates of each cell line were compared pairwise. The number of highly expressed (FPKM>5) and two-fold differentially expressed genes are indicated.

Figure 20:
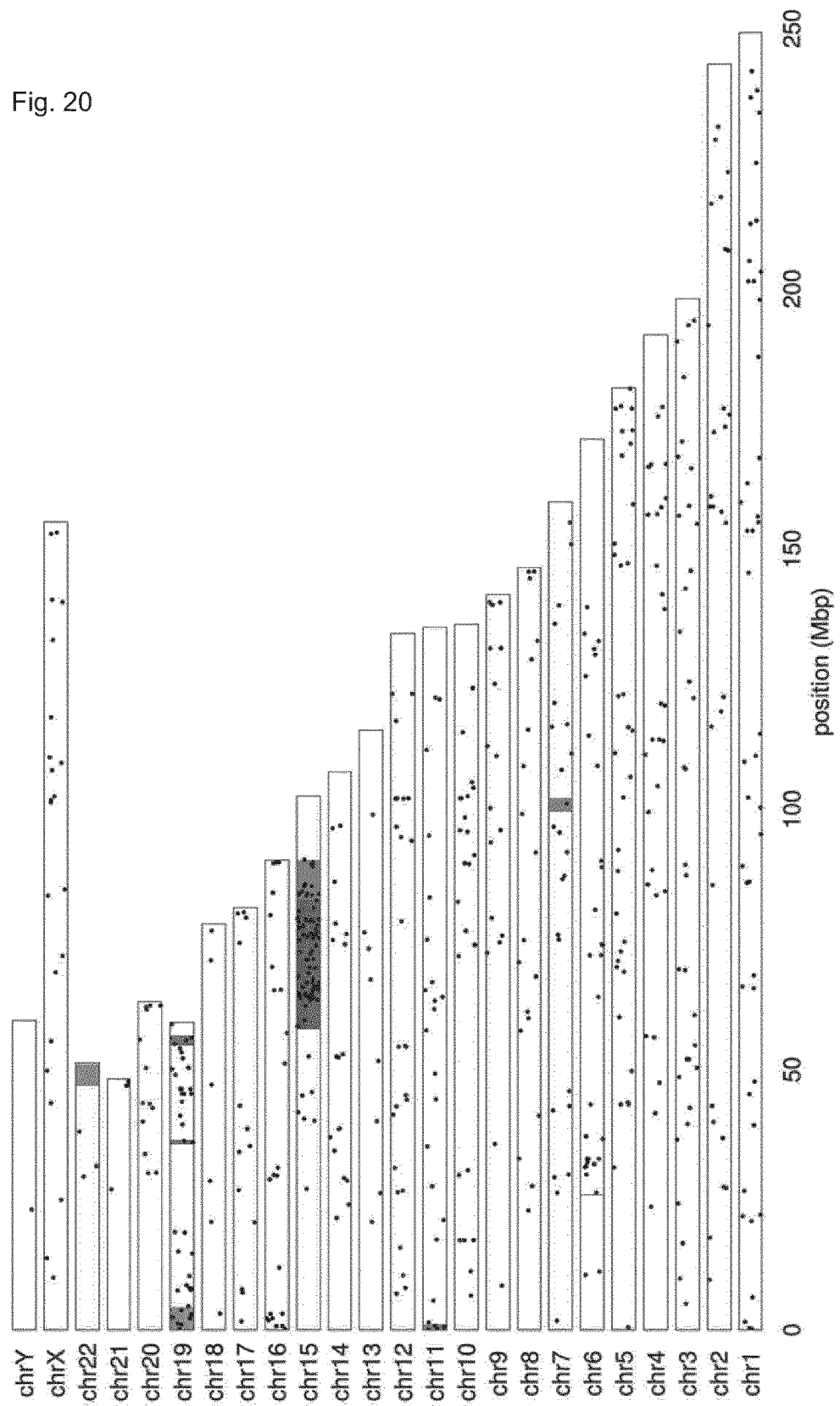

FIG. 20: Transcriptomic changes in clone E9 are largely confined to chromosome 15. HAP1 cells and clone E9 were analyzed by unbiased RNA sequencing to assess global changes in gene expression. Expression ratios between HAP1 and E9 cells were subjected to segmentation analysis. The heatmap shows expression changes are mainly localized on the edited chromosome. The inset reveals the details of the segmentation.

Figure 21:
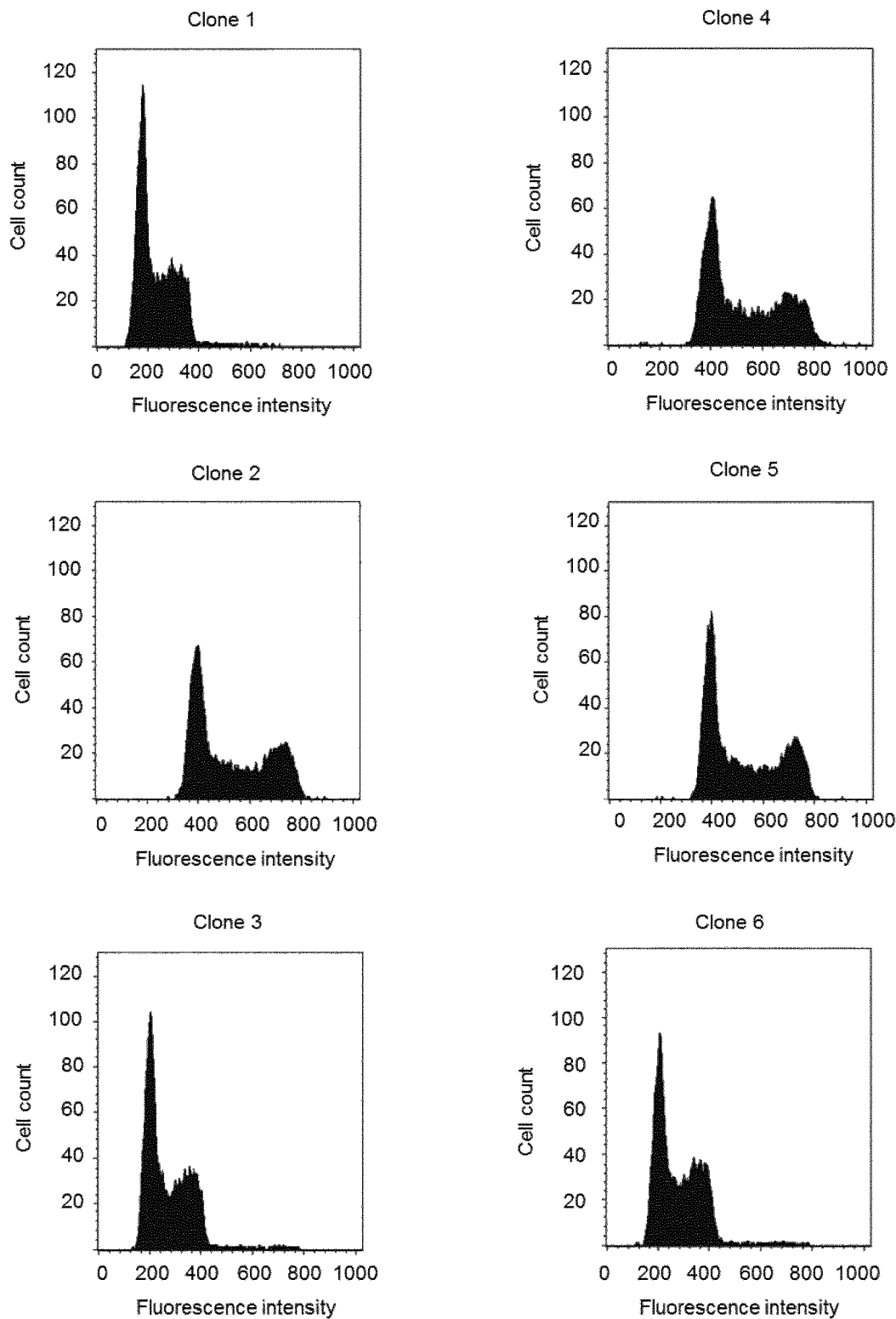

FIG. 21: Single-cell clones isolated from a population of HAP1 can be haploid or diploid. Six clones (designated clones 1-6) were isolated by limiting dilution and analyzed by propidium iodide staining and FACS. Clones 1, 3 and 6 are haploid, whereas clones 2, 4 and 5 are diploid.

Figure 22:
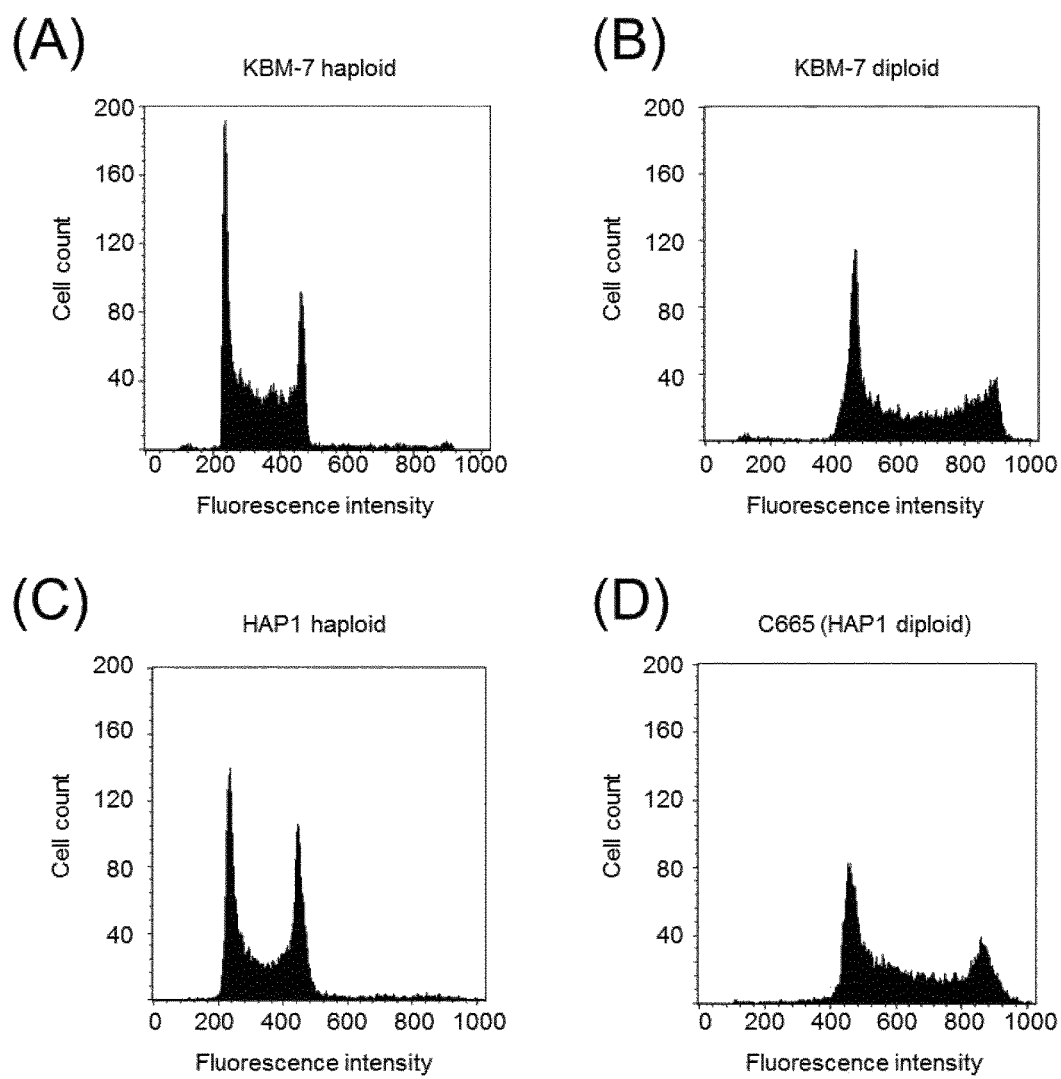

FIG. 22: Haploid and diploid cell lines can be derived from KBM-7 and HAP1 cells. Multiple haploid clones or diploid clones, derived from KBM-7 and HAP1, were pooled to give rise to stable haploid or diploid cell lines. The resulting cell lines were analyzed by propidium iodide staining and FACS. Panels A and B display KBM-7-derived cell lines, panels C and D display HAP1-derived cell lines.

FIG. 23: Spectral karyotyping analysis of cell line C665. Cell line C665 (diploid HAP1 cells) were analyzed by spectral karyotyping. Panels A, B and C represent independent C665 sub-clones that show distinct karyotypes.

DETAILED DESCRIPTION OF THE INVENTION

Specific terms as used throughout the specification have the following meaning.

The term "cell line" as used herein shall mean an established clone of a particular cell type that has acquired the ability to proliferate over a prolonged period of time, specifically including immortal cell lines, cell strains and primary cultures of cells. The term is specifically used for haploid or diploid cell lines, in particular for cell lines of somatic cells. The term specifically encompasses wild-type, e.g. cells which are naturally occurring and can be found in nature or can be isolated from a source in nature and which has not been intentionally modified by man in the laboratory, or mutant cell lines, which comprise a genomic mutation, e.g. at a coding or non-coding site in the genome, as compared to a wild-type cell line. Also, when introducing a mutation of interest at a GOI, the non-mutated nucleotide sequence is herein referred to as wild-type or parent one. Further, a cell is considered wild-type, if no mutation has been introduced into the genome despite the fact that the cell is not naturally-occurring, but artificially produced. Therefore, the term "wild-type" shall not only apply to human cell lines obtained by culturing parent cells that are obtained from a human being, but also to artificial cells which comprise a human genome, either haploid or diploid. The term specifically encompasses human cell lines that are obtained by engineering cells which originate from a human being, specifically cells including alterations of the diploidy or haploidy of the chromosome. Parent cells may further comprise a mutation of individual exons, or genes, in particular introducing site directed mutations.

The cell line may be a eukaryotic and specifically a human cell line, which is understood as a cell line comprising the human genetic code, with or without mutations or otherwise alterations. Therefore, the term shall not only apply to human cell lines derived from parent cells that are obtained from a human being. The term also encompasses human cell lines that are obtained by engineering cells which originate from a human being, specifically cells including alterations of the diploidy or haploidy of the chromosome, or mutation of individual exons, or genes, in particular knocking out the function of a gene and/or introducing site directed mutations.

Isolated clones or a population or mixtures of isolated clones are herein referred to as artificial products, in particular, clones which are not naturally-occurring. Specifically; the diploid cell lines as described herein which comprise duplicated sister chromosomes and homozygous SNPs, are not occurring in nature, because native (naturally-occurring) somatic diploid cells would always comprise heterozygous SNPs.

Mutant cell lines may be recombinant cell lines employing recombination means and methods to obtain a recombinant DNA, thus obtained by recombinantly engineering the cell genome. Such recombinant engineering typically employs artificial constructs like plasmids or oligonucleotides or RNA/DNA or respective fragments, as tools to produce a recombined DNA. Specific mutants may be obtained by mutating a (chromosomal) region, thereby obtaining a genomic mutation at a specific locus of the chromosome. A mutant recombinant DNA may specifically be produced by either random or targeted recombination. Exemplary mutated cells comprise at least one genetic element exogenous to the cell that is integrated into the cell genome. In some aspects, the exogenous genetic element can be integrated at a random location in the cell genome. In other aspects, the genetic element is integrated at a specific site in the genome. For example, the genetic element may be integrated at a specific position such as to provide a change relative to the endogenous sequence.

Further exemplary mutated cells comprise an insertion or deletion of a coding or non-coding sequence, e.g. to produce a phenotype different from the parent cell. Mutated cells may also include cell lines in which individual nucleotides have been substituted.

Alternatively, the cells may be mutagenized by evolutionary mechanisms, e.g. using cells with normal or increased spontaneous mutation rate. Upon recombination or mutagenesis, a suitable mutant cell line may be selected according to its specific genetic sequence, e.g. by determining the specific alteration of the sequence.

It is understood that mutant cell lines may be provided as a product ready-to-use for cultivation, e.g. for research, industrial or analytical use. It is well understood that the human cell lines as specifically described herein are somatic cell lines, thus, the scope of the present invention does not encompass human beings or techniques directly related to human germline manipulation or human cloning.

Specific cell lines as described herein are adherent cell lines, thus, can be cultivated as adherent cells to surfaces or in suspension, e.g. in presence or absence of solid carriers. Cell line culture can be done for instance in dishes, roller bottles or in bioreactors, using batch, fed-batch, continuous systems, hollow fiber, and the like.

The adherent cells typically are cultures on a solid surface in the form of a monolayer culture. Anchorage-dependent cell lines growing in monolayers are typically subcultured at regular intervals to maintain them in exponential growth. When the cells are near the end of exponential growth (roughly 70 to 90% confluent), they are usually subcultured, thereby undergoing a passage. The passage from a primary culture to a secondary culture is characterized by a split ratio which represents the proportion of the primary culture in the form of detached cells which is required for seeding a further culture device at a given cell density and thereby providing the secondary culture.

Adherent cells typically anchorage loosely or strongly on a cell support or carrier. Exemplary carriers on which cells would grow are known in the art and preferably are adapted to the purpose of cell cultivation. The carrier is suitably a particulate carrier. Carriers may be made of any suitable material supporting cell growth, such as, dextran, plastic, gelatine, collagen or cellulose, glass or others. Conventional adherent cell culture employs surfaces of tissue culture bottles, vials, well slides or other vessels, or microcarriers involving growing adherent cells as monolayers on the surface of small micron range diameter particles which are usually suspended in culture medium.

In a cell culture of adherent cells, most cells attach firmly to the solid surface. In some cases, cells round up and detach somewhat during mitosis. Following mitosis, they will reattach.

Standard protocols of cultivating adherent cells are known in the art, e.g. of Life Technologies. These include method steps of cell cultivation, cell dissociation, counting cells, determining optimal seeding density and preparing new culture vessels for passaged cells. Adherent cell lines will grow in vitro until they have covered the surface or the medium is depleted of nutrients. At this point the cell lines are typically subcultured in order to prevent the culture from dying. To subculture the cells they need to be brought into suspension, e.g. using a detachment buffer. The degree of adhesion varies from cell line to cell line but in the majority of cases proteases, e.g. trypsin, are used to detach and release the cells from the solid surface. Adhesion of cells to the carrier is promoted by alkaline earth metal salts such as calcium and magnesium salts. Therefore, the detachment buffer suitably does not contain any components which promote cell adhesion and, for example, alkaline earth metal salts such as calcium and magnesium salts are suitably avoided. In principle, cells are detached from a carrier to which they are adhered by a number of well-known enzymatic means. The most common means of detachment is using proteolytic degradation, most typically employing a cysteine or serine endopeptidase, such as trypsin, but also papain, actinidin, bromelain or ficin may be used.

The term "cellular stress conditions" as used herein is understood in the following way. When the cell is under stress, e.g. arising from oxidation, heat, infection, toxic contamination or any other stressful condition, they can mount a variety of responses. Some of these are generic; others are more specific to the stress-inducing agent. Physiological or non-physiological (e.g. physical) stressors would cause the cells to react in various specific ways to stress. Well-established markers for stress include (i) upregulation of heat-shock proteins (such as HSP70 or HSP90), (ii) activation of stress-induced kinases (such as SAPK, CHK1 or CHK2), (iii) activation of caspases (such as CASP3 or CASP7), (iv) upregulation of HIF-1 and other hypoxia-inducible factors in response to hypoxia, (v) activation of the unfolded protein response in response to cellular stress at the endoplasmatic reticulum, (vi) temporary cell cycle arrest in response to high cell density.

Such cellular stress conditions as described herein would enhance the spontaneous diploidization of a haploid genome. The stress conditions can be employed to a culture of adherent cells when attached on the solid surface or upon detachment, before cells are re-attached to a solid surface to further cultivate the cells. Shearing is suitably applied after detachment, treatment with toxins is advantageously applied to adherent cells.

The term "cellular repair mechanism" as used herein is specifically understood as mechanisms to detect and repair the various types of damage that can occur to DNA. A specific DNA damage is single-strand or double-strand breaks, which may be highly deleterious possibly leading to loss or rearrangement of genomic sequences. Double-strand breaks are repaired through non-homologous end joining (NHEJ) or homologous recombination repair (HR). In NHEJ, additional errors can be introduced during this process leading to specific mutations proximal to the DNA break. Therefore, NHEJ is considered inherently mutagenic as it relies on chance pairings, called microhomologies, between the single-stranded tails of the two DNA fragments to be joined. HR is a repair process that uses a DNA template for correction. It is more precise than NHEJ, yet less efficient. If a suitable exogenous DNA template is provided to the cells, HR offers the possibility to engineer mutations in specific GOIs.

The term "expression" as used herein shall refer to the production of RNA and/or of protein, polypeptide or peptide based on a nucleic acid molecule that is capable of directing transcription. Expression may be transient or may be stable. In the context of the present invention, the term "transcription" relates to a process, wherein the genetic code in a DNA sequence is transcribed into RNA.

"Expression constructs" or "vectors" or "plasmid" refers to nucleic acid molecules containing a desired nucleotide sequence and control sequences in operable linkage, so that hosts transformed or transfected with these sequences are capable of producing the encoded molecules. In order to effect transformation, the expression system may be included in a vector; however, the relevant DNA may also be integrated into the host chromosome. Expression plasmids are herein termed "human expression plasmids" if designed for transforming human cells.

According to the invention, the RNA specifically used in the RNA-guided system may be provided by in vitro transcription wherein RNA is in vitro synthesized in a cell-free system, preferably using appropriate cell extracts or chemical synthesis, or by in vivo transcription wherein RNA is in vivo synthesized in a cell-based system, which particularly includes ex vivo production employing the cells in an environment outside the human body.

Preferably, an expression plasmid is applied for the generation of transcripts obtained by transcription of an appropriate DNA template, which plasmids are herein specifically understood as cloning vectors. Specifically an expression plasmid employed for the purpose of the invention may be used for transient expression of gRNA, or any of the tracrRNA and the crRNA components of a gRNA.

The term "plasmid" as used herein refers to a macromolecule or complex of molecules comprising a polynucleotide to be delivered to a host cell, either in vitro or in vivo. A plasmid is typically understood as a common type of a vector, being an extra-chromosomal DNA molecule separate from the chromosomal DNA which is capable of replicating independently of the chromosomal DNA. In certain cases, it is circular and double-stranded. Thus, a plasmid specifically includes autonomously replicating nucleotide sequences as well as genome integrating nucleotide sequences. Expression plasmids usually comprise an origin for autonomous replication in the host cells, selectable markers (e.g. an amino acid synthesis gene or a gene conferring resistance to antibiotics such as blasticidin, zeocin, kanamycin, G418 or hygromycin), a number of restriction enzyme cleavage sites, a suitable promoter sequence and a transcription terminator, which components are operably linked together. The promoter for controlling transcription can be any promoter for any RNA polymerase. If transcription occurs ex vivo, one typically uses bacteriophage-derived T7, T3, and SP6 RNA polymerases in conjunction with their cognate promoters. If transcription is meant to occur in human cells, one typically uses the U6 promoter, which is derived from the human U6 snRNA locus, driving the transcription via human RNA polymerase III.

A DNA template for transcription may be obtained by cloning a nucleic acid and introducing it into a vector for delivery employing an appropriate promoter for transcription. The DNA may be obtained by reverse transcription of RNA.

The term "RNA" as used herein comprises double-stranded RNA, single-stranded RNA, isolated RNA such as partially or completely purified RNA, essentially pure RNA, synthetic RNA, and recombinantly generated RNA, such as modified RNA which is functionally the same or similar, but differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

The terms "guide RNA", "tracrRNA", and "crRNA" are understood in the following way.

A guide RNA (gRNA, also termed chimeric guide RNA) is a chimeric RNA molecule comprising the tracrRNA, which—together with the constant part of the crRNA—specifically determines the structure of the gRNA necessary to provide a co-substrate to a matching RNA-guided endonuclease, also termed chimeric guide RNA scaffold, which is understood as a constant RNA sequence forming a functional pair with an endonuclease guided by the gRNA. The crRNA comprises a constant part capable of interacting with or linking to the tracrRNA, and a variable part (also termed oligo RNA) which is composed of a short oligonucleotide sequence which is complementary to a DNA target site in the human genome. The constant part of the crRNA is typically located at the 3' part of the molecule, whereas the variable part is typically located at the 5' end of the molecule. The tracrRNA and the crRNA may directly associate though hybridizing parts, or joined with a linker sequence.

gRNA forms a co-substrate to direct RNA-guided endonuclease activity to the genomic target site where the gRNA (through its crRNA component) hybridizes with the target. Thus, the crRNA is understood as containing the part encoding the genome editing information in the form of complementary sequences (allowing GU as well as GC base pairs), and the RNA-guided DNA endonuclease is understood as a nuclease cleaving target DNA at a specific site. For example, CAS9 assembles with the chimeric gRNA in human cells and can induce the formation of a DNA breaks, e.g. a double strand DNA break at a site complementary to the gRNA sequence in genomic DNA. This cleavage activity requires both CAS9 and the complementary binding of the guide RNA through the variable crRNA part.

Therefore the gRNA as described herein is typically a non-coding RNA, specifically hybridizing with a DNA target site and directing the RNA-guided endonuclease to the DNA target site, to induce a DNA break within the region of hybridization. This system provides for invaluable tools for human genome engineering at the cellular level by reprogramming of a CRISPR-CAS system to achieve RNA-guided genome engineering in human cells.

The set of matching RNA-guided endonuclease and tracrRNA or gRNA or constant part of gRNA is herein understood as a functional pair, which may be used with one or more variable parts, i.e. with one or more crRNA or crRNA variable parts, e.g. a 20b, 22b, 24b or 26b RNA-type oligonucleotide, to target one or more predetermined, random or different human genomic target site. For example, a set of CAS endonuclease, e.g. type II, and a matching tracrRNA is used for interference of the crRNA (the oligonucleotide conjugated to the 5' end of the tracrRNA, e.g. employing a linker) with the target nucleic acid sequence through its variable crRNA oligo sequence. Targeting occurs upon hybridization of the crRNA to the complementary target site. Exemplary functional pairs of tracrRNA and endonuclease or functional pairs of gRNA and endonuclease are illustrated in FIGS. 1 to 4. Specific gRNA variants are illustrated in FIG. 5. Functional variants of the endonuclease, tracrRNA or the gRNA are feasible. In particular, gRNA variants may comprise a variable 3' end, e.g. within the region of the 20, or 15, or 10, or 6 terminal bases, such as a truncation, elongation and/or a point mutation of any of the bases in the 3' terminal RNA sequence.

Functional variants of the RNA-guided endonuclease are specifically those of the same type or subtype as obtained from bacterial sources or derived from the amino acid sequences of bacterial origin, including artificial or recombinant enzymes comprising the same or mutated sequences, e.g. comprising one or more mutations and a specific sequence identity to the wild-type sequence.

A functional variant of a CAS endonuclease may be a CAS9 nickase, which is herein understood as a CAS9 mutant comprising specific point mutations, e.g. an exchange of one or more single (non-contiguous) amino acids resulting in the inactivation of one domain with nuclease activity and converting CAS9 to a "nickase" enzyme that makes single-stranded breaks at the target site instead of a double strand break. Such nickase may as well be used for double strand DNA break, e.g. when used with paired guide RNAs to introduce targeted double-strand breaks.

Examples of wild-type enzymes and sequences are provided in FIGS. 1 to 4. Parent CAS9 enzyme sequences may be obtained from the respective coding DNA sequences or the amino acid sequences of bacterial CAS9 of *S. pyogenes, S. thermophiles, N. Meningitis* or *T. denticola*, e.g. comprising or consisting of any of the amino acid sequences of SEQ ID 1, 6, 7, 8, 9, 10, 15, 16, 21, 22, or 24. Functional variants of a parent enzyme may e.g. be analogs, such as wild-type sequences obtained from other species, e.g. other bacterial species of the same genus or family as the parent endonuclease, or mutated wild-type sequences of analogs. When an analog of the endonuclease is used, specifically the analogous tracrRNA or gRNA sequence of the same species or the same family may be used to form a functional pair, e.g. which components are natively paired.

Wild-type tracrRNA or gRNA sequences, in particular the constant part of the gRNA or tracrRNA, which is herein understood to confer a specific co-substrate structure, thus, referred to as structural part of gRNA, may be used to form a functional pair with a functional variant of the endonuclease. Alternatively, functional variants of the tracrRNA or gRNA (in particular the constant part of gRNA) may be used, e.g. which are obtained by mutagenesis of the wild-type sequences used as parent sequences.

The functionally active variant of an RNA, such as a gRNA or a component of gRNA, e.g. the tracrRNA of the invention, is specifically understood to encompass a nucleotide sequence which forms a functional co-substrate to the matching RNA-guided endonuclease, and/or any of the functionally active size variants, including truncated versions or fragments, mutants or hybrid nucleic acid sequences of a wild-type RNA. Functional variants of the RNA molecules as described herein may e.g. be obtained by one or more mutations in the nucleotide sequence of a parent (wild-type) RNA, wherein the mutated RNA is still functional and hybridizes under stringent conditions to a strand complementary to the parent RNA.

It is understood that the term "constant" with respect to a RNA sequence or a part of an RNA sequence, as used herein shall refer to the sequence of the RNA which is determined by the sequence of bacterial origin of a specific species, independent on the variability of the oligonucleotide (being part of the crRNA) which hybridizes with a target DNA. Such constant RNA molecule or part of a gRNA is typically of the same or similar structure for all cells of a specific species, and provides for interaction with the RNA-guided endonuclease of the same species thereby forming a functional pair, independent on type or origin of the genomic target site. It is well understood that such constant molecules or parts of the molecules may still vary from species to species, or be used as a parent molecule to produce mutants, which may be used as functional variants.

The "variable" part of the crRNA as described herein is understood as the part that hybridizes with a specific part of a target DNA, thus is complementary to any specific site. Since the human genomic target sites are located throughout the human genome, a plurality of oligonucleotides may be used for hybridizing the crRNA or gRNA with the target site, either with a predetermined target site or randomly targeting the human genome. Therefore, this part is considered to be variable, according to the specific hybridization target.

Functional variants of crRNA or gRNA or a constant part of the gRNA are feasible when a parent sequence is used as a template or is mutated, e.g. through mutagenesis or directed engineering, such as by engineering fragments or terminal extensions, and/or by one or more point mutations. A parent wild-type tracrRNA sequence or constant part of gRNA may e.g. comprise any of the sequences of FIGS. 1 to 5 indicated as gRNA or constant part of gRNA (i.e. the gRNA excluding the crRNA variable part which may or may not include a linker sequence), in particular the tracrRNA and constant part of the crRNA or gRNA of SEQ ID 3, SEQ ID 13, SEQ ID 19, and any of SEQ ID 24-47.

The RNA may comprise specific modifications. For example, a further modification of the RNA used in the present invention may be an extension or truncation of the naturally occurring poly(A) tail or an alteration of the 5'- or 3'-untranslated regions (UTR).

The "functionally active variant" or "functional variant" of a nucleotide or amino acid sequence as used herein specifically means a mutant sequence, e.g. resulting from modification of a parent sequence by insertion, deletion or substitution of one or more nucleotides or amino acids within the sequence or at either or both of the distal ends of the sequence, and which modification does not affect (in particular impair) the activity of this sequence.

Specifically, the functionally active variant of the sequence has substantially the same activity as a parent sequence and is selected from the group consisting of
- homologs with at least about 60% nucleotide sequence identity, preferably at least 70%, at least 80%, or at least 90% degree of homology or sequence identity to the parent sequence; and/or
- homologs obtainable by modifying the parent sequence, or the sequence of a size variant used as a template to provide for mutations, e.g. by insertion, deletion or substitution of one or more nucleotides within the sequence or at either or both of the distal ends of the sequence;
- sequence variants derived from a parent or wild-type sequence as described herein by extension and/or fragmentation of the parent sequence, e.g. +/−50% or +/−25%, or +/−10% of the length; or
- analogs derived from species other than *S. pyogenes, S. thermophiles, N. Meningitis* or *T. denticola*.

The functionally active variants as described herein are also understood to encompass hybrids or chimeras of two or more parent sequences, e.g. resulting from combination of sequences that qualify as parent sequence with functional activity.

Suitable variants have "substantially the same activity", which term is herein specifically understood to refer to the activity as indicated by substantially the same or improved efficacy of directed DNA break and/or mutagenesis, e.g. +/−50% or +/−25%, or +/−10%, as determined by the rate of successful DNA break and/or recombination.

Functional variants which have "substantially the same gene expression profile" are characterized by the same or similar expression of each of the genes.

The term "functional variant" with respect to a cell line is specifically understood as a clone which is different from a parent (or comparable) clone. Such functional variant may be independently produced, e.g. by separate or parallel engineering measures, and therefore referred to as independent. Functional variants may as well be subclones of the parent clone.

The functional variants of the HAP2 clone, such as the deposited material referred to herein, are particularly characterized by the complete set of human chromosomes which are fully haploid, and further characterized by the stable haploid karyotype. Preferred functional variants of the HAP2 clone have the same or similar gene expression profile, e.g. as determined by the level of gene expression of a number of individual genes.

Specifically, the present invention refers to the HAP2 cell line deposited under DSM ACC3220, or a functional variant thereof, preferably with a similar gene expression profile. Specifically, the functional variants are characterized by substantially the same gene expression profile, i.e., the functional variant comprises the human genome, wherein the level of expression of the genes is substantially the same, e.g. the gene expression level of less than 1000 genes would differ, preferably less than 750, or less than 500, or less than 300 genes.

For example, independently produced clones may have substantially the same gene expression profile, which is different with respect to less than 500 genes only.

For example, the independently produced clones A11 and E9 as further described herein have substantially the same gene expression profile, which is different with respect to 284 genes only.

In contrast, two cell lines cannot be considered functional equivalents of the HAP2 cell line, such as KBM-7, if they vary in the expression level of ~3,000 human genes.

The identity of the level of expression with respect to one gene in individual clones is herein understood as the same or similar level of gene expression (e.g. +/−2-fold difference) for individual genes. Thus, the expression level is considered different for an individual gene, if the level of expression of said gene is at least 2-fold higher (≥200%) or less than one half (<50%). This is understood as a conservative cut-off of 2, to determine the same or similar level of gene expression when compared to a reference clone.

A less conservative cut-off is 3, or 4, or 5, i.e. indicating a 3-fold difference, or a 4-fold difference, or a 5-fold difference. Thus, the expression level is considered different for an individual gene, if the level of expression of said gene is at least 3-fold higher (≥300%) or less than one third (<33%); or at least 4-fold higher (≥400%) or less than one fourth (<25%); or at least 5-fold higher (≥500%) or less than one fifth (<20%).

The term "genomic site of interest" or "GOI" as used herein shall refer to a genetic sequence of interest which is any nucleic acid sequence endogenous to a cell, such as, for example a gene or a non-coding sequence within or adjacent to a gene, in which it is desirable to modify by targeted mutagenesis and/or targeted homologous recombination. The GOI can be present in a chromosome, an episome, an organellar genome such as mitochondrial genome. A GOI can be within the coding sequence of a gene, within transcribed non-coding sequence such as, for example, promoter or leader sequences, or introns, or within non-transcribed sequence, either upstream or downstream of a coding sequence.

The term "homolog" or "homology" indicates that two or more nucleotide or amino acid sequences have the same or conserved pairs at a corresponding position, to a certain degree, up to a degree close to 100%. A homologous sequence of a functionally active variant typically has at least about 60% nucleotide or amino acid sequence identity, preferably at least about 70% identity, more preferably at least about 80% identity, more preferably at least about 90% identity, more preferably at least about 95% identity, more preferably at least about 98% or 99% identity. The term "homologous" may also include analogous sequences.

The term "homology template" as used herein refers to a DNA or a DNA sequence or fragment that at least partially hybridizes to a GOI and may act as a donor to introduce specific inserts or exchanging one or more nucleotides within the GOI by homologous recombination or homology-directed repair. Homologous recombination is typically involved in the repair of double-stand breaks which may promote the exchange of genetic information between an endogenous genetic sequence (i.e. a GOI initially present into the cell) and the homology template acting as a donor. Depending on the design of the donor, coding or non-coding regions present on the GOI can be knocked-in (as further described herein) in a rational, precise and efficient manner. The process requires sequence homology between one sequence present on the donor, referred to as homologous or recombining sequence, and the endogenous targeted GOI. Preferably, homologous recombination is performed using two flanking sequences having identity with the endogenous GOI in order to make more precise integration.

Specific homology templates comprise a recombining sequence that is complementary to at least a portion of a single-strand oligonucleotide such that two single-strand oligonucleotides can partially hybridize together. The complementary sequence of the single-strand oligonucleotide can be any length that supports specific and stable hybridization between the two single-strand oligonucleotides under the reaction conditions. The recombining sequence generally authorizes at least a partial double stranded overlap between the homology template and the GOI over at least 10 bp, preferably at least 20 bp.

"Percent (%) identity" with respect to the nucleotide or amino acid sequence is defined as the percentage of nucleotides in a candidate DNA sequence that is identical with the nucleotides in the DNA sequence or the amino acids in a peptide/polypeptide/protein sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

A functionally active variant of a parent sequence as described herein may specifically be obtained through mutagenesis methods. The term "mutagenesis" as used in the context of the present invention shall refer to a method of providing mutants of a sequence, e.g. through insertion, deletion and/or substitution of one or more nucleotides or amino acids, so to obtain variants thereof. Mutagenesis may be through random, semi-random or site directed mutation. Typically large randomized gene libraries are produced with a high gene diversity, which may be selected according to a specifically desired genotype or phenotype.

Preferably the functionally active tracrRNA comprises or consists of a nucleotide sequence of at least 50 bases, specifically at least 60 bases, typically up to 90 or 100 bases. According to a specific example, the truncated tracrRNA is typically about 60 bases long, preferably 60-70 bases, e.g. 66 bases long, the full-length tracrRNA is typically 90 bases long. Some of the preferred functionally active variants of the tracrRNA according to the invention are size variants or specifically fragments of a tracrRNA including truncated versions, preferably those including the 3' part of the tracrRNA molecule, e.g. including a truncated 5' part of a nucleotide sequence. For example a nucleotide sequence derived from one of exemplary tracrRNA nucleotide sequences which has a specific length and insertions or a deletion of the 5' terminal region, e.g. an elongation or truncation of the nucleotide sequence at the 5' end, so to obtain a specific length with a range from the 3' end to a varying 5' end, such as with a length of the nucleotide sequence of at least 50 bases, preferably at least 60 bases. The elongated size variant of the invention preferably comprises additional one or more nucleotide(s) at the 5' end of the tracrRNA sequence.

Preferably the functionally active crRNA comprises or consists of a nucleotide sequence of at least 25 bases, specifically at least 30 bases, typically up to 70 or 80 or 90 or 100 bases. According to a specific example, the truncated crRNA is typically about 30 bases long, preferably 30-40 bases, e.g. 32 bases long, the full-length crRNA is typically 50-60 bases long, e.g. 55 bases. Some of the preferred functionally active variants of the crRNA according to the invention are size variants or specifically fragments of a crRNA including truncated versions, preferably those including the 5' part of the crRNA molecule, e.g. including a truncated 3' part of a nucleotide sequence. For example a nucleotide sequence derived from one of exemplary crRNA nucleotide sequences which has a specific length and insertions or a deletion of the 3' terminal region, e.g. an elongation or truncation of the nucleotide sequence at the 3' end, so to obtain a specific length with a range from the 5' end to a varying 3' end, such as with a length of the nucleotide sequence of at least 25 bases, preferably at least 30 bases. The elongated size variant of the invention preferably comprises additional one or more nucleotide(s) at the 3' end of the crRNA sequence.

The functionally active tracrRNA variants may still include a region of complementarity to interact with the constant part of the crRNA. On the other hand, the functionally active crRNA variants may still include a region of complementarity to interact with the trcrRNA. Typically, the 3' part of the crRNA or a functional variant of the crRNA is interacting with the 5' part of the tracrRNA (with or without a linker) through a region of complementarity. Thus, it is preferred that functional variants of the tracrRNA and the crRNA still comprise a region of complementarity which is at least 5 bp, preferably at least 10 bp, specifically located in the 5' part of the tracrRNA and in the 3' part of the crRNA.

Preferably the functionally active RNA-guided endonuclease comprises or consists of an amino acid sequence of 500 to 3000 amino acids, preferably at least 1000 amino acids. Some of the preferred functionally active variants of the endonuclease as used according to the invention are size variants or specifically fragments of a parent enzyme, in particular where the functionally active variants still comprise the active site of the enzyme including a RuvCI domain (containing a catalytic Asp residue) and an HNH domain (containing a catalytic His residue).

A functionally active variant of a crRNA, in particular the variable part of the crRNA, or an oligonucleotide as described for the purpose of the present invention need not be 100% complementary to its target sequence to be specifically hybridizable. An oligonucleotide is specifically hybridizable when binding of the oligonucleotide to the target DNA molecule interferes with the normal function of the target DNA, and there is a sufficient degree of complementarity to avoid non-specific binding of the oligonucleotide to non-target sequences under conditions where specific binding is desired, for example under physiological conditions in the case of in vivo assays or systems. Such binding is referred to as specific hybridization, e.g. hybridization under stringent conditions.

The DNA target site is typically characterized by a protospacer associated motif (PAM), which is a short DNA recognition site located adjacent to the target site in the human DNA sequence and which defines the site of RNA hybridization and the DNA break. Typically, the RNA hybridization is such that the crRNA hybridizes with the DNA sequence upstream the PAM motif, e.g. the DNA sequence joined to the 5' end of the motif. The DNA break is then catalyzed within the region of hybridization, e.g. a DNA break proximal to the PAM motif, in most cases in close proximity to the 5' end of the motif, such as within 10 positions, or within/at 5 positions or within/at 3 positions upstream the PAM motif. Following the DNA break, the cellular repair mechanism provides for rejoining the DNA ends with or without incorporating mutations, typically proximal to the DNA break, e.g. in close proximity to the 5' end or 3' end of the DNA break, such as within 20 positions, or within 10 positions, or within 5 positions or within 3 positions upstream or downstream the DNA break.

A specific genomic target site of interest may be randomly chosen, or predetermined and selected at any position of the human chromosomal genome where a DNA cleavage (single stranded or double stranded DNA break) and optionally recombination and/or mutation is desirable, and where a PAM motif is present or has been introduced, including a target site within coding and non-coding sequences.

Small (random) inserts or deletions of one or more nucleotides may be desirable, e.g. to produce frameshift mutations. In particular, such deletions or insertions or frameshift mutations provide for knockout mutations, which are understood to encompass any mutation within a gene sequence or regulatory sequence directing the function of a gene, e.g. leading to a different gene expression as assessed at the protein level or a different phenotype, e.g. leading to a significant loss of the function of a gene (partial knock-out) or a complete knock-out of the gene. The significant functional loss of a gene specifically provides for a gene expression level or gene function of less than 10%, preferably less than 5%, or no detectable gene expression or function as compared to the parent or reference (e.g. isogenic) cell without the knockout mutation. Specific mutations lead to a different gene expression or a different phenotype. Also, exons or genes or chromosomal parts including a series of genes may be exchanged and marker sites introduced, e.g. restriction sites, or tags.

Therefore, using gRNA, CAS9 can be guided to cleave DNA at any site defined by the guide RNA sequence and including a PAM motif. CAS9 can be expressed and localized to the nucleus of human cells, e.g. employing one or more additional nuclear localization signals (NLS), e.g. at least 1, 2, 3, 4, or 5 repeats of NLS preferably located within N-terminal or C-terminal extensions of the CAS9 amino acid sequence. For example the NLS may be a short peptide sequence of 3 to 15 amino acids, e.g. 5 to 10, such as 7 amino acids, which facilitates the active transport of the complex of RNA-guided endonuclease with the gRNA through the nuclear pores. Putative NLS sequences can be found and derived from the SV40 Large T Antigen or Nucleoplasmin Exemplary NLS sequences are, e.g. PKK-KRKV (SEQ ID 6, from SV40 Large T antigen), KRPAAT-KKAGQAKKKK (SEQ ID 49, from Nucleoplasmin), PAAKRVKLD (SEQ ID 50, from c-Myc), PPRKKRTVV (SEQ ID 51, from HCV NS5A) or PRPPKMARYDN (SEQ ID 52, from human RNA helicase A).

RNA expression systems commonly used for delivery of RNA molecules to the cell may be employed. According to a specific embodiment, the endonuclease is co-expressed together with a tracrRNA and/or crRNA and/or gRNA designed to target a specific human coding or non-coding sequence, e.g. a human gene to impair or knock out the function of the gene. A suitable DNA may be used in an expression construct to express the tracrRNA and/or crRNA and/or gRNA or the functional pair of the tracrRNA or gRNA or the constant part of the gRNA and the RNA-guided endonuclease. Therefore, there is further provided such DNA which is a template DNA, e.g. comprising the sequence encoding the tracrRNA and/or crRNA and/or gRNA and/or the constant part of the gRNA, and optionally a DNA encoding the RNA-guided endonuclease, specifically operably linked to regulatory sequences to express such molecules in vivo or in vitro.

The RNA(s) may be synthesized ex vivo, e.g. in vitro transcribed RNA or synthetic RNA, and delivered to, e.g. (co-)transfected into, a cell by suitable means.

Transfection of RNA or the DNA encoding such RNA may be accomplished by a variety of means known to the art including, e.g., electroporation, microinjection, liposome fusion, lipofection.

According to a specific aspect, transformed or transfected cells transiently express the inserted DNA or RNA for limited periods of time. For instance, the foreign DNA or RNA persists in the nucleus of the cell for several days.

Transfection may as well be stable to produce a stable transfectant, e.g. introducing and optionally integrating foreign DNA or RNA into the transfected cell.

Likewise, the endonuclease may be produced by a cell transformed by a DNA encoding the endonuclease, in particular a codon-optimized DNA, or produced separate from the cell, and delivered to the cell by suitable means, including electroporation. For instance, the endonuclease may be fused to a peptide sequence enabling penetrance of the plasmamembrane (such as the cationic peptide derived from HIV-1 Tat or a peptide derived from the antennapedia homeodomain), thereby enabling the direct application of purified protein to cells.

The term "isolated" or "isolation" as used herein with respect to a nucleic acid, e.g. an isolated gRNA an isolated constant part of the gRNA, an isolated tracrRNA or crRNA, or an isolated protein, e.g. an isolated RNA-guided endonuclease, or an isolated functional pair, such as an isolated pair or complex of a gRNA or a tracrRNA associated or bound to the RNA-guided endonuclease, shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those chemically synthesized.

Nucleic acids of the invention are specifically provided as "isolated nucleic acid" or as an "isolated nucleic acid sequence". This term, when applied to RNA or DNA, refers to a molecule that is separated from sequences with which it is immediately contiguous in the naturally occurring organism. For example, an "isolated nucleic acid" may comprise a DNA molecule inserted into a vector, such as a plasmid, to express the respective gRNA encoded by such DNA. An "isolated nucleic acid" (either DNA or RNA) may further represent a molecule produced directly by biological or synthetic means and separated from other components present during its production.

An isolated RNA-guided endonuclease is typically provided as a molecule isolated from a natural source, e.g. a bacterial cell culture, or provided as a recombinant molecule obtained from a recombinant host cell culture, or provided as artificial product obtained by a suitable method of synthesis. Such isolation typically involves suitable methods of purification, e.g. to obtained a purity of at least 80%, preferably at least 90% or at least 95%, up to 100% (w/w).

The term "isolated" as used herein with respect to a cell or clone, e.g. isolated by limited dilution optionally followed by cultivating single cells to grow a clone (a single cell clone), shall refer to such cell or clone that has been sufficiently separated from the environment with which it would naturally be associated, so as to exist in "substantially pure" form. The isolated clone would not contain viable cells of a different clone, e.g. derived from an isolated cell with different genomic properties. Typically, different clones or subclones differ in at least one genomic mutation or SNP, thus, can be differentiated from cells of the same clone or subclone by genomic analysis. "Isolated" does not necessarily mean the exclusion of artificial or synthetic mixtures with other clones or materials, or the presence of impurities, in particular cellular components other than viable cells, that do not interfere with the fundamental activity, and that may be present, for example, due to incomplete isolation.

The term "diploid" as used herein shall specifically refer to a cell or cell line including a genome wherein the cell is disomic or diploid for one or more specific or predetermined genomic loci, e.g. the majority of loci, or even the full genome.

The specific diploid cell line as described herein comprises two sets of sister chromosomes, which are at least partly duplicated, or (nearly) fully duplicated, and is understood to contain two copies (chromatids) formed by the asexual replication of a single chromosome, with both copies being present within one cell. One sister chromosome is therefore understood as one-half of the duplicated chromosome. The set of sister chromosomes specifically comprises homologous chromosomes, which are at least substantially identical (near-diploid) or identical (diploid). The pair of chromosomes having the substantially the same gene sequences, are characterized by substantially the same nucleotide sequence, since the sister chromosomes originate from one parent haploid cell only. The term "substantially identical chromosomes" or "substantially the same nucleotide sequence" is specifically understood in relation to duplicated chromosomes, such as to obtain near-diploid cells as further described herein. A duplicated set of sister chromosomes is created during diploidization of the haploid cell as further described herein.

The term "diploid" specifically includes near-diploid cells and fully diploid cells.

The term "near-diploid" as used herein is understood in the following way. A near-diploid cell is a cell in which no more than 5 chromosomes are present in one copy or more than two copies, e.g. four copies (tetrasomic for the specific genomic loci). In some embodiments, a near-diploid human cell has no more than 1, 2, 3, or 4 chromosomes present in more than two copies. Near-diploid cells can be genomically stable maintaining their status several months in culture. An exemplary near-diploid somatic human cell is a chromosomally stable colon cancer cell line HCT116 [20], or an adherent cell line obtained by a method described herein, e.g. upon diploidization of the near-haploid cell line HAP1 cell line, which again is an adherent cell line obtained by engineering the KBM-7 cell line, which has lost the second copy of chromosome 8, and is hence "more haploid" than its KBM-7 parent, but still retains a portion of chromosome 15 and can therefore not be considered fully haploid. Diploidization of a near-haploid cell line will result in the near-diploid cell line as described herein, which e.g. contains only a couple of tetrasomic genomic loci.

A specific example of a near-diploid somatic human cell line is the cell line C665 which is obtained by diploidization of HAP1 according to the method as further described herein.

The term "fully diploid" as used herein shall specifically refer to a cell or cell line including a genome comprising human chromosomes or the sister chromosomes in the disomic state. Specifically, the pair of chromosomes is identical, characterized by the same gene sequences, or characterized by the same nucleotide sequence, since the sister chromosomes originate from one parent haploid cell only. Fully diploid cells are e.g. characterized by the absence of heterozygous SNPs the sister chromosomes of complete set.

The term "haploid" as used herein shall specifically refer to a cell or cell line including a genome wherein the cell is fully haploid, comprising human chromosomes in the monosomic state. Haploidy may be determined or tested by known methods, e.g. spectral karyotyping, comparative genomic hybridization or comparative propidium iodide staining.

The term "near-haploid" as used herein is understood in the following way. A near-haploid cell is a cell in which no more than 5 chromosomes are present in two or more copies. In some embodiments, a near-haploid human cell has no more than 1, 2, 3, or 4 chromosomes present in two or more copies. Near-haploid cells were found to maintain their status several months in culture. An exemplary near-haploid somatic human cell is haploid for most chromosomes with the exception of chromosome 8, and optionally a portion of chromosome 15, e.g. a cell of the KBM-7 cell line (WO 2011/006145 A2), which is a non-adherent cell line. A further example of a near-haploid cell line is the HAP1 cell line [6], which is an adherent cell line obtained by engineering the KBM-7 cell line, which has lost the second copy of chromosome 8, and is hence "more haploid" than its KBM-7 parent, but still retains a portion of chromosome 15 and can therefore not be considered fully haploid. Further near-haploid cell lines (in particular adherent cells) may be derived from a cancer patient, specifically a patient suffering from a solid tumor, such as peripheral chondrosarcoma, which brings about cells of reduced diploidy. In some cases, further adherent near-haploid cell lines may be derived from a patient suffering from leukemia, such as Chronic Myelogenous Leukemia or Acute Lymphoblastic Leukemia.

A specific example of a fully haploid somatic human cell line is the HAP2 cell line which is obtained by engineering HAP1 cells through excision of the portion of chromosome 15 that retained its diploidy in the HAP1 cell line, thus, is considered truly or fully haploid. It turned out that the HAP2 cell line comprises the complete set of human chromosomes in the monosomic state. The HAP2 cell line is deposited as DSM ACC3220.

Haploid or diploid progeny can be derived by subcloning the parental cell line and picking haploid and diploid subclones, respectively. Preferably a cell line as described herein shows a genomic stability over at least 10 passages, preferably at least 15 or at least 20 passages, e.g. while avoiding cellular stress conditions. Genetic stability can be assessed by propidium iodide staining (total DNA content) or by spectral karyotyping (single chromosome resolution).

As used in the present invention, the term "hybridization" or "hybridizing" is intended to mean the process during which two nucleic acid sequences anneal to one another with stable and specific hydrogen bonds so as to form a double strand under appropriate conditions. The hybridization between two complementary sequences or sufficiently complementary sequences depends on the operating conditions that are used, and in particular the stringency. The stringency may be understood to denote the degree of homology; the higher the stringency, the higher percent homology between the sequences. The stringency may be defined in particular by the base composition of the two nucleic sequences, and/or by the degree of mismatching between these two nucleic sequences. By varying the conditions, e.g. salt concentration and temperature, a given nucleic acid sequence may be allowed to hybridize only with its exact complement (high stringency) or with any somewhat related sequences (low stringency). Increasing the temperature or decreasing the salt concentration may tend to increase the selectivity of a hybridization reaction.

As used in the present invention the phrase "hybridizing under stringent hybridizing conditions" is preferably understood to refer to hybridizing under conditions of certain stringency. In a preferred embodiment the crRNA as described herein is hybridizing under "stringent hybridizing conditions" to the genomic target site, wherein homology of the two nucleic acid sequences is at least 70%, preferably at least 80%, preferably at least 90%, i.e. under conditions where hybridization is only possible if the double strand obtained during this hybridization comprises preferably at least 70%, preferably at least 80%, preferably at least 90% of A-T or A-U bonds and C-G bonds.

The stringency may depend on the reaction parameters, such as the concentration and the type of ionic species present in the hybridization solution, the nature and the concentration of denaturing agents and/or the hybridization temperature. The appropriate conditions can be determined by those skilled in the art, e.g. as described in Sambrook et al. (Molecular Cloning: A Laboratory Manual, Cold Spring Harbor, 1989).

The term "karyotypically stable" or "stable karyotype" with respect to a cell is herein understood as a genomically stable cell, which does not significantly change its karyotype for specific genomic loci for a prolonged period of time or for a number of passages. The short and long-term genomic stability is a quality criterion of a stable cell line which can be analyzed by routine methods. The karyotypic stability is particularly determined if the haploid or diploid karyotype for the complete set of human chromosomes has proven in more than 90% of the cells in a cell culture. Such cells would essentially not comprise more than the monosomic DNA content (in the case of a haploid cell), or more than the disomic DNA content (in the case of a diploid cell). The genomic or karyotypic stability is a particular feature of the cell line of the invention, which can be used for engineering a series of isogenic mutant cell lines, which differ in the genes or gene expression only at predefined locations.

The term "library" as used herein, e.g. with respect to mutant cell lines of isogenic cells, or with respect to a library of expression plasmids, or with respect to a library of oligonucleotides, is understood as a repertoire or a variety of library members, e.g. cell lines, expression plasmids or oligonucleotides, which library members distinguish from other library members.

The library of cell lines as described herein specifically comprises a library of strains, e.g. human cell lines that have at least one genotypic and/or phenotypic characteristic. Specific library members may comprise different genomic mutations, such as different knockout mutations to produce a variety of genotypes and optionally a variety of phenotypes. It is preferred that libraries are provided comprising a variety of library members, wherein each library member is lacking a functional ORF or the coding sequence of a different single gene.

The cell line library of the invention preferably comprises at least 50, or at least 100, or at least 300, or at least 1.000, or at least 10.000 library members which are characterized by different mutations, e.g. a knockout of different genes in the cell genome. If the mutants are produced by mutagenesis of a parent cell line, a variety of isogenic cells of the same type of the parent cell line is produced.

Each library member may be individually characterized and marked by a selectable marker or a barcode, to facilitate the selection of a library member in the library. Alternatively, the genetic mutation may be determined directly by a suitable determination method, e.g. employing specific probes hybridizing with the mutated region, to select the cell line comprising the mutation.

It may be desirable to locate the library members in separate containers, to obtain a library of cell collections in containers. According to a specific embodiment, the library is provided in an array, e.g. a cell chip, wherein the array comprises a series of spots on a solid carrier, wherein the series of spots include a suspension of one or more cells from a cell collection. Likewise, the cell library may be indexed to nucleic acid arrays.

Such libraries may be used to select specific library members to study the interaction with a predefined substance, e.g. a chemical or biological, such as an inhibitor or enhancer. Specific applications of such library are (i) the identification of genes involved various biological processes, such as the life cycle of a virus or responses to growth factors or cytokines, (ii) the determination of the specificity of an antibody or (iii) the use of a mutant cell line for the production of a biological (antibody, cytokine).

The term "mutagenesis" as used in the context of the present invention shall refer to a method of providing mutants of a sequence, e.g. through insertion, deletion and/or substitution of one or more nucleotides or amino acids, so to obtain variants thereof. Mutagenesis may be through random, semi-random or site directed mutation.

A specific application may be the selection of a suitable host cell, for expressing a recombination product. Cell arrays may be employed to enable highly parallel, high throughput analyses of cell phenotypes that complement efforts for assessing cell growth and morphology, protein expression levels, and imaging of tissues.

According to a specific example, efficient genome editing was performed while only one copy of each gene is present, thus, it is at least 2-fold easier to obtain a knockout as the gene of interest is present at half gene dosage. Yet, the benefit of using haploid human cells is even greater because for gene inactivation, one generally aims at obtaining frameshift mutations and disregards deletion/insertion of 3/6/9 bases that do not disrupt the reading frame. The chance of obtaining a frameshift mutation is ⅔ (66%) for every cleavage event that is inaccurately repaired. So in a haploid human cell line in which cleavage has occurred in 100% of the cells followed by erroneous repair, one obtains a frameshift allele with a 66% chance. In a population of diploid cells in which both alleles are cleaved with an efficiency of 100%, one would obtain frameshift alleles with a ~44% chance (66%×66%) at a maximum. Of course, when a nuclease induces cleavage with a lower efficiency than 100%, the chance of generating 2 frameshift alleles is even less and the advantage of using haploid cells is even greater. In addition, presence of only a single allele prevents gene repair through homologous recombination and thereby further increases the rate of obtaining frameshift alleles.

In haploid human cells, every gene is only present in one copy. As a consequence, mutations can be directly visualized, e.g. by PCR amplification and subsequent Sanger sequencing of the PCR product. According to a specific example, a protocol is used in which the forward primer is fused to an M13 site that enables a generic sequencing protocol using the M13 sequencing primer.

Using this protocol, it can be shown that individual clones obtained from edited cells can easily be characterized by the aforementioned approach. In contrast, chromatograms from diploid cells transduced with the same guide RNA show inconclusive sequencing traces.

According to specific examples it is confirmed that (i) the use of CRISPR in haploid human cells leads to higher editing efficiency; and (ii) the characterization of the editing events is possible by a simple PCR, coupled to Sanger sequencing.

Further, the invention provides for the somatic human diploid cell line obtainable by diploidization of a haploid cell line as described herein. As haploid somatic cells do not naturally occur, results generated in these cells are questioned by the scientific community. As a consequence, a diploid derivative of a haploid cell is considered a valuable asset. This is particularly true in the area of genomic standards for PCR-based diagnostics where the natural genome context and the natural genome copy number are prerequisites for quality control.

As an example, a protocol is described that allows the "conversion" of a haploid cell into a diploid population. To this end, haploid human cells are used for genome engineering to produce a genomic mutation at a GOI (a mutation of interest). Once the mutation has been confirmed by PCR, cells are exposed to stress. Following cellular stress conditions, haploid cells increase their natural tendency to convert to diploid cells. Diploid subclones are then isolated by limiting dilution and quality controlled by propidium iodide staining. As a result of this process, a homogenous population of diploid human cells is produced that are homozygous for the mutation of interest.

Commercial applications of such diploid cell or cell population are e.g. any of the following:
i) Genetic variation between individuals is largely due to single-nucleotide polymorphisms (SNPs). Hence, a cell line in which only one SNP variant is present for every SNP could be useful to study the impact of genetic variation (presence or absence of certain SNPs) on various cellular phenotypes (e.g. gene expression, DNA damage repair, cell proliferation, metabolism, histone modification).
ii) Cellular phenotypes or experimental outcomes that are particularly likely to be affected by SNPs include
a. EPIGENETICS. Epigenetics is the study of heritable changes that are not caused by the DNA sequence. Mechanisms underlying epigenetic regulation include histone modification (e.g. by methylation or acetylation) and modification of DNA (e.g. by methylation or hydroximethylation). Such modifications have been shown to play a role in repressing or activating transcription from certain loci.
b. ENHANCERS. Enhancers are regulatory elements in the human genome that regulate the expression of certain genes or gene clusters.
iii) Certain genes are expressed in a parental-specific expression pattern. This means that they are selectively expressed from the maternal or paternal gene copy. A cell line that has two identical copies might represent an interesting model system to study this phenomenon.
iv) The efficiency of homologous recombination (HR) is highly dependent on the presence of SNPs: If a given region of interest displays many heterozygous SNPs, the efficiency of HR is dramatically decreased. If one wants to use a diploid cell line for HR, it would thus be preferred to have access to a cell line in which both gene copies are perfectly identical and thus HR has a higher likelihood of success.

In addition, one key advantage of such diploid cells is that every resulting clone is homozygous for any given mutation of interest and will thus carry 100% mutation load, while mutagenesis of diploid cells will often yield cell lines that are heterozygous (50% mutation load). This is particularly beneficial for recessive mutations whose phenotype could not be studied in a diploid cell carrying a single mutated allele because the phenotype would be masked by the presence of the second (wild-type) allele.

Specifically, the invention provides invaluable tools, e.g. for establishing cellular disease models or diagnostic standards for various diseases caused by somatic or germline mutations or SNPs. In particular, cell lines can be established in which particular chromosomal sequences (e.g. exons, genes, splice acceptors, promoters, enhancers) have been deleted.

The foregoing description will be more fully understood with reference to the following example. Such example is, however, merely representative of methods of practicing one or more embodiments of the present invention and should not be read as limiting the scope of invention.

EXAMPLES

Example 1

Generation of an Exemplary Fully Haploid Human Cell

HAP1 are derived from the near-haploid human cell line KBM-7. They were unexpectedly obtained during reprogramming (compare [6]). Like KBM-7 cells HAP1 cells maintain a near-haploid status quite stably. In contrast to KBM-7, HAP1 cells adhere to the cell culture flask and HAP1 cells only possess a single copy of chromosome 8. Yet, like KBM-7 cells, HAP1 cells are diploid for a portion of chromosome 15: 61,105,002-89,890,003. Whole genome sequencing of KBM-7 cells indicates that both cell lines are heterozygous within that region. Spectral karyotyping (SKY) of KBM-7 cells revealed that the second copy of chr15: 61,105,002-89,890,003 is attached to chromosome 19 (see FIG. 6).

To obtain a fully haploid human cell line, we deleted the second copy of chr15: 61,105,002-89,890,003 using the recent published CRISPR/CAS9 system. CAS9 is a bacterial nuclease that can be directed by small RNAs to cleave specific loci of interest in human cells. It was surprising that we could induce a deletion of the enclosed region, which is a large chromosomal region.

We generated two sets of two guide RNAs, targeting either of the two boundaries of the heterozygous/diploid region on chromosome 15 (61,105,002 or 89,890,003):

| CRISPR | Region | Sequence (crRNA, DNA template) |
|---|---|---|
| C1 | 61,105,002 | CCAAGGCAACGGGACTGTGC (SEQ ID 53) |
| 02 | 61,105,002 | TCAGGTCTGATGCAGATCGG (SEQ ID 54) |
| 03 | 89,890,003 | CAGCCACATCTACCGCCATG (SEQ ID 55) |
| 04 | 89,890,003 | GTACCTCCCGCTTCAATGTC (SEQ ID 56) |

We co-transfected combinations of guide RNAs with CAS9 to obtain the following conditions:

| Condition | Variable oligonucleotide of crRNA hybridizing with a region in proximity to chr.15: 61,105,002 8 (DNA template) | Variable oligonucleotide of crRNA hybridizing with a region in proximity to chr.15: 89,890,003 (DNA template) |
|---|---|---|
| C1&3 | CCAAGGCAACGGGACTGTGC (SEQ ID 57) | CAGCCACATCTACCGCCATG (SEQ ID 58) |
| C1&4 | CCAAGGCAACGGGACTGTGC (SEQ ID 59) | GTACCTCCCGCTTCAATGTC (SEQ ID 60) |
| C2&3 | TCAGGTCTGATGCAGATCGG (SEQ ID 61) | CAGCCACATCTACCGCCATG (SEQ ID 62) |
| C2&4 | TCAGGTCTGATGCAGATCGG (SEQ ID 63) | GTACCTCCCGCTTCAATGTC (SEQ ID 64) |

Co-transfections were done in the presence of a plasmid containing a blasticidin resistance gene. Transfected cells were selected using 20 µg/ml blasticidin for 24 h.

Once resistant pools of transduced cells had been expanded to considerable numbers, DNA was extracted and subjected to the T7 Endonuclease assay to assess editing at the two genomic loci under the four conditions described above. As shown in FIG. 7, editing occurred at three out of four CRISPR target sites (CRISPR C1, C3 and C4). CRISPR C2 did not induce any genome editing.

Using the same set of samples, we analyzed whether a deletion of chr15: 61,105,002-89,890,003 was detectable in the pool of transduced cells. We used two primer pairs for that purpose:

| Primer pair | Forward primer | Reverse Primer |
|---|---|---|
| 1 | AGGTGAACATCATCCAGAAGGGGCA (SEQ ID 77) | AAGCAGGCACAAAACCAAAGCCTCT (SEQ ID 78) |
| 2 | AGGTGAACATCATCCAGAAGGGGCA (SEQ ID 77) | AAAATAAGGGGACCGGACAGGCTGG (SEQ ID 79) |

While primer pair 2 did not show any specific amplification, primer pair 1 specifically amplified a signal in condition C1&3 that was not detected in any other condition including the parental HAP1 cells (FIG. 8). Based on this, we decided to isolate single-cell clones from this condition by limiting dilution. Of ~200 clones that were screened using the aforementioned "deletion PCR" (primer pair 1), we isolated 5 clones that were positive, indicating that a deletion may have occurred (FIG. 9). Those clones were named according to their original well and include the clones A11, A8, B11, F6 and H1. Of note, clone H1 showed several bands in the aforementioned PCR, suggesting a more complex editing event may have occurred.

Next, we looked for markers of heterozygosity to assess loss-of-heterozygosity in our clones. To this end, we re-analyzed our whole genome sequencing dataset from KBM-7 cells and identified two SNPs close to the boundaries of the heterozygous region. The genomic location of those SNPs and the corresponding primer sequences used to amplify each SNP by PCR are summarized in the following table:

| PCR primers | Genomic Locus | Sequence |
|---|---|---|
| HG5740 | 61113214 | TGTAAAACGACGGCCAGGCT-GCTT AAAATGCAGATTCCAAAG (SEQ ID 65) |
| HG5741 | 61113214 | GGAGAGATAGGGGATAAAGTG-GTG (SEQ ID 66) |
| HG5742 | 89868948 | TGTAAAACGACGGCCAGCA-GACTC TTGAACCCAAACTCTTTC (SEQ ID 67) |
| HG5743 | 89868948 | GGACTGACTTAGTGTCTTT-GCTTTT (SEQ ID 68) |

Forward primers were fused to an M13 sequencing primer binding site (highlighted in bold) to enable direct sequencing of the PCR products.

Using those diagnostic PCRs, we established that loss of heterozygosity had occurred in clone A11 and clone H1 (data not shown). The other clones were still heterozygous (and hence diploid), suggesting that the chr15: 61,105,002-89,890,003 fragment had not been deleted in those clones.

Next we established whether, in the clones A11 and H1, loss of heterozygosity was also detected throughout the entire region of chr15: 61,105,002-89,890,003. To this end, we investigated five SNPs found to be heterozygous in the parental HAP1 cell line:

| PCR primers | Genomic Locus | Sequence |
|---|---|---|
| HG5740 | 61113214 | TGTAAAACGACGGCCAGGCTGCTTAAAATGCAGATTCCAAAG (SEQ ID 65) |
| HG5741 | 61113214 | GGAGAGATAGGGGATAAAAGTGGTG (SEQ ID 66) |
| HG6690 | 74153876 | TGTAAAACGACGGCCAGAGAAGGATTAAGCTCCACTTACCAA (SEQ ID 69) |
| HG6691 | 74153876 | TGAAAGGTATGGGAGAATGTAACAA (SEQ ID 70) |
| HG6696 | 81960730 | TGTAAAACGACGGCCAGTGCAGATGAAAGTTGTTTGCCTAAT (SEQ ID 71) |
| HG6697 | 81960730 | GGAGGGATAGCATTGGGAGATATAC (SEQ ID 72) |
| HG6698 | 84578780 | TGTAAAACGACGGCCAGACTTAGTCCCTTAAAATTGTGCTTCA (SEQ ID 73) |
| HG6699 | 84578780 | ATACATTGAAAGAGCCATGTCTGGG (SEQ ID 74) |
| HG5742 | 89868948 | TGTAAAACGACGGCCAGCAGACTCTTGAACCCAAACTCTTTC (SEQ ID 67) |
| HG5743 | 89868948 | GGACTGACTTAGTGTCTTTGCTTTT (SEQ ID 68) |

The results of the SNP PCRs were as follows: parental HAP1 cells are heterozygous for all SNPs examined here. Yet, strikingly, the clone A11 lost the heterozygosity at all five loci (FIG. 10), indicating that editing had indeed deleted the entire chr15: 61,105,002-89,890,003 fragment. Clone H1 showed a similar pattern of loss of heterozygosity (data not shown).

Finally, we assessed whether clone A11 is still haploid. The rationale was this experiment was that HAP1 cells are less stable than KBM-7 cells with regard to their haploid karyotype. As shown on FIG. 11, the clone A11 is still fully haploid as indicated by the two peaks at intensities 180/360. Importantly, two reference cell lines (one haploid, one diploid) were included in this measurement. In contrast, clone H1 turned out to be diploid and was thus discarded.

So in summary, the aforementioned work enabled the generation of a human cell line that was derived from HAP1, in which the heterozygous portion of chromosome 15 had been deleted. This cell line is, as it stands, the first fully haploid human cell line.

Example 2

Production of Further Clones Derived from Independent Transfection with Cas9 and Guide RNA Abstract Near-haploid human cell lines are instrumental for genetic screens and genome engineering as gene inactivation is greatly facilitated by the absence of a second gene copy. However, no completely haploid human cell line has been described, hampering the genetic accessibility of a subset of genes. The near-haploid human cell line HAP1 contains a single copy of all chromosomes except for a heterozygous 30 megabase fragment of chromosome 15. This large fragment encompasses 330 genes and is integrated on the long arm of chromosome 19. Here, we employ a CRISPR/Cas9-based genome engineering strategy to excise this sizeable chromosomal fragment and to efficiently and reproducibly derive clones that retain their haploid state. Importantly, spectral karyotyping and single-nucleotide polymorphism (SNP) genotyping revealed that these cells are fully haploid with no gross chromosomal aberrations induced by Cas9. Furthermore, whole genome sequence and transcriptome analysis of the parental HAP1 and clones A11 and E9 showed that transcriptional changes are limited to the excised chromosome 15 fragment. Together, we demonstrate the feasibility of efficiently engineering megabase deletions with the CRISPR/Cas9 technology and report the first fully haploid human cell line.

Introduction

In vertebrates, haploidy, the presence of a genome in a single copy, is naturally confined to the stage of the gametes. However, experimentally, haploid somatic cells can be derived from a number of organisms including medaka, mouse and rat. In humans, near-haploid somatic cells have been found in certain tumors including leukemias (Oshimura et al. 1977 [9]; Andersson et al. 1995 [10]) and chondrosarcomas (Bovee et al. 1999 [19]). Importantly, a near-haploid human cell line was isolated from a chronic myeloid leukemia patient and stably cultured over several months (Kotecki et al. 1999 [1]). This cell line, referred to as KBM-7, contains one copy of most chromosomes with the exception of chromosome 8 and a portion of chromosome 15, which are disomic.

Near-haploidy of KBM-7 cells has been exploited to perform large-scale loss of function screens in human cells (Carette et al. 2009 [2]). Such screens have been employed to study a variety of processes in KBM-7 cells, ranging from host-pathogen interactions to signaling and drug mechanism of action. In addition, KBM-7 cells were used to assemble a large library of human isogenic cell lines (Burckstummer et al. 2013 [4]), thereby enabling both forward and reverse genetics experiments in human cells.

KBM-7 cells can be reprogrammed to induced pluripotent stem cells by overexpression of OCT4, SOX2, KLF4 and MYC (Carette et al. 2010 [5]). These reprogramming experiments also yielded a near-haploid cell line with fibroblast-like morphology termed HAP1 (Carette et al. 2011b [6]). In contrast to KBM-7 cells, HAP1 cells are adherent and lack the second copy of chromosome 8. However, HAP1 cells are not fully haploid as they retain two copies of a fragment of chromosome 15, one of which is fused to chromosome 19.

Cas9 is an endonuclease which was first isolated from *Streptococcus pyogenes*. It can be programmed by short guide RNAs (gRNAs) to cleave any genomic locus which is complementary to the guide RNA and followed by a protospacer adjacent motif (PAM; NGG for *Streptococcus pyogenes* Cas9) (Mali et al. 2013 [12]). Cleavage of genomic DNA by Cas9 triggers endogenous repair mechanisms such as non-homologous end joining (NHEJ) that lead to imprecise repair of the breakpoint, thereby causing mutations at the specific locus of interest. Cas9-mediated genome engineering has been used in a variety of organisms from yeast to man (for a review see (Mali et al. 2013 [12])). Importantly, Cas9 has also been used to delete loci of interest (Xiao et al. 2013 [13]), thereby offering enticing perspectives for synthetic biology. However until now only kilobase size deletions have been reported, raising the question if larger deletions can be engineered with high enough efficiency to obtain genetically modified clones. In this manuscript, we employed the versatile CRISPR/Cas9 system to delete one copy of the disomic portion of chromosome 15 that is present in HAP1 cells. The deleted fragment encompasses 30 million base pairs, encoding 330 human genes, and corresponds to roughly a third of the total size of chromosome 15.

Materials and Methods

KBM-7 cells and HAP1 cells were cultured in IMDM supplemented with 10% FCS. Cells were passaged every 48 h.

Spectral Karyotyping was performed and analyzed by WiCell Cytogenetics. In brief, metaphase chromosome spreads were prepared on slides according to standard cytogenetic procedures. These slide preparations were then hybridized according to the DNA Spectral Karyotyping Hybridization and Detection Protocol provided by Applied Spectral Imaging (ASI) using the supplied SKY probes and detection system. Images were captured and analyzed using HiSKYV spectrum imaging system from ASI.

Selection of SNPs

Heterozygous SNPs were selected from the SNP list published in (Burckstummer et al. 2013 [4]) derived from whole genome sequencing of the KBM-7 parental cell line. Equal spacing of the SNPs and visualization of the genotypes was performed by custom R scripts (R version 3.0.1; package 'ggplot2') based on the cumulative variant list from both whole genome and exome sequencing experiments (see also (Burckstummer et al. 2013 [4])).

CRISPR/Cas9-Mediated Genome Engineering

The following sequences were selected as guide RNAs:

| Guide RNA | Genomic location | Sequence (5'-3') |
|---|---|---|
| gRNA1 | chr15: 61,105,137 | CCAAGGCAACGGGACTGTGC (SEQ ID 97) |
| gRNA2 | chr15: 61,105,238 | TCAGGTCTGATGCAGATCGG (SEQ ID 98) |
| gRNA3 | chr15: 89,889,429 | CAGCCACATCTACCGCCATG (SEQ ID 99) |
| gRNA4 | chr15: 89,889,982 | GTACCTCCCGCTTCAATGTC (SEQ ID 100) |

HAP1 cells were transiently transfected with expression plasmids for *Streptococcus pyogenes* Cas9 and suitable guide RNAs using Turbofectin (Origene) according to manufacturer's instructions. To enrich for transfected cells, we cotransfected a plasmid encoding a blasticidin resistance gene and subjected cells to transient selection with 20µg/ml blasticidin. Transfected cells were either expanded for genomic DNA isolation or for limiting dilution.

Deletion PCR

To assess the deletion of the fragment encompassing chr15: 61,105,002-89,890,003, we isolated genomic DNA using the QIAamp DNA Mini Kit (Qiagen) and subjected it to PCR using GoTaq Polymerase (Promega) and the oligonucleotides HG6090 and HG6093 (see sequences above).

Isolation of Single Cell Clones

Single HAP1 clones were obtained by limiting dilution. To this end, cells were trypsinized and serially diluted to a concentration of 15 cells per ml. 50 µl of this suspension were seeded in each well of a 384 well plate. Individual wells were inspected by microscopy to exclude polyclonal cell lines. Monoclonal cell lines were expanded.

PCR and Sanger Ssequencing to Detect Heterozygous SNPs

The following primer pairs were used to amplify heterozygous SNPs from HAP1 cells (or corresponding clones) using GoTaq Polymerase (Promega):

| PCR primers | Genomic location | Sequence |
|---|---|---|
| HG5740 | chr15: 61,113,214 | TGTAAAACGACGGCCAGGCTG CTTAAAATGCAGATTCCAAAG (SEQ ID 101) |
| HG5741 | chr15: 61,113,214 | GGAGAGATAGGGGATAAAAGTGGTG (SEQ ID 102) |
| HG6690 | chr15: 74,153,876 | TGTAAAACGACGGCCAGAGAAG GATTAAGCTCCACTTACCAA (SEQ ID 103) |
| HG6691 | chr15: 74,153,876 | TGAAAGGTATGGGAGAATGTAACAA (SEQ ID 104) |
| HG6696 | chr15: 81,960,730 | TGTAAAACGACGGCCAGTGCAGA TGAAAGTTGTTTGCCTAAT (SEQ ID 105) |

-continued

| PCR primers | Genomic location | Sequence |
|---|---|---|
| HG6697 | chr15: 81,960,730 | GGAGGGATAGCATTGGGAGATATAC (SEQ ID 106) |
| HG6698 | chr15: 84,578,780 | TGTAAAACGACGGCCAGACTTAGT CCCTTAAAATTGTGCTTCA (SEQ ID 107) |
| HG6699 | chr15: 84,578,780 | ATACATTGAAAGAGCCATGTCTGGG (SEQ ID 108) |
| HG5742 | chr15: 89,868,948 | TGTAAAACGACGGCCAGCAGACT CTTGAACCCAAACTCTTTC (SEQ ID 109) |
| HG5743 | chr15: 89,868,948 | GGACTGACTTAGTGTCTTTGCTTTT (SEQ ID 110) |

Each forward primer contained an M13 primer binding site labeled in bold. PCR products were purified and directly subjected to Sanger sequencing using the M13 sequencing primer (TGTAAAACGACGGCCAG, SEQ ID 111).

Propidium Iodide Staining

Cells were treated with 100 ng/ml KaryoMax (GIBCO) for 6 h or left untreated, harvested by trypsinization and washed twice with PBS. Cells were simultaneously lysed and stained using Nicoletti buffer (0.1% sodium citrate, 0.1% Triton X-100, 0.5 U/ml RNase A, 20 U/ml RNase Ti, 50 µg/ml propidium iodide). Haploid and diploid reference cell lines were included as controls. Propidium iodide staining was quantified by flow cytometry.

Whole Genome Sequencing and Analysis

Genome DNA was subjected to library preparation for whole genome sequencing using Illumina TruSeq DNA PCR-free sample preparation kit according to manufacturer's instructions. Libraries were sequenced on an Illumina HiSeq 2000 using paired-end 100 bp read chemistry. We aligned the data onto the human genome (hg19) using Bowtie2 and analyzed variants using Bamformatics (sourceforge.net/projects/bamformatics) and custom R scripts. We checked for artifactual alignments using secondary alignments produced by GSNAP. Whole genome sequencing data were deposited on the Short Read Archive (HAP1 cells: SRPO44390; eHAP A11 and E9: SRPO44387).

RNA Sequencing and Analysis

Total RNA (1 µg) was subjected to library preparation using Illumina TruSeq RNA sample preparation kit according to manufacturer's instructions. DNA libraries were sequenced on an Illumina HiSeq 2000 using 50 by single-read chemistry. We aligned reads with Tophat using Gencode (V19) gene annotations. We evaluated expression on genes by counting reads and weighting by mapping multiplicity. For over/under expression analysis, we considered genes with a minimum expression level (FPKM 5), a fold change of 2, and clearance on the uncertainty levels. For the segmentation analysis, we computed the logarithm of fold changes for all expressed genes (FPKM 0.2), arranged them in chromosomal order, and then applied piecewise-flat segmentation. The segmentation values were then used to compile a genome-wide amplification map. All RNA sequencing data were deposited on the Short Read Archive (SRPO44391).

Results

Spectral karyotyping of HAP1 cells revealed that the chromosome 15 fragment present in the parental KBM-7 cell line is retained in HAP1 (FIG. 12). It is fused to the long arm of chromosome 19. To map the boundaries of the disomic region on chromosome 15, we analyzed small nucleotide polymorphism (SNP) array data from KBM-7 cells (Burckstummer et al. 2013 [4]). These data indicate that the disomic fragment encompasses almost 30 million base pairs (from around chr15: 61,105,000 to around chr15: 89,890,000). The presence of heterozygous SNPs from this region shows that the disomic region did not arise by duplication. Instead, it represents a remnant of its diploid heterozygous origin.

To generate a fully haploid somatic human cell line, we aimed to eliminate one copy of the disomic region from chromosome 15 by CRISPR/Cas9-mediated genome engineering. We reasoned that co-application of two guide RNAs positioned at the boundaries of the disomic region would result in the simultaneous cleavage of both ends by Cas9, leading to the elimination of the intervening fragment. As the precise sequence of the chromosome 19/15 fusion was not known, we opted for guide RNAs cleaving within the disomic region from chromosome 15. We designed four gRNAs, two for each end. Cas9 and the guide RNA expression plasmids were introduced by transient transfection of HAP1 cells. We included a plasmid bearing a blasticidin resistance gene and eliminated untransfected cells using blasticidin selection. Following transient transfection of HAP1 cells, we monitored Cas9 cleavage at the four loci using the T7 endonuclease assay. We found that gRNAs 1, 3 and 4 elicited efficient cleavage at the designated loci, while gRNA 2 did not cause any detectable genome modification (data shown in example 1). Next, we assessed whether the deletion could be detected in the pool of transfected cells. We designed two primer pairs to flank the 30 million base pair-region from chromosome 15 that we aimed to delete. As expected, no PCR band was detectable in wild-type HAP1 cells. However, we readily detected a PCR product in the sample in which gRNAs 1 and 3 had been combined (data shown in example 1), indicating that the DNA ends exposed by double strand breaks had been joined together.

While it was encouraging to detect the deletion in the pool of transfected cells, it may still represent a very rare event, complicating the isolation of a clonal cell line carrying the deletion. We isolated clones from the sample in which gRNAs 1 and 3 had been combined and assessed the presence of the deletion by PCR. A first batch of 200 clones contained four clones (designated A8, A11, B11 and F6) in which the deletion was detectable by PCR (data shown in example 1). Clones were isolated and further characterized as part of example 1. The most promising clone from this set was clone A11. It was positive for the deletion PCR, showed loss-of-heterozygosity and was still haploid. For that reason, clone A11 was included in the set of experiments presented here.

A second batch of 200 clones that was independently derived contained one additional such clone (designated E9; FIG. 13). Sanger sequencing of the deletion PCR products obtained from clones A11 and E9 showed different breakpoints in the two clones (FIG. 14), demonstrating that these clones originated from independent editing events.

To exclude the possibility that the excised region of chromosome 15 had been retained by integrating somewhere else in the genome, we analyzed SNPs from the disomic region from chromosome 15 that were found to be heterozygous in HAP1 cells (FIG. 15). We observed that both clones (A11 and E9) were homozygous for these SNPs (FIG. 15). This indicates that proper deletion had occurred in clones A11 and E9.

To characterize the chromosomal landscape in the various clones, we subjected each clone to spectral karyotyping. Clones A11 and E9 were found to be fully haploid and chromosome 19 was intact (FIG. 16), indicating that the defective chromosome 19/15 fusion had been repaired as intended. These two clones can therefore be considered fully haploid human cell lines.

As HAP1 cells can spontaneously convert to a diploid state, we assessed the stability of the clones in which deletion had occurred. Propidium iodide staining showed that both clones A11 and E9 were haploid (FIG. 17) and indistinguishable from haploid HAP1 cells. When passaged for 20 passages, HAP1 cells as well clone E9 retained perfect haploidy, while clone A11 had partially converted to diploidy, possibly by endoreduplication. This indicates that fully haploid human cells are viable and can stably maintain their haploid karyotype.

We decided to further characterize clones A11 and E9 by performing whole genome sequencing and we included the parental HAP1 cells in these analyses. Whole genome sequencing was performed at ~20× coverage in HAP1 and ~6× coverage in clones A11 and E9, respectively. A global comparison between HAP1 and clone E9 showed similar relative coverage across the genome, with the exception of the fragment from chromosome 15, for which HAP1 cells showed twice the coverage in comparison to clone E9 (FIG. 18). Similar results were obtained for clone A11 (data not shown). This observation supports the notion that the complete disomic region from chromosome 15 had been deleted in clones A11 and E9.

Global analysis of single-nucleotide substitutions and short indels revealed that the majority of the single-nucleotide substitutions that were lost in the clones with regard to their HAP1 parent could be attributed to the chromosome 15 fragment that had been deleted (data not shown). Both clones also acquired some mutations due to genetic drift (data not shown). Overall, the whole genome sequencing confirmed the data obtained by spectral karyotyping, highlighting the deletion of the chromosome 15 fragment and suggesting only minor additional alterations in these cells.

Finally, we compared near-haploid HAP1 cells to the fully-haploid clones A11 and E9 by RNA sequencing. We also included KBM-7 cells as a control. To control for variability due to culturing conditions we included two replicates derived from parallel cultures. Remarkably, the Spearman correlations between HAP1 and clone E9 were just as strong as those between replicates of the same cell line (FIG. 19A). This indicates that the global expression profile of HAP1 and clone E9 cells is nearly identical. Of note, the number of genes that differed between HAP1 and clone E9 by at least two-fold was around 600, whereas this number was over 3000 genes compared to KBM-7 cells (FIG. 19B). Furthermore, the majority of genes that were differentially expressed between HAP1 and clone E9 clustered on the deleted fragment of chromosome 15 (FIG. 20). Altogether, our RNA sequencing data indicate no major differences between clones A11 or E9 and HAP1 and shows mainly differences arising from the large chromosomal deletion we engineered.

Discussion

We present here a megabase-scale deletion, engineered by CRISPR/Cas9, that greatly exceeds published deletions (Xiao et al. 2013 [13]), thus demonstrating the feasibility of chromosome-scale genome engineering. Importantly, engineered chromosomally stable clones could be obtained using a standard subcloning and PCR screening procedure. Large deletions up to 24 megabases have been reported using Zinc finger nucleases (Lee et al. 2010 [14]) or TALENs (Kim et al. 2013 [15]), but the efficiency cannot always be inferred because few studies reported the isolation of single clones carrying these deletions. In cases when single clones were isolated, they were retrieved at a surprisingly high frequency (around 0.5%) (Kim et al. 2013 [15]), given the fact that TALENs are generally believed to be less efficient than the CRISPR/Cas system. When finalizing this manuscript, we noticed several recent reports showing large deletions (Canver et al. 2014 [16]) or chromosomal rearrangements (Choi and Meyerson 2014 [17]) as a consequence of paired CRISPR/Cas cleavage. Efficiencies reported for mono-allelic megabase-scale deletions were in the range of 1% (Canver et al. 2014 [16]) and are thus comparable to our findings.

We based our excision strategy on available SNP array data, which depend on the presence of heterozygous SNPs and thus provide a lower resolution than whole genome sequencing. The whole genome sequencing data we obtained in the meantime revealed that the disomic region from chromosome 15 comprises the following positions: chr15:61,103,219-89,893,074. As a consequence, we did not eliminate the chromosome 15 fragment completely. In fact, in clones A11 and E9, chromosome 19 still contains a fragment of a few kilobases (~2 kb from around chr15:61 M and ~4 kb from around chr15:89M).

One major concern with the use of the CRISPR/Cas9 system is the cleavage at undesired sites that are closely related to the on-target site and several recent reports highlight the possibility of off-target editing. However, the frequencies at which off-target editing is observed vary from low to considerable. Some of these apparent differences may be attributed to the expression level of Cas9 that varies between different cell types, depending on transfection efficiency. Other such differences may be attributed to the method of detection. We observe very limited, if any, off-target editing in clones A11 or E9 cells (data not shown).

The use of the CRISPR/Cas9 system for deletion of specific genomic regions of interest paves the way for the functional characterization of promoters, enhancers and other regulatory regions in the human genome. Moreover, the inactivation of entire gene clusters by deletion will enable the study of gene families composed of individual members with redundant functions. An enticing application of this technology is the creation of a minimal-essential genome that is sufficient for a human cell to survive and proliferate in culture.

Moreover we present the first fully haploid human cell line. Although haploid cells from other organisms had been isolated previously, only near-haploid human cell lines had been reported. Nonetheless, the near-haploid cell lines KBM-7 and HAP1 have demonstrated the value of sub-diploid karyotypes for functional genomics (Carette et al. 2009 [2]; Carette et al. 2011a [11]). The ploidy of a cell is a critical determinant for the success of any genome editing technology: Unlike in diploid or polyploid cell lines, editing events can be easily traced by PCR and Sanger sequencing. Indeed, the modal gene copy number of frequently used cells lines such as HeLa and A549 far exceeds that of a diploid cell line which may severely hamper genome editing. Thus, from a genome engineering and functional genomics perspective, haploid cells are highly attractive. In line with this consideration, one of the first genome-wide CRISPR/Cas9 screens was conducted in KBM-7 cells (Wang et al. 2014 [18]). We therefore anticipate that this fully haploid human cell line will become the workhorse for genome engineering and screening in the broader scientific community.

Example 3

Diploidization of Adherent Somatic Haploid Cells

The following example describes the methodology of diploidization.

Haploid human cells have a natural tendency to convert to the diploid state. Haploid cells are thus herein considered a "metastable" state that ultimately converts to the stable diploid state. In this experiment, this conversion is performed in a controlled way and triggered by suboptimal cell culture conditions, e.g. if cells are not passaged and supplied with fresh medium in regular intervals. Cellular stress would promote the diploidization of haploid somatic human cell lines, in particular when applied to adherent cells.

Following exposure to stress as induced by continued passage, e.g. following at least 25 numbers of passaging, single cell clones were isolated by limiting dilutions. To this end, a population of cells containing haploid and diploid subclones were trypsinized and diluted to ~20 cells per milliliter. Cells were then seeded in 384 well plates ("limiting dilution") and were allowed to grow for 14 days. Single wells were visually inspected to make sure that single cell clones were retrieved.

Single clones were expanded from 384 well plates to 6 well plates. Individual clones were stained by propidium iodide staining. To this end, HAP1 cells were harvested by trypsinization and washed twice with PBS. Cells were simultaneously lysed and stained using Nicoletti buffer (0.1% sodium citrate, 0.1% Triton X-100, 0.5 U/ml RNase A, 20 U/ml RNase T1, 50 µg/ml propidium iodide). Haploid and diploid reference cell lines were included as controls. Propidium iodide staining was quantified by flow cytometry.

A representative result is shown in FIG. 21. Clones 1, 3 and 6 are haploid and display a major (1 N) peak at a fluorescence intensity of ~190 and a minor (2 N) peak at a fluorescence intensity of ~380. The latter arises from haploid cells that duplicated their genome in S phase and are about to undergo mitosis. Clones 2, 4 and 5 are diploid and display a major (2 N) peak at a fluorescence intensity of ~380 and a minor (4 N) peak at a fluorescence intensity of ~760. So in summary, haploid and diploid clones can be clearly separated and identified by propidium iodide staining and analytical FACS.

To generate a homogenous sub-population of diploid clones and avoid clonal artefacts, several diploid clones were pooled to obtain a polyclonal population of diploid cells. In contrast to the parental population of haploid HAP1 cells, this population is no longer meta-stable, but stably maintains its diploid or near-diploid karyotype. This population can be distinguished from the original haploid population by propidium iodide staining (FIG. 22). Haploid HAP1 and KBM-7 cells (FIG. 22A and 22B) are nicely haploid with major peaks at a fluorescence intensity of ~220 (1 N) and ~440 (2 N). In contrast, the peaks for diploid KBM-7 cells and the cell line C665 are shifted by ~2 fold (FIG. 22C and 22D), indicating that it is diploid or near-diploid.

C665 was also characterized by spectral karyotyping (FIG. 23). Panels A, B and C show various sub-clones that are present in the population of C665. Some clones in the population are perfectly near-diploid, i.e. they have two copies of each chromosome that is present in haploid HAP1 cells in a single copy (FIG. 23C). Other clones contain minor chromosomal aberrations, such as a trisomy of chromosome 8 (FIG. 23B) or a translocation of a portion of chromosome 8 to chromosome 10 (FIG. 23A). Altogether, the spectral karyotyping data show that near-haploid HAP1 cells can be converted to near-diploid cells.

The population of cells derived from such an experiment is unique because it is diploid or near-diploid and contains two identical sets of sister chromosomes. In contrast, naturally-occurring diploid cells contain one chromosome set from the father and one chromosome set from the mother that differ with regards to certain small nucleotide polymorphisms (SNPs). Diploid cells derived from haploid cells are distinct from naturally diploid cells inasmuch as the two genome copies originated from the same haploid copy and thus, there are no heterozygous SNPs.

REFERENCES

[1] Kotecki M, Reddy P S, Cochran B H. Isolation and characterization of a near-haploid human cell line. Exp Cell Res. 1999 Nov 1;252(2):273-80.

[2] Carette J E, Guimaraes C P, Varadarajan M, Park A S, Wuethrich I, Godarova A, Kotecki M, Cochran B H, Spooner E, Ploegh H L, Brummelkamp T R. Haploid genetic screens in human cells identify host factors used by pathogens. Science. 2009 Nov 27;326(5957):1231-5. doi: 10.1126/science.1178955.

[3] Carette J E, Guimaraes C P, Wuethrich I, Blomen V A, Varadarajan M, Sun C, Bell G, Yuan B, Muellner M K, Nijman S M, Ploegh H L, Brummelkamp T R. Global gene disruption in human cells to assign genes to phenotypes by deep sequencing. Nat Biotechnol. 2011 May 29;29(6):542-6. doi: 10.1038/nbt.1857.

[4] Bürckstümmer T, Banning C, Hainzl P, Schobesberger R, Kerzendorfer C, Pauler F M, Chen D, Them N, Schischlik F, Rebsamen M, Smida M, de la Cruz F F, Lapao A, Liszt M, Eizinger B, Guenzl P M, Blomen V A, Konopka T, Gapp B, Parapatics K, Maier B, Stöckl J, Fischl W, Salic S, Taba Casari M R, Knapp S, Bennett K L, Bock C, Colinge J, Kralovics R, Ammerer G, Casari G, Brummelkamp T R, Superti-Furga G, Nijman SM. A reversible gene trap collection empowers haploid genetics in human cells. Nat Methods. 2013 Oct;10(10):965-71. doi: 10.1038/nmeth.2609. Epub 2013 Aug 25.

[5] Carette J E, Pruszak J, Varadarajan M, Blomen V A, Gokhale S, Camargo F D, Wernig M, Jaenisch R, Brummelkamp TR. Generation of iPSCs from cultured human malignant cells. Blood. 2010 May 20;115(20):4039-42. doi: 10.1182/blood-2009-07-231845. Epub 2010 Mar 16.

[6] Carette J E, Raaben M, Wong A C, Herbert A S, Obernosterer G, Mulherkar N, Kuehne A I, Kranzusch P J, Griffin A M, Ruthel G, Dal Cin P, Dye J M, Whelan S P, Chandran K, Brummelkamp T R. Ebola virus entry requires the cholesterol transporter Niemann-Pick C1. Nature. 2011 Aug 24;477(7364):340-3. doi:10.1038/nature10348.

[7] Terns M P and Terns R M. CRISPR-Based Adaptive Immune Systems. Curr Opin Microbiol. 2011 June ; 14(3): 321-327. doi:10.1016/j.mib.2011.03.005.

[8] Jinek M, Chylinski K, Fonfara I, Hauer M, Doudna JA, Charpentier E. A programmable dual-RNA-guided DNA endonuclease in adaptive bacterial immunity. Science. 2012 Aug 17;337(6096):816-21. doi: 10.1126/science.1225829. Epub 2012 Jun 28.

[9] Oshimura M, Freeman A I, Sandberg A A. 1977. Chromosomes and causation of human cancer and leukemia. XXIII. Near-haploidy in acute leukemia. Cancer 40(3): 1143-1148.

[10] Andersson B S, Collins V P, Kurzrock R, Larkin D W, Childs C, Ost A, Cork A, Trujillo J M, Freireich E J, Siciliano M J et al. 1995. KBM-7, a human myeloid leukemia cell line with double Philadelphia chromosomes lacking normal c-ABL and BCR transcripts. Leukemia 9(12): 2100-2108.

[11] Carette J E, Guimaraes C P, Wuethrich I, Blomen V A, Varadarajan M, Sun C, Bell G, Yuan B, Muellner M K, Nijman S M et al. 2011a. Global gene disruption in human cells to assign genes to phenotypes by deep sequencing. Nature biotechnology 29(6): 542-546.

[12] Mali P, Esvelt K M, Church G M. 2013. Cas9 as a versatile tool for engineering biology. Nature methods 10(10): 957-963.

[13] Xiao A, Wang Z, Hu Y, Wu Y, Luo Z, Yang Z, Zu Y, Li W, Huang P, Tong X et al. 2013. Chromosomal deletions and inversions mediated by TALENs and CRISPR/Cas in zebrafish. Nucleic acids research 41(14): e141.

[14] Lee H J, Kim E, Kim J S. 2010. Targeted chromosomal deletions in human cells using zinc finger nucleases. Genome research 20(1): 81-89.

[15] Kim Y, Kweon J, Kim A, Chon J K, Yoo J Y, Kim H J, Kim S, Lee C, Jeong E, Chung E et al. 2013. A library of TAL effector nucleases spanning the human genome. Nature biotechnology 31(3): 251-258.

[16] Canver M C, Bauer D E, Dass A, Yien Y Y, Chung J, Masuda T, Maeda T, Paw B H, Orkin S H. 2014. Characterization of Genomic Deletion Efficiency Mediated by CRISPR/Cas9 in Mammalian Cells. The Journal of biological chemistry.

[17] Choi P S, Meyerson M. 2014. Targeted genomic rearrangements using CRISPR/Cas technology. Nature communications 5: 3728.

[18] Wang T, Wei J J, Sabatini D M, Lander E S. 2014. Genetic screens in human cells using the CRISPR-Cas9 system. Science 343(6166): 80-84.

[19] Bovee J V, Cleton-Jansen A M, Kuipers-Dijkshoorn N J, van den Broek L J, Taminiau A H, Cornelisse C J, Hogendoorn P C. 1999. Loss of heterozygosity and DNA ploidy point to a diverging genetic mechanism in the origin of peripheral and central chondrosarcoma. Genes, chromosomes & cancer 26(3): 237-246.

---

The invention claimed is:

1. A somatic fully haploid, karyotypically stable human cell line, which is the HAP2 cell line deposited at the Deutsche Sammlung von Mikroorganismen und Zellkulturen (DSMZ) under accession number DSM ACC3220.

2. The cell line of claim 1, obtained by targeted deletion of one or more disomic chromosomal regions of a somatic near-haploid human parental cell.

* * * * *

UNITED STATES PATENT AND TRADEMARK OFFICE
CERTIFICATE OF CORRECTION

PATENT NO. : 10,450,586 B2  
APPLICATION NO. : 15/100146  
DATED : October 22, 2019  
INVENTOR(S) : Tilmann Buerckstuemmer Page 1 of 1

It is certified that error appears in the above-identified patent and that said Letters Patent is hereby corrected as shown below:

On the Title Page

In Item (30), "Foreign Application Priority Data", insert:
-- Aug. 4, 2014 (EP).............................. PCT/EP2014/066732 --.

Signed and Sealed this
Sixteenth Day of July, 2024

Katherine Kelly Vidal
*Director of the United States Patent and Trademark Office*